(12) United States Patent
Weiser et al.

(10) Patent No.: US 9,022,920 B2
(45) Date of Patent: May 5, 2015

(54) SYSTEMS, DEVICES, AND METHODS FOR SUB-URETHRAL SUPPORT

(75) Inventors: Michael F. Weiser, Groton, MA (US); George Mamo, Ellicott City, MD (US); Michael S. H. Chu, Brookline, MA (US); Brett Nowlin, Bridgewater, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/226,798

(22) Filed: Sep. 7, 2011

(65) Prior Publication Data

US 2012/0004500 A1  Jan. 5, 2012

Related U.S. Application Data

(63) Continuation of application No. 11/399,913, filed on Apr. 6, 2006, now Pat. No. 8,016,741.

(60) Provisional application No. 60/668,736, filed on Apr. 6, 2005, provisional application No. 60/702,539, filed on Jul. 25, 2005, provisional application No. 60/702,540, filed on Jul. 25, 2205, provisional application No. 60/715,362, filed on Sep. 8, 2005.

(51) Int. Cl.
*A61F 2/02* (2006.01)
*A61B 17/00* (2006.01)
(Continued)

(52) U.S. Cl.
CPC ....... *A61B 17/00234* (2013.01); *A61B 17/0401* (2013.01); *A61B 17/06109* (2013.01); *A61B 2017/0046* (2013.01); *A61B 2017/00805* (2013.01); *A61B 2017/0412* (2013.01); *A61B 2017/0414* (2013.01); *A61B 2017/0417* (2013.01); *A61B 2017/0427* (2013.01); *A61B 2017/0437* (2013.01); *A61B 2017/0445* (2013.01); *A61B 2017/0464* (2013.01); *A61B 2017/0496* (2013.01); *A61B 2017/06009* (2013.01); *A61B 2017/06042* (2013.01); *A61B 2017/06076* (2013.01); *A61B 2017/06085* (2013.01); *A61F 2/0045* (2013.01);
(Continued)

(58) Field of Classification Search
USPC .......... 600/29, 30, 37; 128/885; 606/151, 139
See application file for complete search history.

(56) References Cited

U.S. PATENT DOCUMENTS

| 3,003,155 A | 7/1956 | Mielzynski et al. |
| 5,013,316 A | 5/1991 | Goble et al. |

(Continued)

FOREIGN PATENT DOCUMENTS

| AU | 4092199 | 12/1999 |
| CA | 2333121 | 11/1999 |

(Continued)

OTHER PUBLICATIONS

Kovac, Obstetrics & Gynecology, 89(4):624-627, (1997).
(Continued)

*Primary Examiner* — Christine H Matthews

(57) ABSTRACT

Disclosed are single-incision surgical procedures for treatment of urinary incontinence and/or pelvic floor disorders and related uses, devices, kits, and methods. Implants are also disclosed for use in the exemplary procedures. In certain embodiments, soft tissue anchors are used to anchor the surgical implants to obturator membranes of a patient.

18 Claims, 52 Drawing Sheets

(51) Int. Cl.
*A61B 17/04* (2006.01)
*A61B 17/06* (2006.01)
*A61F 2/00* (2006.01)
*A61F 2/30* (2006.01)

(52) U.S. Cl.
CPC .......... *A61F2002/30062* (2013.01); *A61F 2002/3055* (2013.01); *A61F 2002/30617* (2013.01); *A61F 2210/0004* (2013.01); *A61F 2250/0007* (2013.01); *A61F 2250/0018* (2013.01); *A61F 2250/005* (2013.01); *A61F 2250/0087* (2013.01); *A61F 2250/0097* (2013.01)

(56) References Cited

U.S. PATENT DOCUMENTS

| | | |
|---|---|---|
| 5,112,344 A | 5/1992 | Petros |
| 5,250,054 A | 10/1993 | Li |
| 5,425,740 A | 6/1995 | Hutchinson, Jr. |
| 5,439,470 A | 8/1995 | Li |
| 5,439,474 A | 8/1995 | Li |
| 5,443,472 A | 8/1995 | Li |
| 5,449,366 A | 9/1995 | Li |
| 5,464,189 A | 11/1995 | Li |
| 5,500,000 A | 3/1996 | Feagin et al. |
| 5,520,703 A | 5/1996 | Essig et al. |
| 5,549,636 A | 8/1996 | Li |
| 5,575,805 A | 11/1996 | Li |
| 5,611,515 A | 3/1997 | Benderev et al. |
| 5,643,266 A | 7/1997 | Li |
| 5,645,589 A | 7/1997 | Li |
| 5,649,937 A | 7/1997 | Bito et al. |
| 5,690,649 A | 11/1997 | Li |
| 5,697,931 A | 12/1997 | Thompson |
| 5,702,215 A | 12/1997 | Li |
| 5,707,395 A | 1/1998 | Li |
| 5,715,942 A | 2/1998 | Li et al. |
| 5,741,300 A | 4/1998 | Li |
| 5,776,147 A | 7/1998 | Dolendo |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,935,138 A | 8/1999 | McJames, II et al. |
| 5,954,057 A | 9/1999 | Li |
| 6,022,373 A | 2/2000 | Li |
| 6,039,686 A | 3/2000 | Kovac |
| 6,039,761 A | 3/2000 | Li et al. |
| 6,042,534 A | 3/2000 | Gellman et al. |
| 6,099,538 A | 8/2000 | Moses et al. |
| 6,110,101 A | 8/2000 | Tihon et al. |
| 6,117,161 A | 9/2000 | Li |
| 6,129,762 A | 10/2000 | Li |
| 6,149,669 A | 11/2000 | Li |
| 6,200,330 B1 | 3/2001 | Benderev et al. |
| 6,224,616 B1 | 5/2001 | Kugel |
| 6,273,852 B1 | 8/2001 | Lehe et al. |
| 6,355,053 B1 | 3/2002 | Li |
| 6,406,423 B1 | 6/2002 | Scetbon |
| 6,451,030 B2 | 9/2002 | Li |
| 6,452,450 B1 | 9/2002 | Enriquez |
| 6,478,727 B2 | 11/2002 | Scetbon et al. |
| 6,491,703 B1 | 12/2002 | Ulmsten et al. |
| 6,506,190 B1 | 1/2003 | Walshe |
| 6,575,897 B1 | 6/2003 | Ory et al. |
| 6,582,443 B2 | 6/2003 | Cabek et al. |
| 6,592,515 B2 | 7/2003 | Thierfelder et al. |
| 6,599,323 B2 | 7/2003 | Melican et al. |
| 6,612,977 B2 | 9/2003 | Staskin et al. |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,666,817 B2 | 12/2003 | Li |
| 6,685,629 B2 | 2/2004 | Therin et al. |
| 6,691,711 B2 | 2/2004 | Raz et al. |
| 6,695,855 B1 | 2/2004 | Gaston et al. |
| 6,786,861 B1 | 9/2004 | Pretorius et al. |
| 6,808,486 B1 | 10/2004 | O'Donnell |
| 6,808,487 B2 | 10/2004 | Migliari et al. |
| 6,852,330 B2 | 2/2005 | Bowman et al. |
| 6,884,212 B2 | 4/2005 | Thierfelder et al. |
| 6,884,428 B2 | 4/2005 | Binette et al. |
| 6,911,003 B2 | 6/2005 | Anderson et al. |
| 6,960,160 B2 | 11/2005 | Browning et al. |
| 6,971,252 B2 | 12/2005 | Therin et al. |
| 7,025,063 B2 | 4/2006 | Snitkin et al. |
| 7,070,556 B2 | 7/2006 | Anderson et al. |
| 7,083,568 B2 | 8/2006 | Neisz et al. |
| 7,121,997 B2 | 10/2006 | Kammerer et al. |
| 7,131,944 B2 | 11/2006 | Jacquetin et al. |
| 7,361,138 B2 | 4/2008 | Wagner et al. |
| 2002/0078964 A1 | 6/2002 | Kovac et al. |
| 2002/0083820 A1 | 7/2002 | Greenhalgh |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0133236 A1 | 9/2002 | Rousseau |
| 2002/0138025 A1 | 9/2002 | Gellman et al. |
| 2002/0147382 A1 | 10/2002 | Neisz et al. |
| 2002/0161382 A1 | 10/2002 | Neisz et al. |
| 2002/0183762 A1 | 12/2002 | Anderson et al. |
| 2002/0188169 A1 | 12/2002 | Kammerer et al. |
| 2003/0004399 A1 | 1/2003 | Belson |
| 2003/0004580 A1 | 1/2003 | Sump et al. |
| 2003/0004581 A1 | 1/2003 | Rousseau |
| 2003/0065246 A1 | 4/2003 | Inman et al. |
| 2003/0078468 A1 | 4/2003 | Skiba et al. |
| 2003/0078604 A1 | 4/2003 | Walshe |
| 2003/0114865 A1 | 6/2003 | Sater |
| 2003/0114866 A1 | 6/2003 | Ulmsten et al. |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0191480 A1 | 10/2003 | Ulmsten |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0004600 A1 | 1/2004 | Yoneno et al. |
| 2004/0006353 A1 | 1/2004 | Bosley, Jr. et al. |
| 2004/0015048 A1 | 1/2004 | Neisz et al. |
| 2004/0015057 A1 | 1/2004 | Rocheleau et al. |
| 2004/0039246 A1* | 2/2004 | Gellman et al. .............. 600/30 |
| 2004/0039453 A1 | 2/2004 | Anderson et al. |
| 2004/0039456 A1 | 2/2004 | Davlin et al. |
| 2004/0087970 A1 | 5/2004 | Chu et al. |
| 2004/0097974 A1 | 5/2004 | De Leval |
| 2004/0106847 A1 | 6/2004 | Benderev |
| 2004/0133217 A1 | 7/2004 | Watschke |
| 2004/0144395 A1 | 7/2004 | Evans et al. |
| 2004/0230092 A1 | 11/2004 | Thierfelder et al. |
| 2004/0243166 A1 | 12/2004 | Odermatt et al. |
| 2004/0249240 A1 | 12/2004 | Goldmann et al. |
| 2004/0249397 A1 | 12/2004 | Delorme et al. |
| 2004/0249473 A1 | 12/2004 | Delorme et al. |
| 2004/0267088 A1 | 12/2004 | Kammerer |
| 2005/0004424 A1 | 1/2005 | Raz et al. |
| 2005/0004426 A1 | 1/2005 | Raz et al. |
| 2005/0004427 A1 | 1/2005 | Cervigni |
| 2005/0004576 A1* | 1/2005 | Benderev .................. 606/72 |
| 2005/0021086 A1 | 1/2005 | DeLeval |
| 2005/0043820 A1 | 2/2005 | Browning |
| 2005/0065395 A1 | 3/2005 | Mellier |
| 2005/0070829 A1 | 3/2005 | Therin et al. |
| 2005/0080317 A1 | 4/2005 | Merade |
| 2005/0107834 A1 | 5/2005 | Freeman et al. |
| 2005/0245787 A1 | 11/2005 | Cox et al. |
| 2005/0250977 A1 | 11/2005 | Montpetit et al. |

(56) References Cited

U.S. PATENT DOCUMENTS

| | | |
|---|---|---|
| 2005/0267325 A1 | 12/2005 | Bouchier et al. |
| 2005/0278037 A1 | 12/2005 | Delorme et al. |
| 2006/0041185 A1 | 2/2006 | Browning |
| 2006/0058575 A1* | 3/2006 | Zaddem et al. .......... 600/30 |
| 2006/0058578 A1 | 3/2006 | Browning |
| 2006/0089525 A1 | 4/2006 | Mamo et al. |
| 2006/0205995 A1 | 9/2006 | Browning |

FOREIGN PATENT DOCUMENTS

| | | |
|---|---|---|
| CA | 2427882 | 4/2002 |
| EP | 0632999 | 1/1995 |
| EP | 0643945 | 3/1995 |
| EP | 1191902 | 3/1995 |
| EP | 0774240 | 5/1997 |
| EP | 0677297 | 12/2000 |
| EP | 1079740 | 3/2001 |
| EP | 1324705 | 7/2003 |
| EP | 1333776 | 8/2003 |
| EP | 1342454 | 9/2003 |
| EP | 1345550 | 2/2005 |
| FR | 2811218 | 1/2002 |
| GB | 2382993 | 6/2003 |
| JP | 2002-513632 A | 5/2002 |
| JP | 2004-526483 A | 9/2004 |
| WO | WO 9518571 | 7/1995 |
| WO | WO-9713465 | 4/1997 |
| WO | WO 9716121 | 5/1997 |
| WO | WO-98/35632 | 8/1998 |
| WO | WO 9835632 | 8/1998 |
| WO | 99/56678 | 11/1999 |
| WO | WO 9959477 | 11/1999 |
| WO | WO-00/40158 | 7/2000 |
| WO | WO 00/74594 | 12/2000 |
| WO | WO-00/74613 | 12/2000 |
| WO | WO 00/74613 | 12/2000 |
| WO | WO-0074594 | 12/2000 |
| WO | WO-01/06951 | 2/2001 |
| WO | WO 01/06951 | 2/2001 |
| WO | WO-01/45588 | 6/2001 |
| WO | WO 01/45588 | 6/2001 |
| WO | WO 01/78609 | 10/2001 |
| WO | WO-01/78609 | 10/2001 |
| WO | WO 02/02031 | 1/2002 |
| WO | WO-02/02031 | 1/2002 |
| WO | WO-02/19945 | 3/2002 |
| WO | WO-02/26108 | 4/2002 |
| WO | WO-02/28312 | 4/2002 |
| WO | WO-02/30293 | 4/2002 |
| WO | WO 02/30293 | 4/2002 |
| WO | WO-02/39890 | 5/2002 |
| WO | 02/062237 | 8/2002 |
| WO | WO-02/069781 | 9/2002 |
| WO | WO-02/071953 | 9/2002 |
| WO | WO-02/078548 | 10/2002 |
| WO | WO-02/078568 | 10/2002 |
| WO | WO-03/002027 | 1/2003 |
| WO | WO-03/002029 | 1/2003 |
| WO | WO-03/007847 | 1/2003 |
| WO | WO 03/028584 | 4/2003 |
| WO | WO-03/032867 | 4/2003 |
| WO | WO-03/073960 | 9/2003 |
| WO | WO-03/075792 | 9/2003 |
| WO | WO-03/086205 | 10/2003 |
| WO | WO-03/096929 | 11/2003 |
| WO | WO-03096928 | 11/2003 |
| WO | WO-03096930 | 11/2003 |
| WO | WO-2004/004600 | 1/2004 |
| WO | WO-2004004600 | 1/2004 |
| WO | 2004/016196 | 2/2004 |
| WO | WO 2004/012626 | 2/2004 |
| WO | WO-2004/012626 | 2/2004 |
| WO | WO-2004012626 | 2/2004 |
| WO | WO-2004019786 | 3/2004 |
| WO | WO-2004045457 | 5/2004 |
| WO | WO-2004/045457 | 6/2004 |
| WO | WO-2005007079 | 1/2005 |
| WO | WO-2005/094721 | 10/2005 |
| WO | WO 2005/112842 | 12/2005 |
| WO | WO 2005/122721 | 12/2005 |
| WO | WO-2005/122954 | 12/2005 |
| WO | WO-2005112842 | 12/2005 |
| WO | WO-2007004613 | 1/2007 |

OTHER PUBLICATIONS

Dargent et al., "Pose d'un ruban sous uretral oblique par voie obturatrice dans le traitement de l'incontinence urinaire feminine," Gynecol. Obstet. Fertil, 30:576-582, (2002).

Delorme et al., "Transobturator Tape (Uratape®): A New Minimally-Invasive Procedure to Treat Female Urinary Incontinence," European Urology, 45:203-207, (2004).

"New Improvements in the Treatment of Female Stress Incontinence," European Association of Urologists, American Medical Systems, (2003).

Dargent, D. et al., "Insertion of a Suburethral Sling Through the Obturating Membrane in the Treatment of Female Urinary Incontinence", Gynecol. Obstet. Fertil, 30:576-582, (2002).

de Leval, J., "Novel Surgical Technique for the Treatment of Female Stress Urinary Incontinence: Transobturator Vaginal Tape Inside-Out", European Urology, 44:724-730, (2003).

Delorme, E., "La bandelette trans-obturatrice: unprocede mini-invasif pour traiter l'incontinence urinaire d'effort de la femme", Progres en Urologie, 11, 1306-1313 (2001).

Delorme, E., "The Transobturator Band: A Minimally Invasive Procedure for Treatment of Urinary Stress Incontinence in Women," Progress in Urology, 11, 1306-1313 (2001).

Hermieu, J., et al., Les bandelettes sous-uretrales synthetiques dans le traitement de l'incontinence urinaire d'effort de la feminine, Progres en Urologie, 13, 636-647 (2003).

Notice of Allowance for Japanese Application No. 2011-150151, mailed Feb. 28, 2014, 3 pages.

* cited by examiner

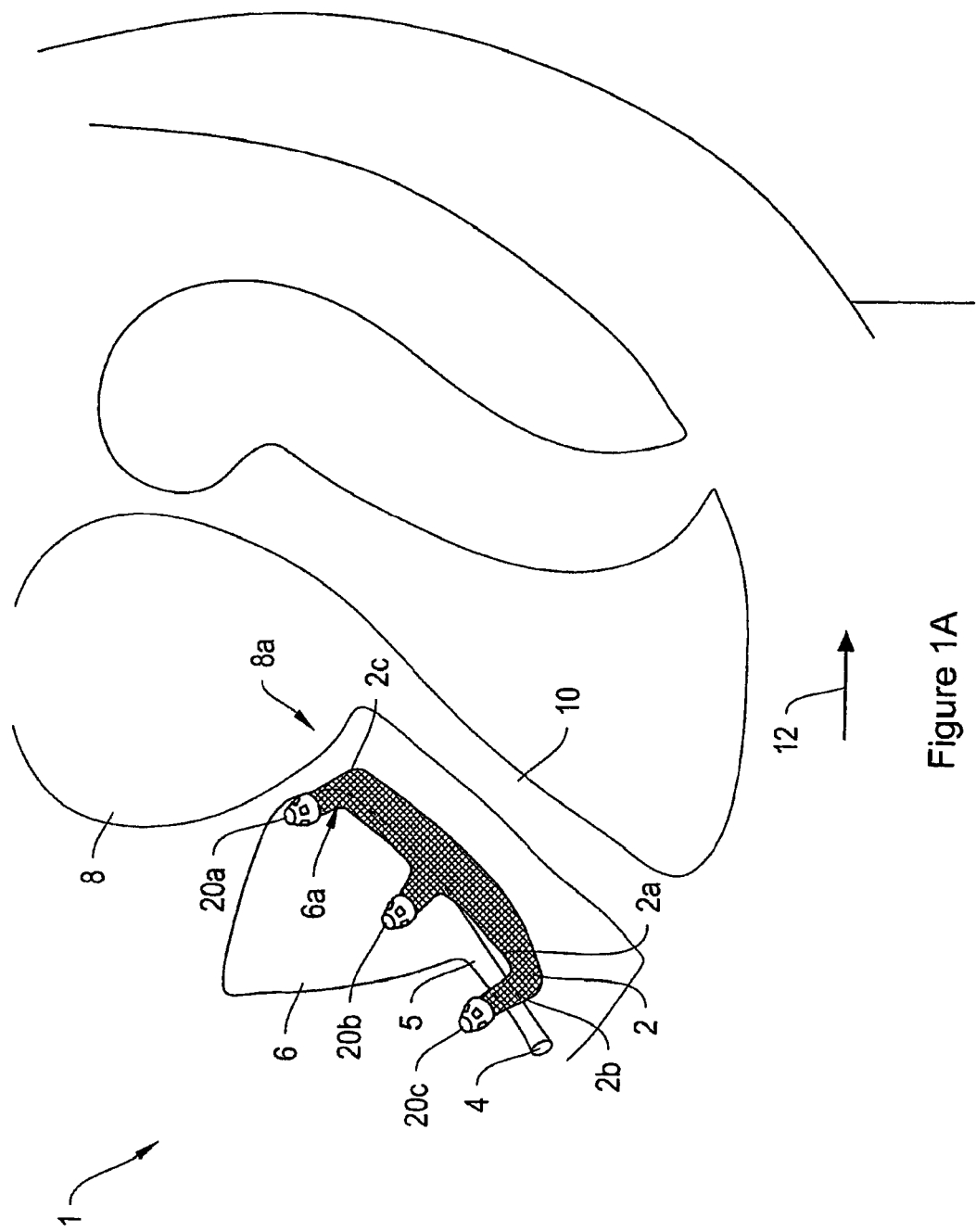

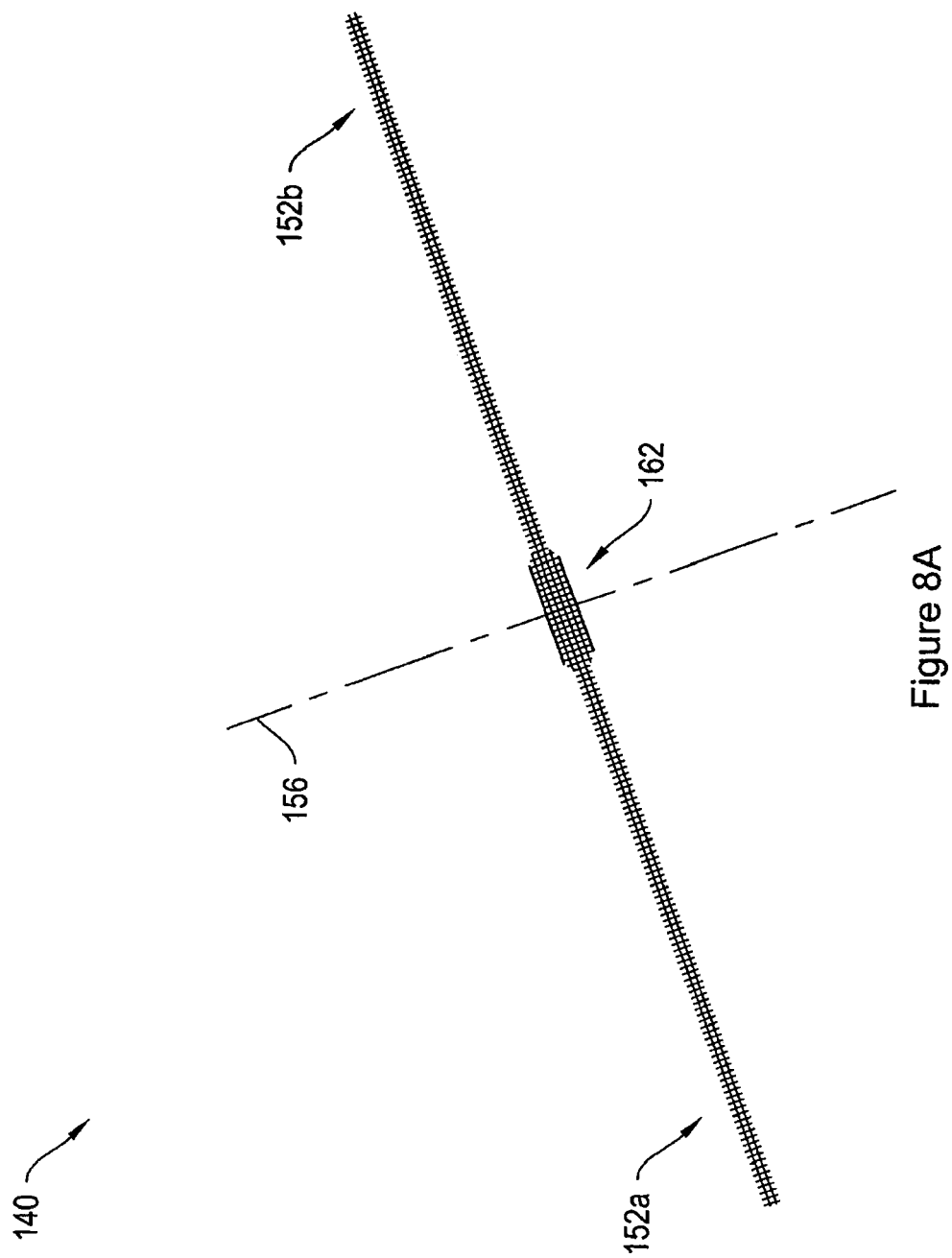

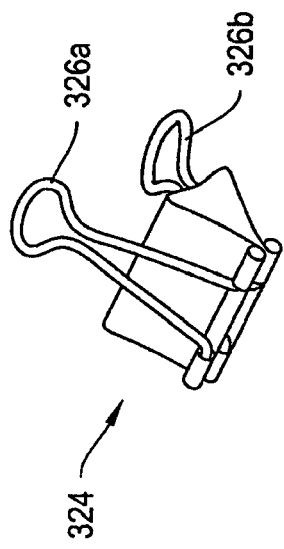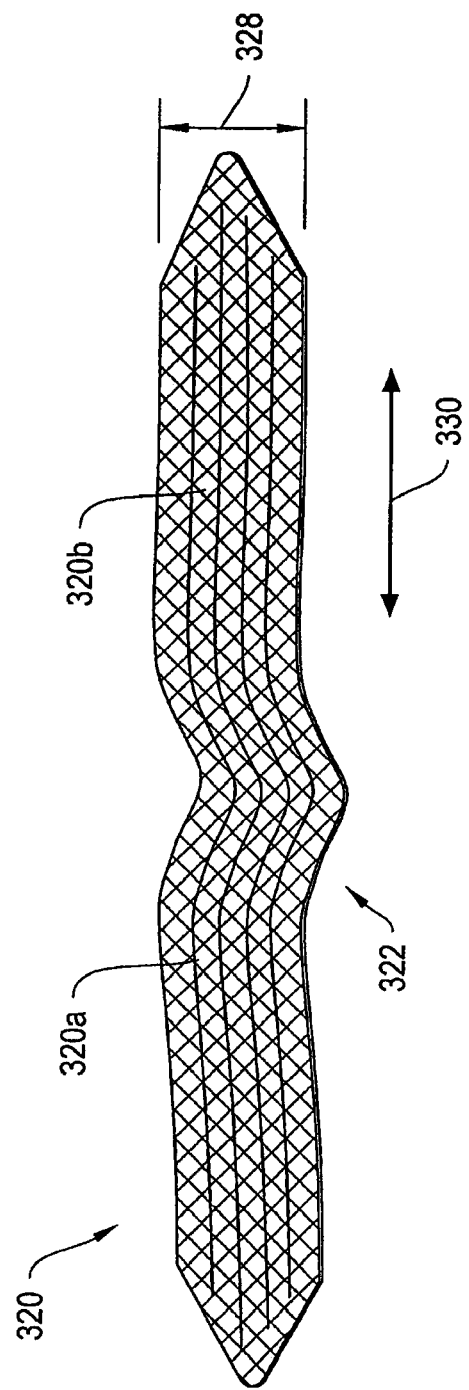
Figure 15B
Figure 15A

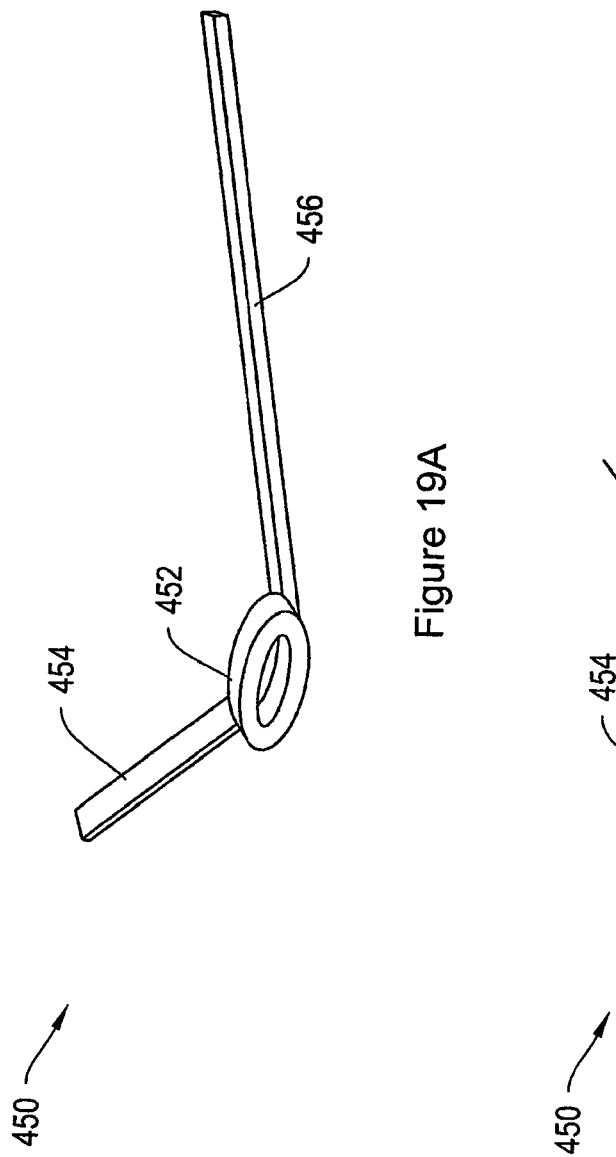
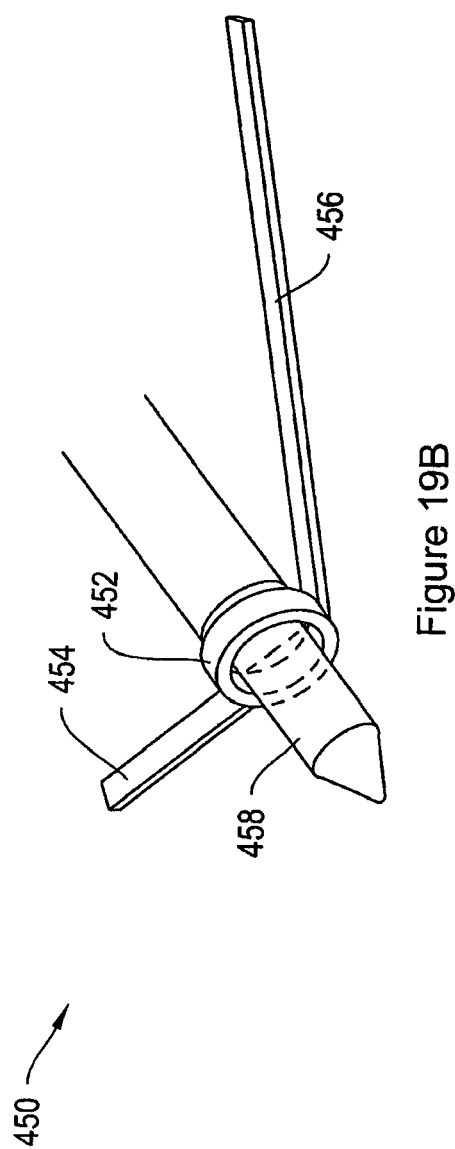

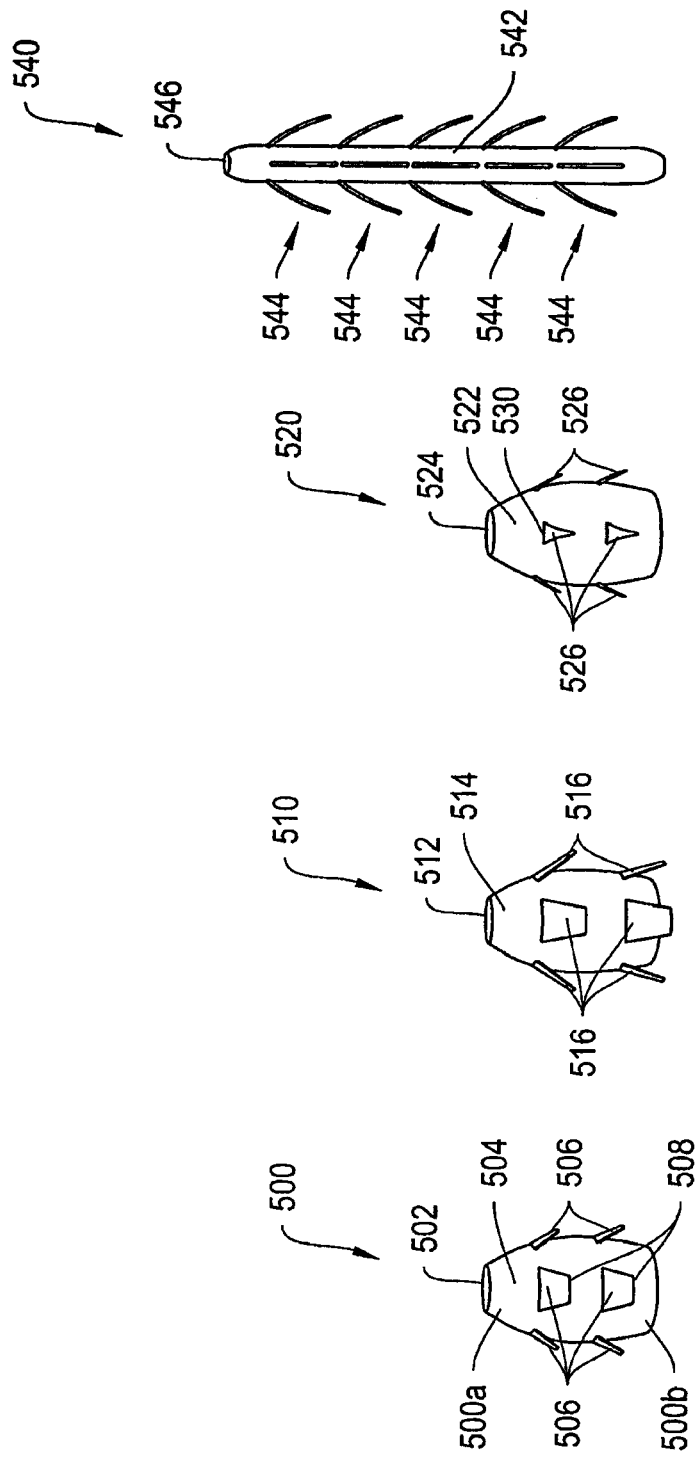

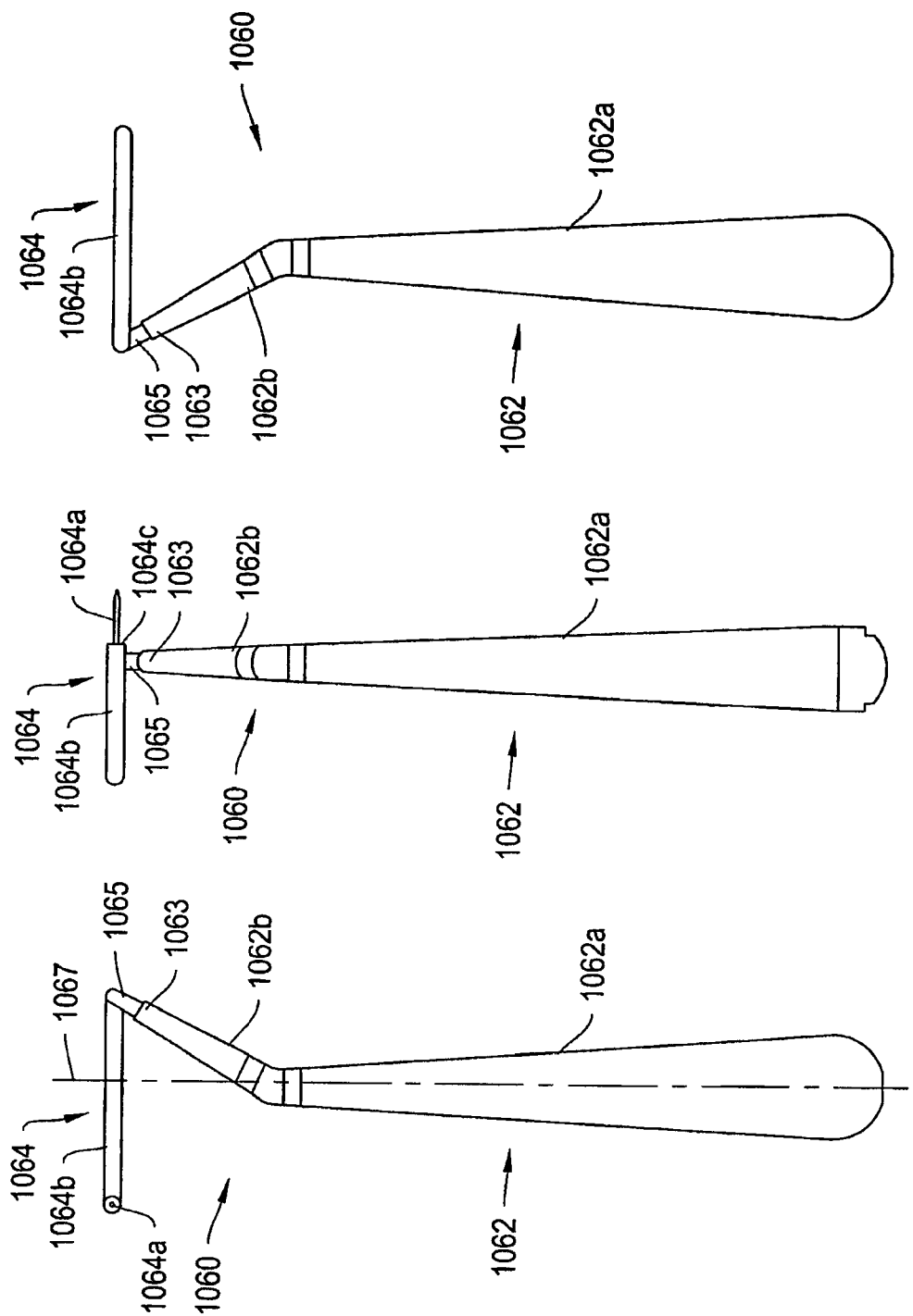

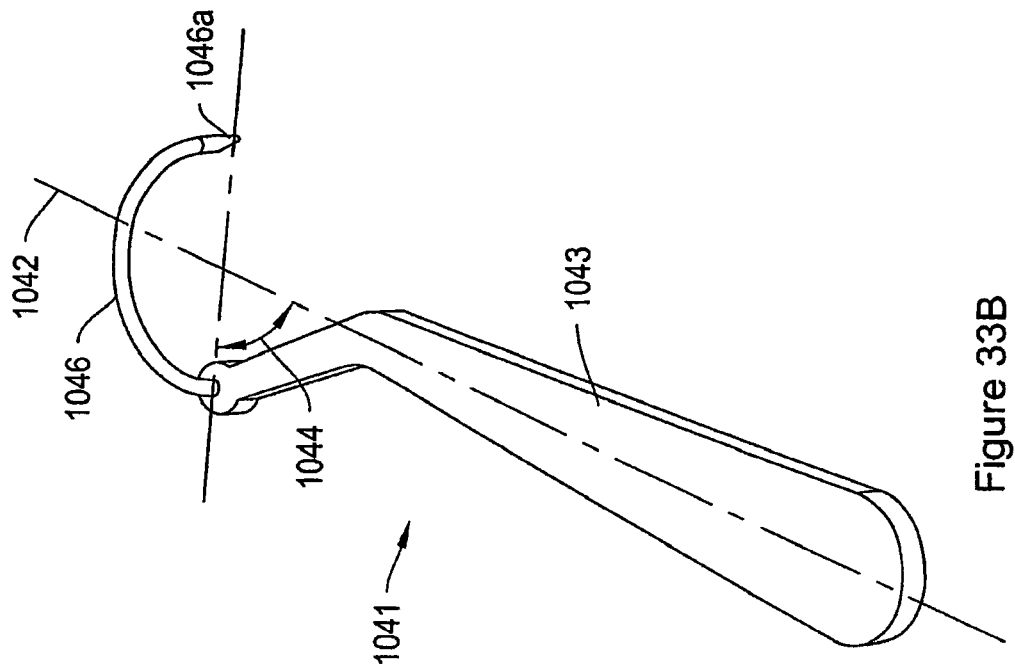
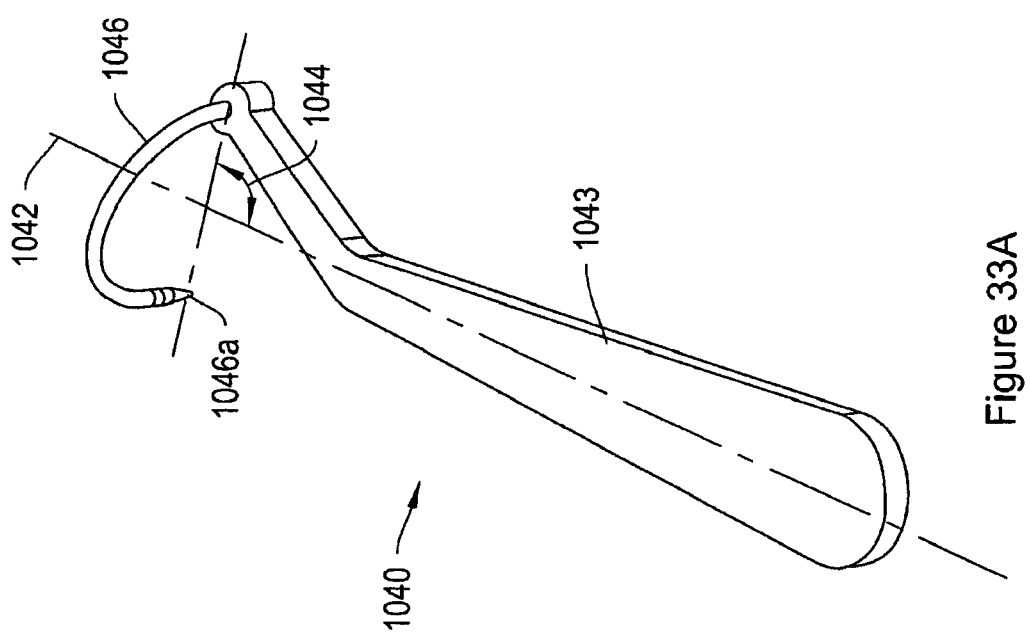
Figure 33B
Figure 33A

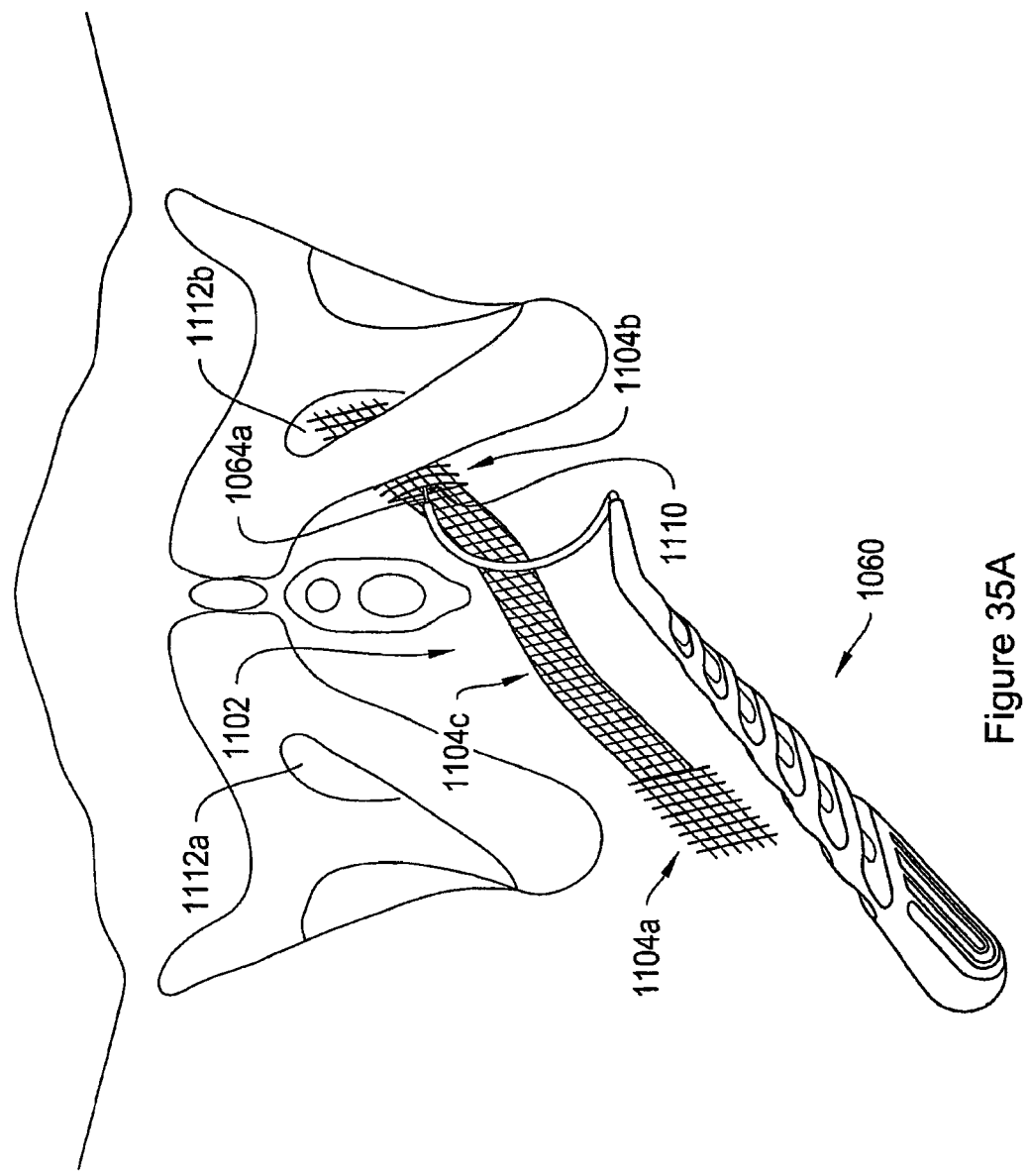

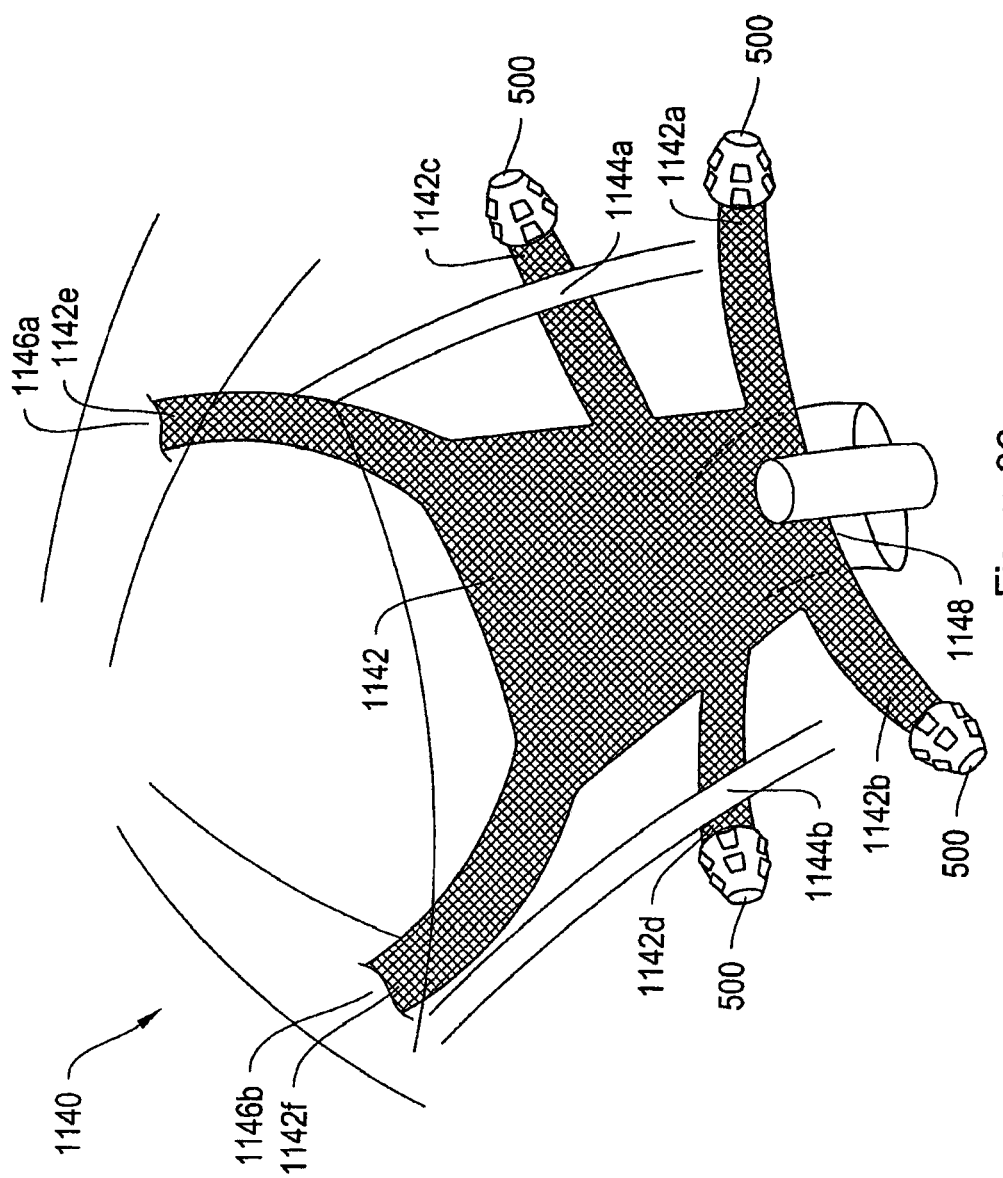

SYSTEMS, DEVICES, AND METHODS FOR SUB-URETHRAL SUPPORT

CROSS-REFERENCE TO RELATED APPLICATIONS

This application is a continuation of U.S. patent application Ser. No. 11/399,913, filed on Apr. 6, 2006, which claims the benefit of U.S. provisional application Ser. No. 60/668,736, filed on Apr. 6, 2005, U.S. Provisional Application Nos. 60/702,539 and 60/702,540, both filed on Jul. 25, 2005, and U.S. Provisional Application No. 60/715,362, filed on Sep. 8, 2005, the contents of which are incorporated by reference herein in their entirety.

BACKGROUND

Pelvic floor disorders are a class of abnormalities that effect the pelvic region of patients, and they afflict millions of women. The pelvic region includes various anatomical structures such as the uterus, the rectum, the bladder, and the vagina. These anatomical structures are supported and held in place by a complex collection of tissues, such as muscles and ligaments. When these tissues are damaged, stretched, or otherwise weakened, the anatomical structures of the pelvic region shift and in some cases protrude into other anatomical structures. For example, when the tissues between the bladder and the vagina weaken, the bladder may shift and protrude into the vagina, causing a pelvic floor disorder known as cystocele. Other pelvic floor disorders include vaginal prolapse, vaginal hernia, rectocele, enterocele, uterocele, and/or urethrocele.

Pelvic floor disorders often cause or exacerbate female urinary incontinence (UI). One type of UI, called stress urinary incontinence (SUI), effects primarily women and is often caused by two conditions—intrinsic sphincter deficiency (ISD) and hypermobility. These conditions may occur independently or in combination. In ISD, the urinary sphincter valve, located within the urethra, fails to close (or "coapt") properly, causing urine to leak out of the urethra during stressful activity. In hypermobility, the pelvic floor is distended, weakened, or damaged. When the afflicted woman sneezes, coughs, or otherwise strains the pelvic region, the bladderneck and proximal urethra rotate and descend. As a result, the urethra does not close with sufficient response time, and urine leaks through the urethra.

UI and pelvic floor disorders, which are usually accompanied by significant pain and discomfort, are often treated by implanting a supportive sling or mesh in or near the pelvic floor region to support the fallen or shifted anatomical structures or more generally, to strengthen the pelvic region by promoting tissue in-growth. Often, treatments of stress incontinence are made without treating the pelvic floor disorders at all, potentially leading to an early recurrence of the stress incontinence.

Existing systems, methods, and kits for treatment typically apply delivery devices to position a supportive surgical sling into a desired position in the pelvic region. However, some of these systems and methods require a medical operator to create multiple incisions and deliver the implant using complex procedures. Moreover, many existing surgical implants are not suitably sized or shaped to properly fit within a patient and treat pelvic floor disorders. Accordingly, medical operators and patients need improved systems, methods, and surgical kits for the treatment of pelvic floor disorders and/or urinary incontinence.

SUMMARY

The invention generally pertains to systems and methods to treat pelvic floor disorders and/or UI through the use of a single incision surgical procedure. In a general single incision technique, the operator makes an incision in the vaginal wall of the patient and uses the single incision as the entry way into the patient's pelvic floor region to provide implants for supporting the urethra, bladderneck, and/or pelvic floor. As explained in more detail below, the single incision approach can be used to insert, position, tension, and secure the implant without the need to make additional incisions in the patient. In practice, the operator makes the single incision in the anterior vaginal wall of the patient and dissects bilaterally to the inferior pubic ramus on each side of the patient. The operator couples a surgical implant to a delivery device, and then guides the device through the single incision and to a target tissue region within the retropubic space on a first side of the pelvic region of the patient.

The implant is secured within the retropubic space by soft tissue anchors, tangs on the implant, or both. In some implementations, the operator couples a first end of the surgical implant to the delivery device by first coupling the first end of the surgical implant to a soft tissue anchor, and then coupling the soft tissue anchor to the delivery device. The operator then secures the soft tissue anchor to the target tissue region and withdraws the delivery device, leaving the first end of the implant anchored to the target tissue region. In other implementations, the surgical implant is directly coupled to the delivery device, and includes tanged end portions that secure to the target tissue region. The operator then repeats this process on a second end of the implant to anchor the second end to a target tissue region to a contra-lateral location in the patient's retropubic space. In certain embodiments, the target tissue regions are located in the obturator membranes of the patient and the implant supports the urethra and/or bladderneck of the patient.

In some configurations, the operator delivers implants that also extend to regions of the pelvic floor that are posterior to the bladderneck, and provides support to anatomical organs such as the bladder. In order to provide implants that provide both anterior and posterior support, the implant is secured to a plurality of target tissue regions on each side of the patient via a plurality of anchors or tanged portions on each side of the implant. In these configurations, the operator repeats the above-described process for each of the anchors or tanged portions. After delivering the implant to the patient's retropubic space, the operator may tension the surgical implant using a tensioning tool inserted through the vaginal incision. The systems and methods include surgical implants, soft tissue anchors that anchor the surgical implants to a desired anatomical location, delivery devices and methods that deliver the anchors and implants through the single incision to desired anatomical locations, and tensioning devices that reposition and/or tension the surgical implants after delivery.

In one aspect, the systems and methods include surgical implants that are sized, shaped, and constructed to treat a variety of pelvic floor disorders. In certain embodiments, the implants are slings that are configured to extend under the urethra and/or bladderneck of the patient for the treatment of urinary incontinence. In other implementations, the implants are larger and configured to extend to and support regions posterior to the patient's bladderneck, including the base of the patient's bladder or further toward the posterior region of the pelvic floor to support other organs.

In certain embodiments, the systems and methods include surgical implant assemblies for pelvic floor repair and/or for treatment of urinary incontinence in a patient. An exemplary assembly includes a surgical implant having a first end, a second end, and a central region adapted to extend to a position posterior to the bladderneck of the patient, and at least one soft tissue anchors coupled to an end of the surgical implant and adapted to secure the implant within the patient's pelvic floor. In certain embodiments, the implant has a first end adapted to extend to a first obturator membrane, a second end adapted to extend to a second obturator membrane, and first and second soft tissue anchors for coupling to respective ones of the first and second ends of the surgical implant and for securing to respective first and second obturator membranes. The implant, in various embodiments, is sized and shaped to support anatomical structures within the pelvic region such as the urethra, bladderneck, bladder, and uterus. The implants, in certain configurations, have anterior-to-posterior widths that allow the implant to extend to posterior regions of the pelvic floor region, including regions posterior to the bladderneck and, in some configurations, posterior to the bladder.

The implant can couple to the soft tissue anchors in a variety of ways based at least in part on the target tissue region where the implant will be secured. In certain configurations, the implant directly couples to and physically contacts the soft tissue anchors. In others, the implant couples to soft tissue anchors by filaments which space the soft tissue anchors away from the implant. The orientation of the mesh with respect to the anchors may be varied to tension or loosen the implant.

An exemplary surgical implant for use with the systems and methods includes a first set of strands and a second set of strands separate from the first set of strands. The first set of strands and the second set of strands are fixedly attached at a plurality of attachment points. An exemplary manufacturing technique includes extruding a first set of strands in a first direction, extruding a second set of strands in a second direction different from the first direction, and attaching the first set of strands and the second set of strands at attachment points.

In one aspect, the systems and methods include implantable surgical sling assemblies for pelvic floor repair and/or for treatment of urinary incontinence in a patient. An exemplary implantable surgical sling assembly includes an implant for extending at least partially between a first obturator membrane and a second obturator membrane of the patient. The implant has a first strap end for aligning with the first obturator membrane, a second strap end for aligning with the second obturator membrane, a first plurality of soft tissue anchors for coupling to the first strap end of the implant and for securing the first strap end to a first soft tissue region, and a second plurality of soft tissue anchors for coupling to the second strap end of the implant and for securing the second end to a second soft tissue region. In certain embodiments, the first and second soft tissue regions are obturator membranes.

In another aspect, the invention includes implantable surgical sling assemblies for pelvic floor repair and/or for treatment of urinary incontinence in a patient. An exemplary implantable surgical sling assembly includes a surgical implant having a first end for securing to a first obturator membrane of a patient and a second end for securing to a second obturator membrane of a patient. The assembly includes a first set of at least three soft tissue anchors for coupling to the first end of the implant and for securing to the first obturator membrane, and a second set of at least three soft tissue anchors for coupling to the second end of the implant and for securing to the second obturator membrane.

The systems and methods also include sling end terminations that may optionally also be soft tissue anchors. In one aspect, the invention includes surgical sling assemblies for pelvic floor repair and/or for treatment of urinary incontinence in the patient. An exemplary assembly includes a surgical sling for supporting at least one of a urethra and a bladderneck of the patient, and a sling housing physically contacting and disposed about an end of the sling. The sling housing includes an aperture and tapers away from a distal end of the sling. In one feature, the sling housing is flexible. The aperture may be a ring, and the housing may include legs extending radially from the ring. In one application, the ring couples to a delivery device, and the legs engage with and anchor to soft tissue.

In another aspect, an exemplary manufacturing technique for an implant is provided, comprising providing a mesh material, coupling the mesh material to a mold, injecting a curable material into the mold, allowing the curable material to cure, and removing the mesh material from the mold. The mesh material may have a pre-selected number of strands or a pre-selected length, width and/or thickness to allow the manufacture of a suitably sized implant.

In another aspect, surgical techniques are disclosed for delivering an implant to a patient. In one implementation, the techniques include a single incision method for implanting a surgical implant in the pelvic floor region of a patient for pelvic floor repair. The exemplary method includes the steps of creating an incision in the vaginal wall of the patient, coupling the implant to a delivery device, inserting the delivery device through the vaginal incision via the external vaginal opening of the patient, and implanting and securing the implant within the pelvic floor region of the patient such that at least a portion of the sling extends to a position posterior to the bladderneck of the patient. The implant may be coupled to soft tissue anchors that anchor into respective soft tissue regions, such as obturator membranes, of the patient, and may additionally or alternatively include tanged portions that secure the implant to the soft tissue regions. The methods may optionally include tensioning the implant. In one feature, the methods include coupling the implant to a delivery device having a shaft and a slidable cannula disposed about the shaft, inserting the delivery device through the external vaginal opening, inserting the delivery device through the vaginal incision subsequent to inserting the delivery device through the external vaginal opening, aligning the shaft with a first obturator membrane, sliding the cannula distally along the shaft, and securing the implant to the first obturator membrane.

In another aspect, the surgical implants are delivered through a single vaginal incision and are secured to the patient's obturator membranes. In particular, according to an illustrative technique, an operator creates a single incision in a vaginal wall of the patient, couples the implant to one or more soft tissue anchors, couples a soft tissue anchor to a delivery device, delivers the soft tissue anchor to an obturator membrane via the single vaginal incision, and anchors the soft tissue anchor to the obturator membrane. The operator repeats this process for any other anchors used, including an anchor for the patient's contra-lateral side, while using the same vaginal incision to insert the anchors and the implant. Either during delivery or subsequent to delivery, the operator optionally tensions the surgical implant. In one aspect, the implant is adjustably coupled to one or more soft tissue anchors, and the operator tensions the surgical implant by adjusting the implant's orientation with respect to its soft tissue anchors.

In certain implementations, a method is provided for treating urinary incontinence in a patient. The method includes providing an implant having at least one tanged portion formed as a unitary body with the implant, creating an incision in the vaginal wall of the patient, coupling an implant to a delivery device, inserting the delivery device through the incision in the vaginal wall via the external vaginal opening of the patient, guiding the device to a location beneath the patient's epidermis, and securing, by the at least one tanged portion, the implant to the patient's soft tissue.

BRIEF DESCRIPTION OF THE DRAWINGS

These and other features and advantages will be more fully understood by the following illustrative description with reference to the appended drawings, in which like elements are labeled with like reference designations and which may not be drawn to scale.

FIG. 1A shows a lateral view of the female pelvic region and an exemplary positioning of a surgical implant.

FIG. 8A shows the implant of FIG. 7A with narrowed tanged portions.

FIG. 15A shows an implant shaped to interfit below a urethra or bladderneck of a patient.

FIG. 15B shows a clip used to shape the implant of FIG. 15A.

FIG. 19A shows a flexible end termination in a collapsed state.

FIG. 19B shows the end termination of FIG. 19A in an expanded state and interfitted with a shaft of a delivery device.

FIGS. 21A-D show exemplary barbed soft tissue anchors.

FIGS. 32A-32C show a delivery device including a handle and a curved halo-shaped shaft.

FIGS. 33A-B show symmetric delivery devices similar to the device of FIGS. 32A-C, but having the curved shaft lie in a plane that is non-orthogonal to a plane of the handle.

FIG. 35A shows aspects of a transobtural single incision procedure for delivering a tanged implant without soft tissue anchors.

FIG. 36 shows an exemplary placement of a surgical implant with straps secured to target tissue regions of obturator membranes, levator ani muscles, and sacrospinous ligaments.

DETAILED DESCRIPTION OF EXEMPLARY EMBODIMENTS

The invention generally pertains to systems and methods to treat pelvic floor disorders and/or UI by using single vaginal incision surgical approaches to deliver surgical implants to the patient's pelvic floor and/or sub-urethral and retropubic space. The implants are secured to soft tissues within the patient's retropubic space by tanged portions of the implant, by one or more soft tissue anchors coupled to the implant, or both. The illustrative devices, systems, and methods of the invention are described below in the following order. First, surgical implants sized, shaped, and constructed for treating UI and/or pelvic floor repair are described. Second, soft tissue anchors are described that, in certain embodiments, secure the surgical implants to a desired anatomical location, such as obturator membranes, along with methods for coupling the soft tissue anchors to the surgical implants. Third, devices are described for delivering the anchors and implants to desired anatomical locations in the patient's retropubic space, such as obturator membranes, along with tensioning devices and methods that reposition and/or tension the surgical implant after delivery. Fourth, exemplary methods are described for implanting and positioning and securing exemplary implants within a patient's pelvic region by use of a single vaginal incision surgical technique.

First, surgical implants sized, shaped, and constructed for treating UI and/or pelvic floor repair are described. The surgical implants described herein are adapted to be secured within the patient's retropubic space. The implants support anatomical structures in the pelvic region and more generally strengthen tissue of the pelvic region. In one aspect, the surgical implants physically support anatomical structures in the pelvic region by providing physical hammock-like support to anatomical structures such as the urethra, the bladderneck, the bladder, the uterus, and other vessels and structures. In order to physically support an anatomical structure, the surgical implants are sized and shaped to support that anatomical structure. In another aspect, surgical implants indirectly strengthen surrounding tissue by promoting tissue in-growth. The surgical implants can be constructed to include apertures or interstices in which tissue in-growth can occur, or may otherwise be constructed of a material that promotes tissue in-growth. Thus, surgical implants may be sized, shaped, and constructed to support anatomical structures and strengthen the tissue of the pelvic region.

Figure 1B:
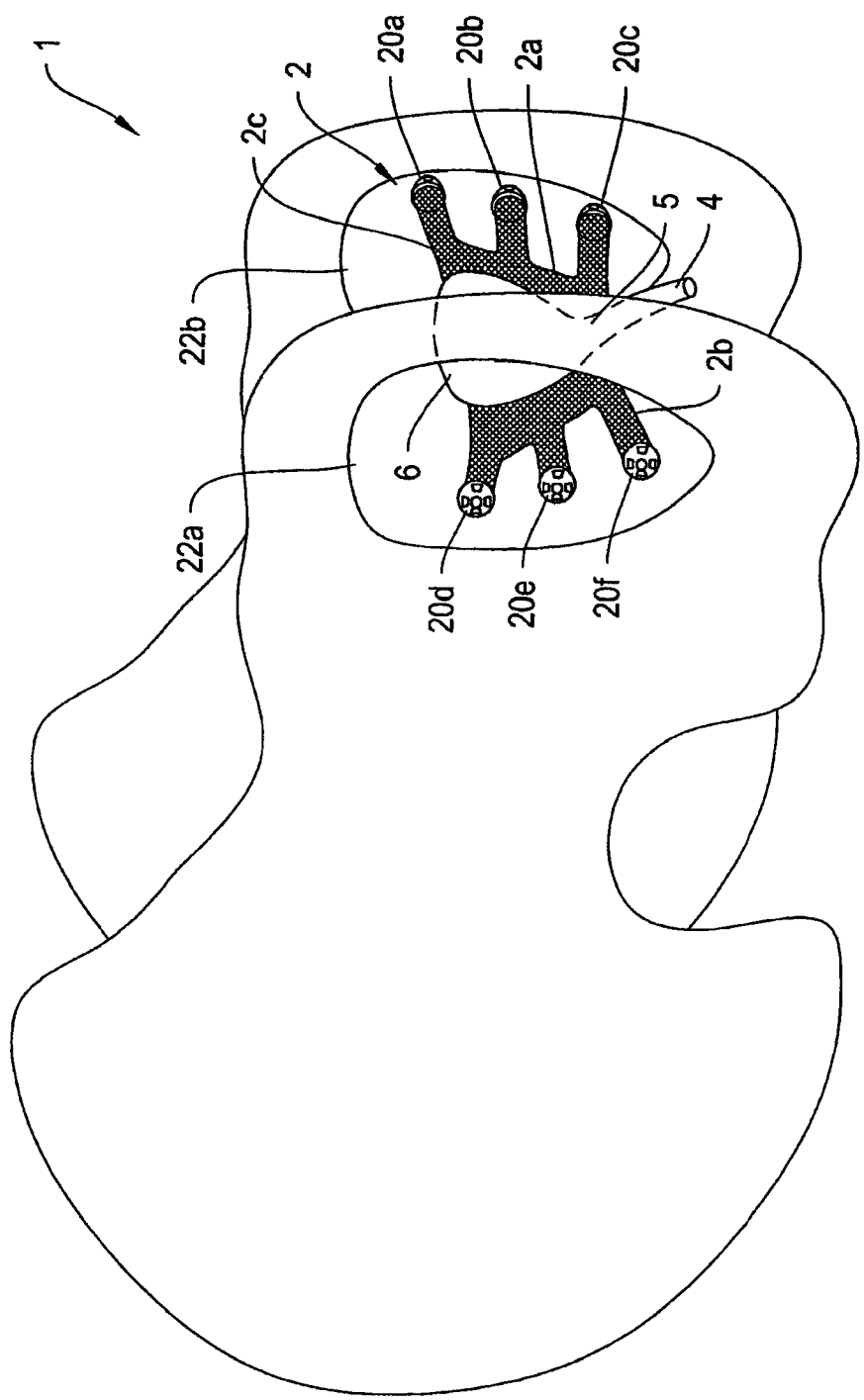
FIG. 1B shows an oblique view of the pelvic region and surgical implant of FIG. 1A.
Figure 1C:
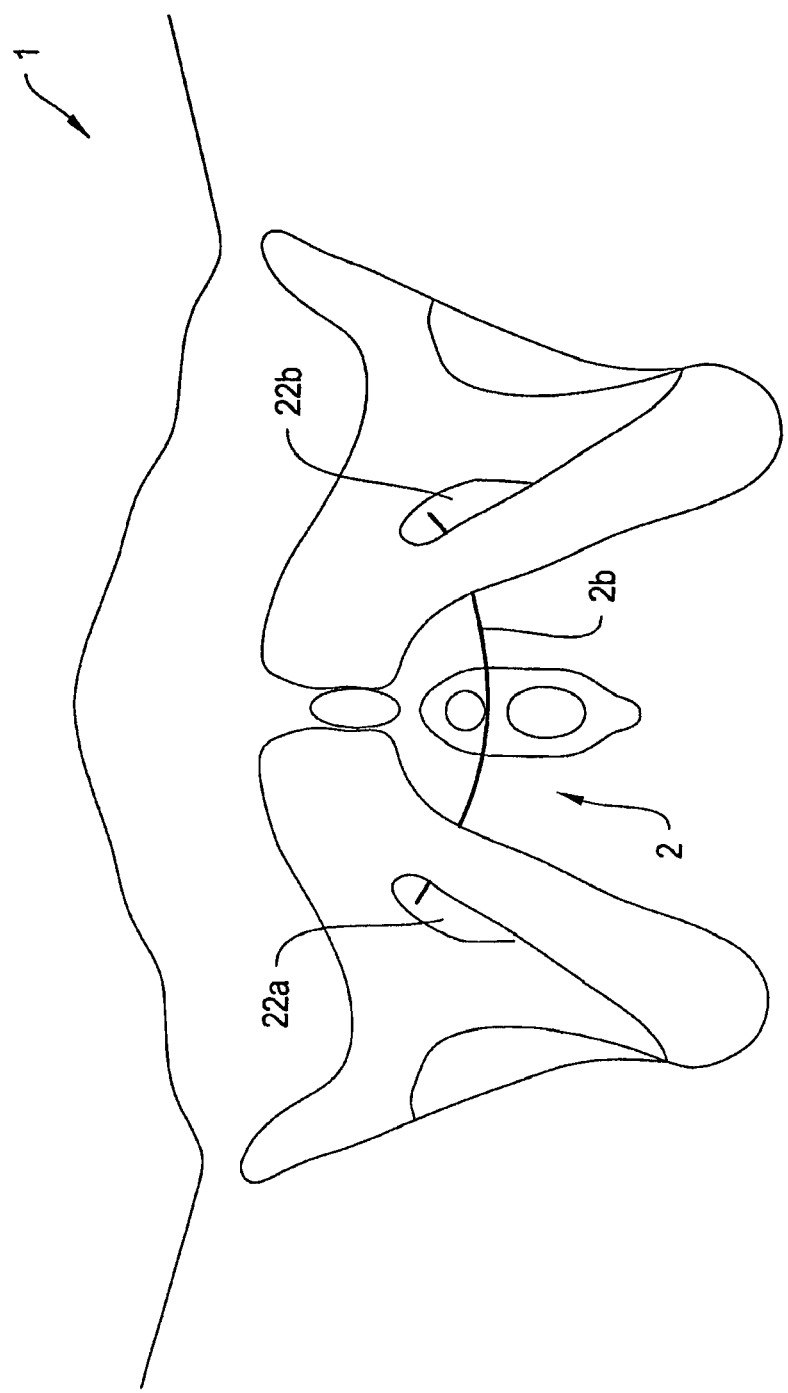
FIG. 1C shows an anterior view of the pelvic region and surgical implant of FIG. 1B.

Turning to the Figures, FIGS. 1A-1C show an exemplary surgical implant 2 that is positioned within the pelvic region 1 of a patient and secured therein through the use of the procedures described herein. FIGS. 1A-1C show the surgical implant 2 having lateral edge 2a, anterior edge 2b, and posterior edge 2c, and being sized, shaped and positioned to support the urethra 4, the bladder 6, and the bladderneck 5 (the region that adjoins the urethra 4 and the bladder 6), of the patient by soft tissue anchors 20a-20f. In particular, FIG. 1A shows a lateral view and FIG. 1B shows an oblique view of the pelvic region 1. As shown, the implant 2 is located in the tissue region directly below the urethra 4 and the bladdemeck 5 with the soft tissue anchors 20a-f anchored into the patient's obturator membranes, the lateral edge 2a located on one side of the urethra 4, bladderneck 5, and bladder 6, and the anterior edge 2b located under the urethra 4 to help strengthen this tissue region in part to treat UI and/or urethrocele. The posterior edge 2c of the depicted surgical implant 2 also extends to a location that is posterior 12 to the bladderneck 5, to support the tissue near the posterior region 6a of the bladder 6 and the inferior region 8a of the uterus 8 to assist in treating other pelvic floor disorders including cystocele, uterine prolapse, enterocele, rectocele, and/or vaginal prolapse. However, because the various tissue regions of the pelvic region are interconnected, strengthening one tissue region often treats disorders afflicting other tissue regions.

FIG. 1C shows an anterior view of the pelvic region 1 with the anterior edge 2b of the implant 2 as described above. The exemplary surgical implant 2 forms a hammock-like support below the urethra 4, the bladdemeck 5, and the bladder 6. The surgical implant 2 is held in position by the six soft tissue anchors 20a-f that anchor to respective obturator membranes 22a and 22b with three such anchors on each side. An obturator membrane is a thick fascial membrane and is located laterally on either side of the pelvic region. The obturator membrane is a convenient supporting structure for soft tissue anchors, such as soft tissue anchors 20a-f, in part because it is strong, and in part because it is large and thus provides lateral, anterior, and/or posterior anchoring locations (in fact, the obturator membrane spans the obturator foramen, the largest foramen in the skeleton).

In the depicted embodiment, the anchors 20a-f couple to surgical implant 2 and anchor directly into the obturator membranes 22a and 22b. However, in alternative embodiments, the anchors 20a-f anchor into muscle tissue located laterally beyond the obturator membranes 22a and 22b. In other embodiments, the implant 2 does not span the full length between the obturator membranes 22a and 22b, known as the obturator-to-obturator length, but instead couples to the anchors 20a-f via filaments or rings that space the implant 2 away from the anchors 20a-f and anchor into the obturator membranes 22a and 22b. In still other embodiments, the implant 2 does not anchor to the obturator membranes 22a and 22b, but instead anchors to other soft tissue regions in the retropubic space, such as the region of the tendinous arch of the levator ani muscle, as discussed below.

Figure 2A:
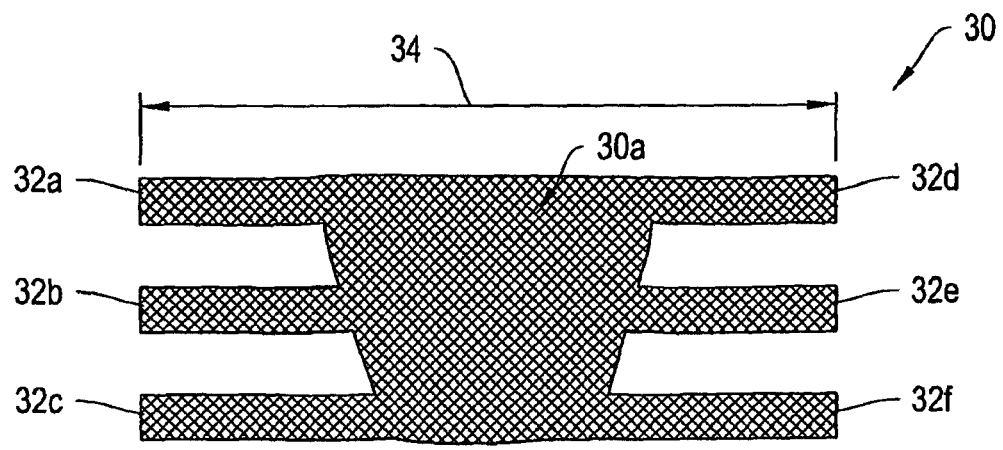
FIG. 2A shows a surgical implant having a central region and six extensions.

The implant 2 may be sized and shaped to achieve a desired patient fit. FIG. 2A shows an illustrative surgical implant 30 of the type shown in FIGS. 1A-1C having a trapezoidal shaped central region 30a and six extension straps 32a-f. In other embodiments the central region 30a is rectangular. In certain embodiments, the implant 30, including straps 32a-f, spans at least a length 34 that extends between or beyond a first obturator membrane and a second obturator membrane of the patient, also known as the patient's obturator-to-obturator length. Thus, when the straps 32a-f are delivered via the single vaginal incision, the straps 32a-c attach to a first obturator membrane either directly or via soft tissue anchors directly coupled to the straps 32a-c, and straps 32d-f attach to the contralateral obturator membrane either directly or via soft tissue anchors directly coupled to the straps 32d-f, as illustrated with respect to FIG. 1AC.

In alternative implementations, the straps 32a-f are secured to other target tissue regions in the patient's retropubic space, such as the patient's sacrospinous ligaments or levator ani muscles. By way of example, straps 32a and 32d may extend to target regions of the sacrospinous ligament, straps 32b and 32e may extend to target regions near the tendinous arch of the levator ani muscle, and straps 32c and 32f may extend to target regions of the obturator membranes. Each of the straps 32a-f may have varying lengths in order to reach their respective target tissue regions.

Figure 2B:
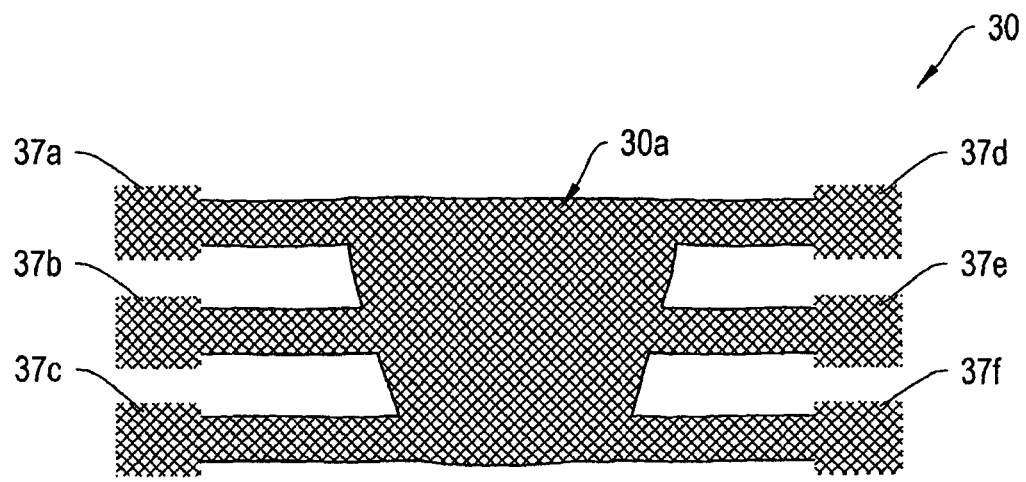
FIG. 2B shows the surgical implant of FIG. 2A having tanged portions on its extensions.

In certain embodiments, the straps 32a-f of the implant 30 have tanged portions that directly secure one or more of the straps 32a-f to a target tissue region. FIG. 2B shows the implant 30 of FIG. 2A, with tanged portions 37a-f at the end of each of the straps 32a-f. In one exemplary technique, these portions are formed by first forming tangs around the edges of the implant 30, and then selectively melting portions of the implant 30 to form the non-tanged portions. More particularly, the implant 30 is first cut from a woven sheet which exposes fibrous protrusions, or the tangs, around the edges of the implant 30. The non-tanged portions are then formed by any process that smoothes, rounds or removes the protrusions, leaving the tangs around the ends of the straps 32a-f. In one implementation, the edges of the implant 30 in the non-tanged portions are heat melted, in another exemplary technique, the tangs in implant 30 are formed from a non-tanged woven tape having the approximate dimensions of the implant 30 as depicted in FIG. 2B. The smooth sides of the tape are then trimmed to produce the frayed edges or fibrous protrusions of the tanged ends of straps 32a-f. In either technique, the tangs are extremities of fibers of the implant, and the tanged ends of straps 32a-f form a unitary body with the implant 30.

Figure 3:
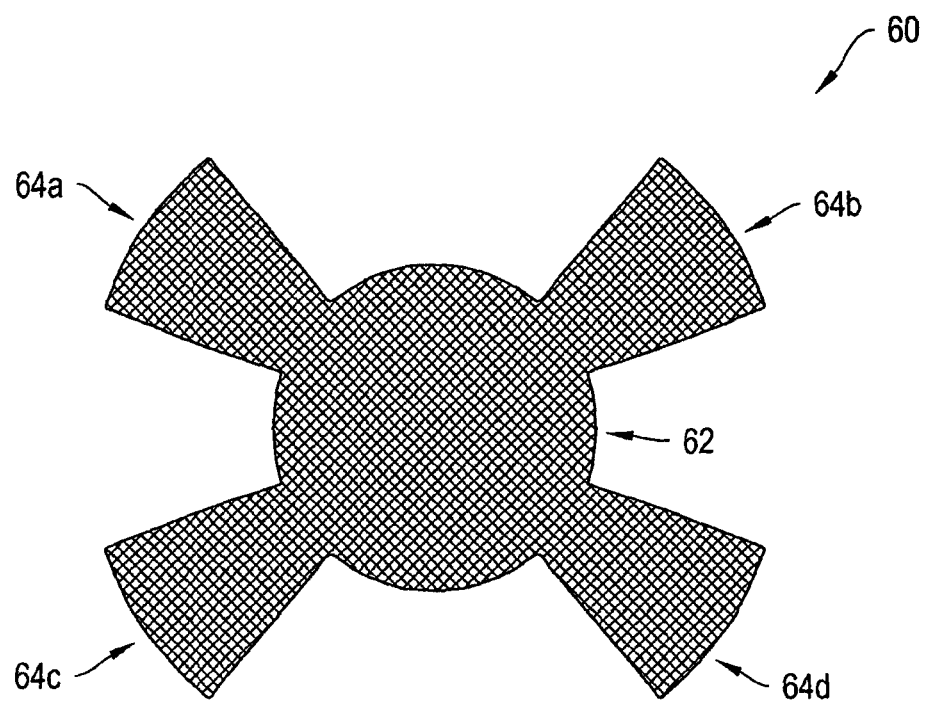
FIG. 3 shows a surgical implant having a circular central region and four extensions.

FIG. 3 shows an alternative configuration of a surgical implant 60 for use in supporting a pelvic region. As shown, the implant 60 has a circular central region 62 and four radially extending extension straps 64a-d. The straps 64a and 64c are designed to extend to one obturator membrane of the patient, and the straps 64b and 64d are designed to extend to the contra-lateral obturator membrane of the patient. The circular central region 62 is suitable for supporting various anatomical structures, including, for example, the base of the bladder. The straps 64a-d can couple with soft tissue anchors for anchoring into respective obturator membranes, as will be discussed below. The depicted implant 60 is a woven mesh; however, a similarly shaped nonwoven implant with tanged straps for anchoring to target tissue regions is discussed below.

As noted in connection with the implant 30 of FIG. 2A, the straps 64a-64d may also be configured to extend to and secure to other target tissue regions in the patient's retropubic space. In one implementation, straps 64c-64d extend to target tissue regions of the patient's obturator membranes, and straps 64a-64b extend to target tissue regions near the patient's tendinous arch of the levator ani muscle.

The implants of FIGS. 2 and 3 described above have extensions/straps that can span the obturator-to-obturator length of patients so that the extensions/straps can directly secure to respective obturator membranes, either alone (using, for example, tangs) or in combination with soft-tissue anchors.

Figure 4:
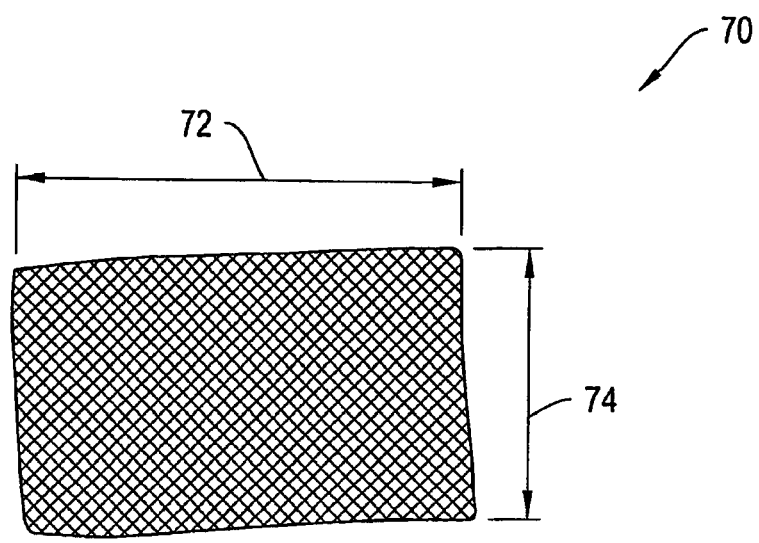
FIG. 4 shows a rectangular surgical implant sized and shaped for pelvic floor repair.

FIG. 4 illustrates an alternative strapless embodiment of a surgical implant 70, having lateral length 72 and, in various embodiments, spanning varying distances between or beyond a first obturator membrane and the contra-lateral obturator membrane of the patient. In certain embodiments the depicted surgical implant 70 does not span the full obturator-toobturator length of many patients, but, as discussed below, couples to soft tissue anchors via long filaments that attach to the implant. The depicted implant 70 has a lateral length 72 of between about 5 centimeters and about 8 centimeters. Alternatively, the implant 25 can have a longer lateral length 72, such as greater than about 7 cm, greater than about 9 cm, or greater than about 10 cm, and thus be sized to span the patient's full obturator-to-obturator length and directly couple to soft tissue anchors that anchor in respective obturator membranes with no intervening filament.

The depicted implant 70 has an anterior-to-posterior length 74 of between about 2.5 centimeters and about 8 centimeters, which allows the surgical implant 70 to extend under and provide hammock-like support to posterior regions of the pelvic region, including, for example, the base of the bladder. In general, the surgical implant 70 can have any desired anterior-toposterior lengths 74 to support other anatomical regions of the pelvic floor. For example, surgical implant 70 can have an anterior-to-posterior length 74 of between about 0.5 cm and about 2 cm and may be suitable to support one or both of the patient's urethra and bladderneck. Alternatively, surgical implant 70 can have an anterior-to-posterior length 74 of greater than about 3 cm, greater than about 5 cm, greater than about 7 cm, or greater than about 10 cm to support the patient's urethra, bladderneck, and/or bladder.

The surgical implant 70 is a woven mesh and has interstices between constituent fibers in which tissue in-growth can occur. The surgical implant 70 can be made of a wide variety of materials, and can be treated with a variety of therapeutic materials, which are discussed in more detail in the references cited herein.

Figure 5:
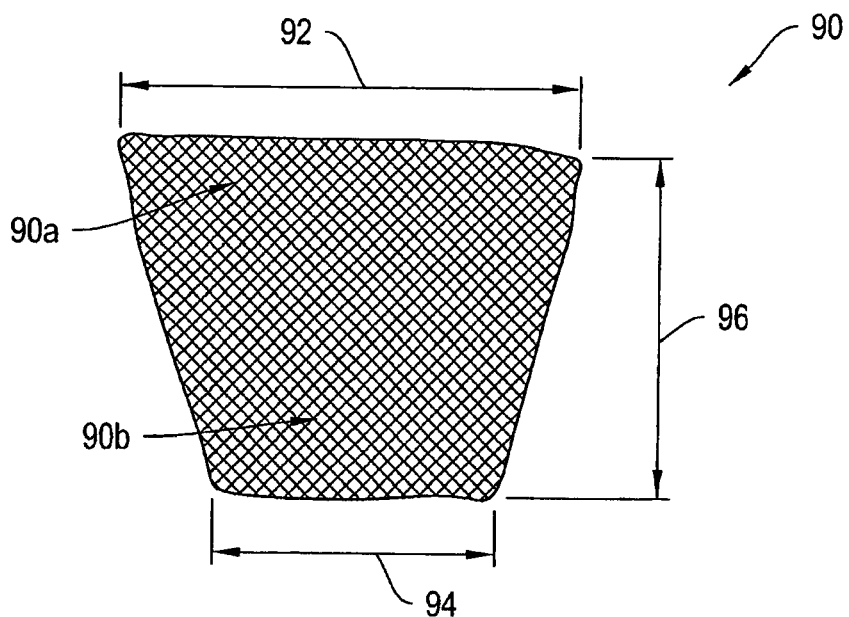
FIG. 5 shows a trapezoidal surgical implant sized and shaped for pelvic floor repair.

The implants can also be configured to have other desired shapes. FIG. 5 shows a trapezoidal shaped surgical implant 90 similar to the implant 30 of FIG. 2A, but without extension straps. The depicted surgical implant 90 has a posterior base length 92 of between about 8 cm and about 11 cm, an anterior base length 94 of between about 5 cm and about 7 cm, and an anterior-to-posterior length 96 of between about 5 cm and about 10 cm. The surgical implant 90 is shaped to have a wider posterior region 90a than anterior region 90b because the posterior region 90a of the surgical implant 90 supports larger posterior anatomical structures, such as the bladder, whereas the anterior region 90b of the implant 90 supports smaller anterior anatomical structures, such as the urethra and/or bladderneck.

Figure 6:
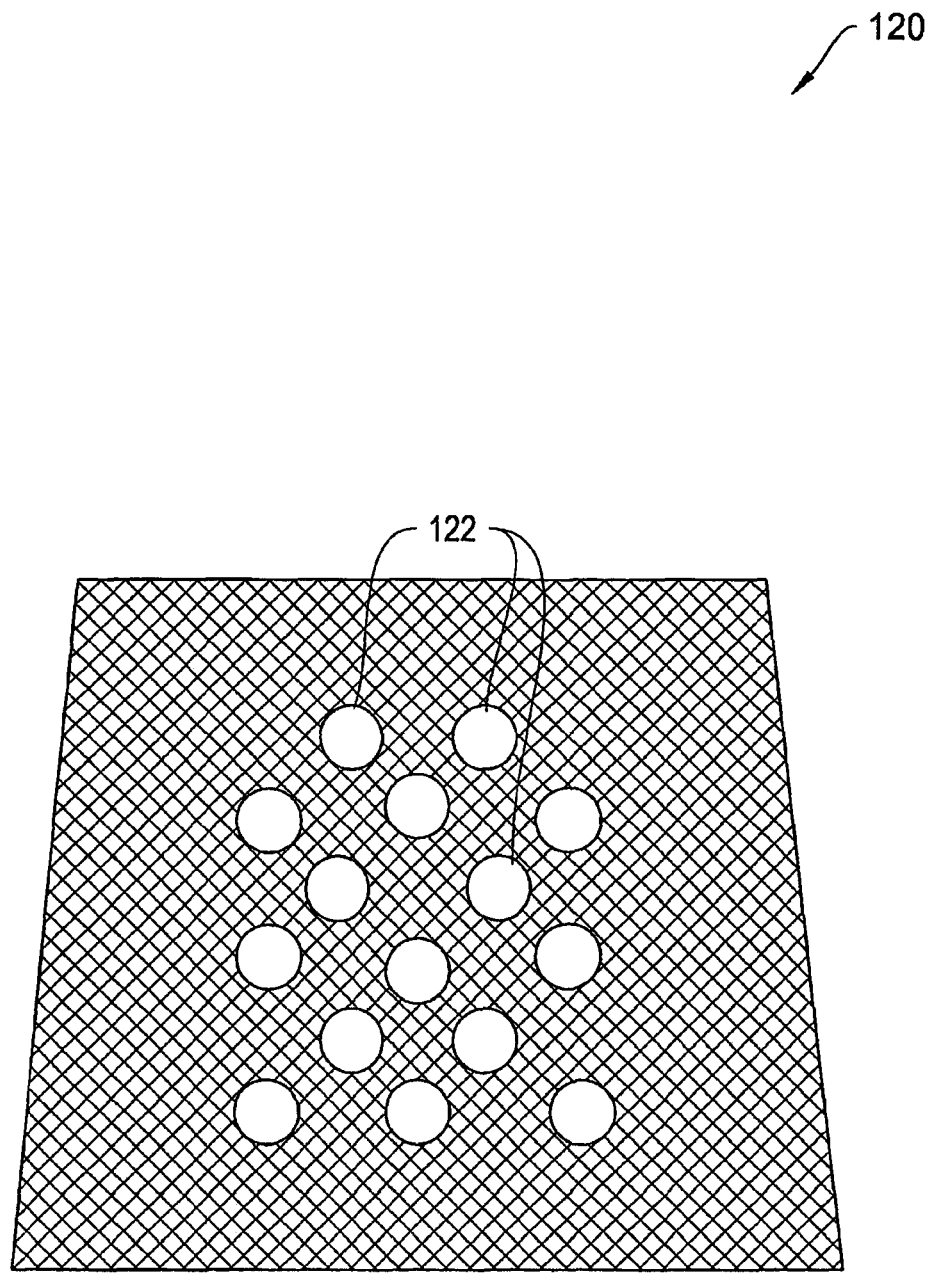
FIG. 6 shows a surgical implant that includes a plurality of apertures for promoting tissue in-growth.

As mentioned above, the surgical implants are generally made of mesh materials having interstices that promote tissue in-growth. FIG. 6 illustrates a surgical implant 120 that, additionally or alternatively, includes a plurality of apertures 122 that can be of varying sizes and that promote tissue ingrowth. This and other exemplary surgical implants are further discussed in U.S. Pat. No. 6,197,036, incorporated herein by reference in its entirety.

As noted, the mesh surgical implants described above may be woven. The implants may also be protected with a protective cover or sleeve, as described in U.S. patent application Ser. No. 11/202,554, the contents of which are incorporated by reference herein in their entirety, to help prevent the woven implants from unraveling, stretching, and/or otherwise becoming damaged by stresses applied to the implant during delivery. The sleeve covers and protects the implant during delivery of the implant through tissue, and is removed after delivery. Alternatively, the implant may be configured in nonwoven arrangements that prevent unraveling, stretching, and/or damaging during delivery and tensioning of the implant.

Figure 7A:
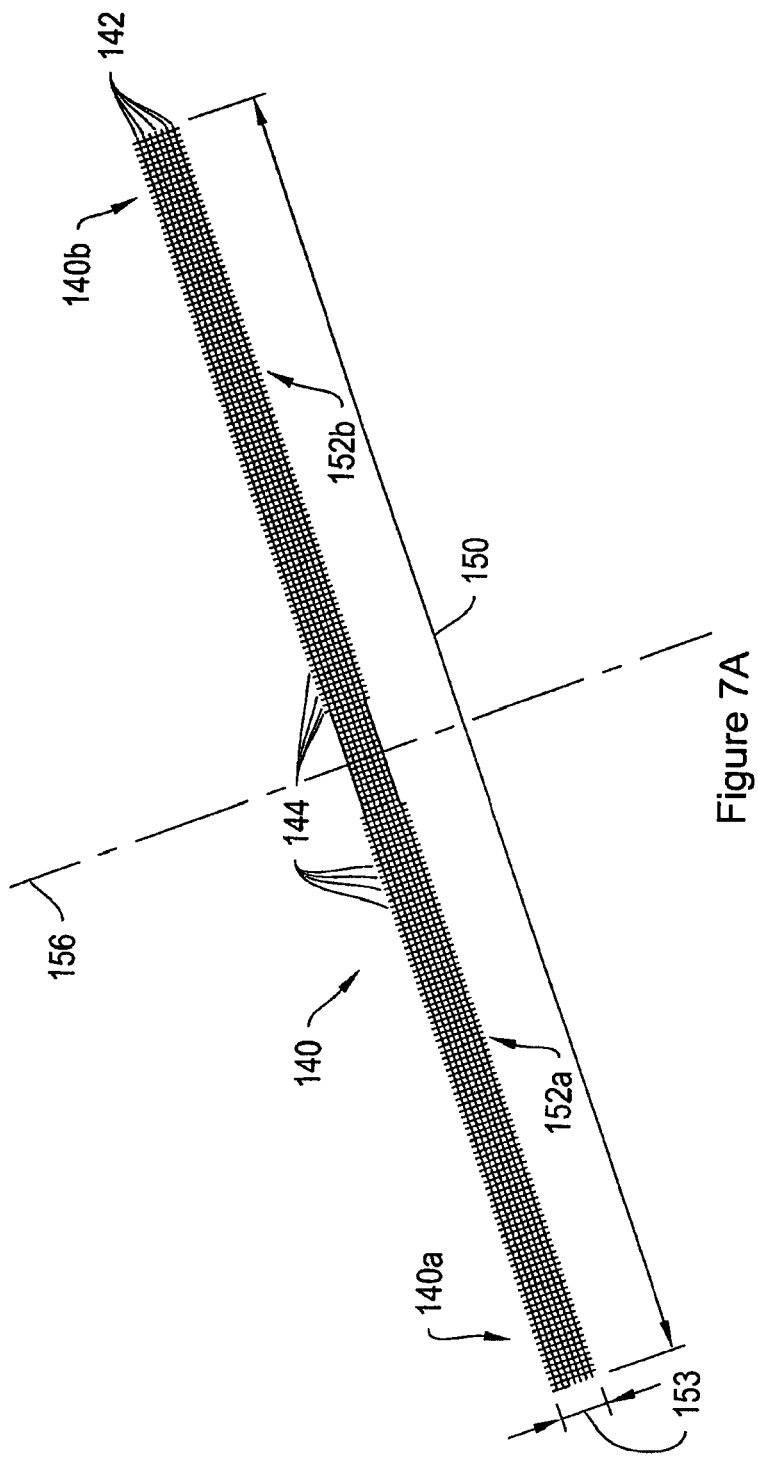
FIG. 7A shows a surgical implant having a first set of strands and a second set of strands attached at intersection points.

FIGS. 7A-14B illustrate various exemplary surgical implants constructed in such a nonwoven configuration. In particular, FIG. 7A shows a surgical implant 140 having a first end 140a, a second end 140b, a set of lateral strands 142, and a set of transverse strands 144, while FIG. 7B shows a close-up view of the implant 140. The implant 140 includes attachment points 146, wherein the lateral strands 142 intersect with and fuse or otherwise fixedly attach to the transverse strands 144, and openings 148 defined by the strands 142 and 144 and attachment points 146. The implant 140 can be sized to suit a particular application. For example, the depicted implant 140 has a lateral width 150 of between about 6 cm and about 11 cm to extend laterally between both of the patient's obturator foramen, and an anterior-to-posterior width 153 of between about 0.5 cm and about 2 cm to support the urethra and/or bladderneck.

Figure 7B:
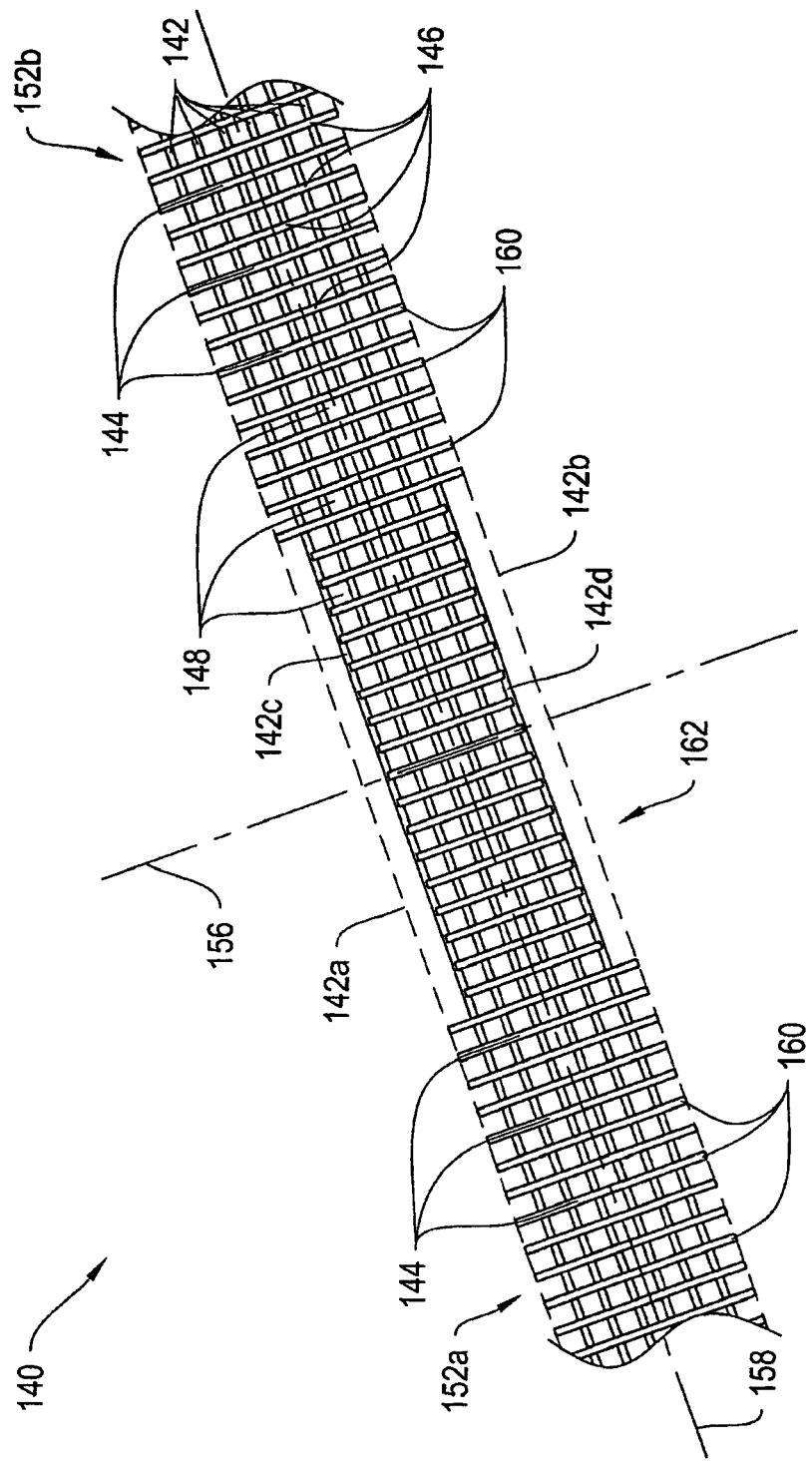
FIG. 7B shows a close-up view of the surgical implant of FIG. 7A.

As shown in FIG. 7B, in this illustrative embodiment, the lateral strands 142 are parallel to the longitudinal axis 158 of the implant, and the transverse strands 144 are substantially perpendicular to the lateral strands 142. The lateral strands 142 and the transverse strands 144 can be made of a wide variety of materials, including any of the biocompatible materials described herein or in the references cited herein. The lateral strands 142 and the transverse strands 144 may be made of monofilament fibers and/or multifilament fibers. The strands 142 and 144 may include different respective materials which provides, for example, different tension and/or elasticity along a longitudinal axis 158 compared to a perpendicular axis 156. In certain embodiments, the lateral strands 142 prevent the implant 140 from stretching laterally. In certain configurations, the lateral strands 142 and the transverse strands 144 have different respective colors. This may help an operator visually determine the orientation of the surgical implant 140 as he delivers and/or tensions the implant 140.

As mentioned above, the implant 140 includes attachment points 146 wherein the lateral strands 142 attach to and intersect with the transverse strands 144. In one embodiment, the attachment is formed by a biocompatible adhesive. Alternatively, the attachment is formed by fusing strands 142 and 144. In other embodiments, the attachment of the strands 142 and the strands 144 is formed by molding, stamping, and/or laser cutting.

The implant 140 also includes openings 148, defined by the strands 142 and 144, that promote tissue in-growth. The openings 148 may be of substantially similar size and shape. The depicted openings 148 are substantially rectangular, but they may have other shapes, and in certain embodiments are parallelogram-shaped. The openings 148 may also be of varying sizes and shapes to encourage the formation of varying tissue in-growth patterns along varying regions of the implant 140 according to a medical operator's preference.

The implants described herein are configured to be secured within soft tissues within the patient's retropubic space. In one aspect, the implant 140 includes tanged portions 152a and 152b, in which the transverse strands 144 extend beyond the span of the lateral strands 142 along the perpendicular axis 156, and a detanged portion 162 in which the length of the transverse strands 144 is substantially equal to the span of the lateral strands 142 along the perpendicular axis 156. As shown in FIG. 7B, the tanged portions 152a and 152b are formed from a plurality of tangs 160. The tangs 160 interact with surrounding tissue to resist, and optionally prevent, movement of the implant and thereby secure the implant 140 in place until tissue in-growth occurs through the openings 148. For example, tanged portions 152a and 152b may be placed directly within obturator foramen, thus securing the implant within the obturator foramen without requiring the use of anchors on the ends of the implant. Each of the tangs 160 may extend beyond a span of the lateral strands 142 by between about 0.5 mm and about 1 mm, by between about 1 mm and about 2 mm, by between about 2 mm and about 3 mm, by between about 3 mm and about 4 mm, by between about 4 mm and about 5 mm, or by between about 5 mm and about 1 cm. In certain embodiments, the tangs 160 are substantially rigid. For example, they may be made of monofilament or multifilament strands with sufficient rigidity to secure the implant 140 to target soft tissue regions without requiring the use of soft tissue anchors.

The implant 140 also includes a detanged portion 162 in which the length of the transverse strands 144 is substantially equal to the span of the lateral strands 142 along the perpendicular axis 156. The detanged portion 162 provides a wide support area for an anatomical structure. In certain implementations, an operator positions the detanged portion 162 under sensitive anatomical structures such as the urethra, bladderneck and/or bladder, while the tanged portions 152a secure the implant 140 in place, resulting in lessened irritation to the supported structures.

In one exemplary technique, a manufacturer forms the implant 140 by first attaching the strands 142 and 144 using one or more attachment methods described above, then forming the tanged portions 152a-b, and then forming the detanged portion 162. To form the tanged portions 152a-b, the manufacturer first manufactures the implant 140 with two additional lateral strands, depicted by dashed lines 142a and 142b, that are configured as the outermost strands in the set of lateral strands 142. The manufacturer then shortens the transverse strands 144 to the outer lateral strands 142a and 142b and removes the outer long strands 142a and 142b to expose the tangs 160. The tangs 160 are thus extremities of the transverse strands 144 that make up the implant 140, and the implant 144 and its strands 144 with tangs 160 form a unitary body. In one exemplary method, the transverse strands 144 are shortened by heat melting, and in others they are shortened by trimming or cutting. Next, to form the detanged portion 162, a manufacturer heat melts, cuts, trims, or otherwise shortens the transverse strands 144 to the outermost strands 142c and 142d of the remaining lateral strands 142. Because the strands 142 and 144 are individually attached, the strands 142 and 144 can be cut as desired without causing the implant to unravel.

Figure 8B:
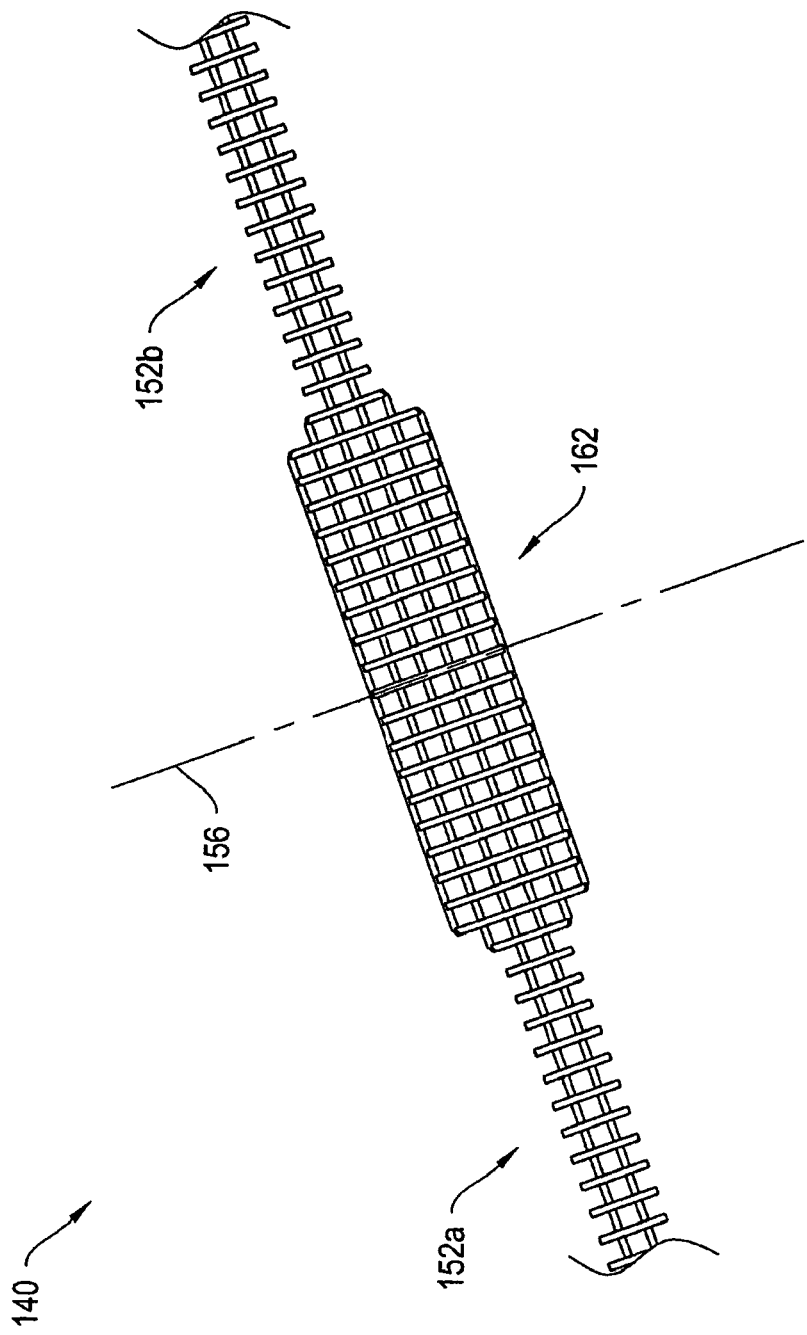
FIG. 8B shows a close-up view of the implant of FIG. 8A.

The tanged and untanged portions of an implant can be sized to achieve a desired anatomical fit and to reduce the level of invasiveness caused by implantation. FIGS. 8A and 8B show the implant 140 of FIGS. 7A and 7B with the tanged portions 152a and 152b having been narrowed along the perpendicular axis 156 by cutting or otherwise shortening the tanged portions 152a-b to reduce the delivery profile of the implant 140. A delivery profile refers to the maximum cross-sectional area of a passageway through the patient's anatomy that is required for delivery of the implant 140. The delivery profile may be effected by one or more of a number of factors, including the diameter of the delivery needles, shafts, and/or dilators, implant width, and protective sleeve width.

Smaller delivery profiles can be beneficial because they may result in less invasive implant delivery procedures. An implant having the smaller profile illustrated in FIGS. 8A-B may be delivered using a delivery device with smaller dimensions, such as a smaller shaft or needle, which may reduce trauma to the patient and damage less tissue. However, implants with larger profiles, such as implant 140 as shown in FIGS. 7A and 7B, may more securely anchor within the patient's anatomy and provide an operator with more control during delivery, and the operator can select an implant having a delivery profile that is suitable for the patient. The anterior-to-posterior width of the detanged portion 162 has not been narrowed and thus provides a wide support area for an anatomical structure.

Figure 9:
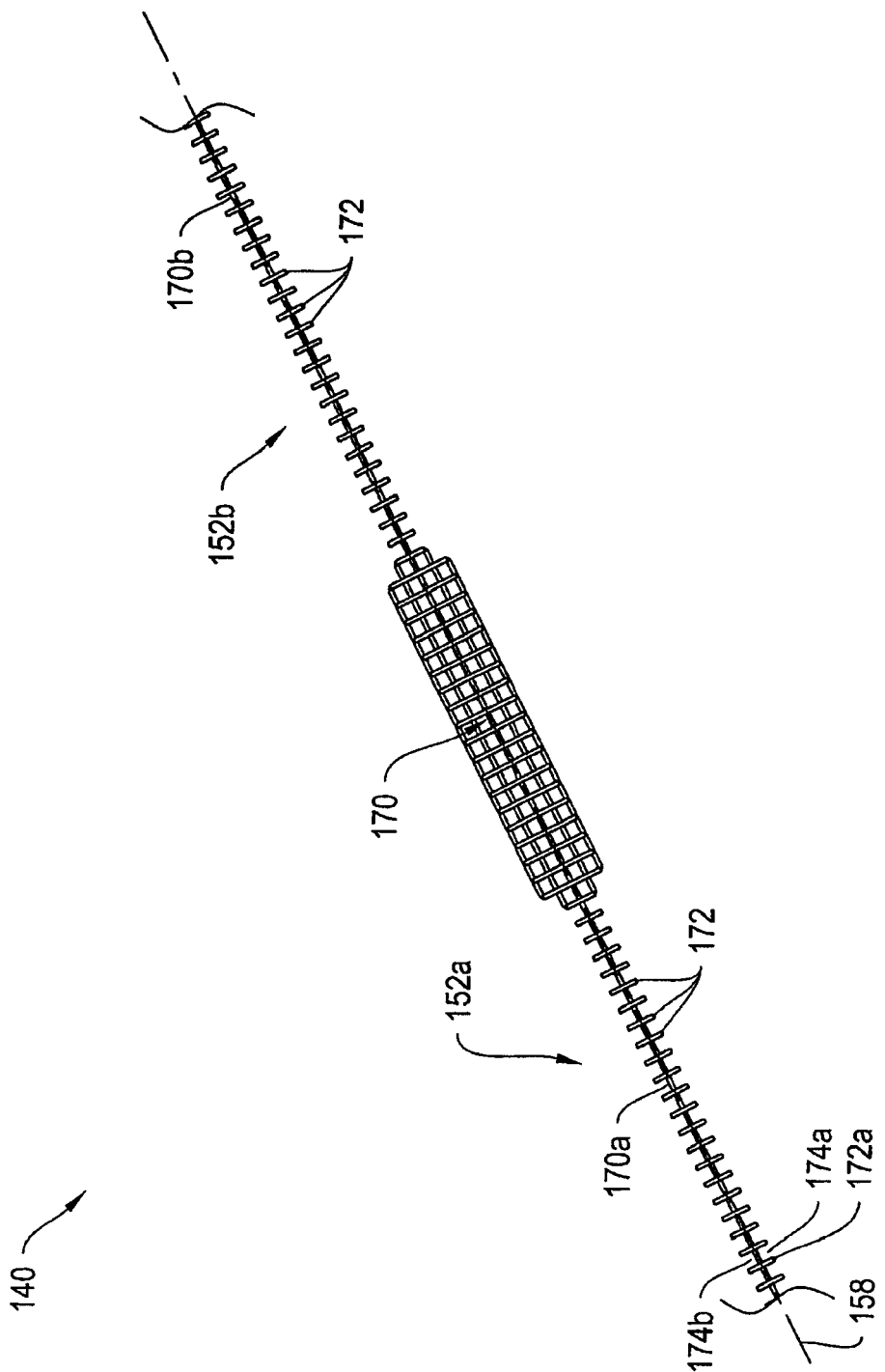
FIG. 9 shows an implant having tanged portions that include a single long strand and a plurality of short strands.

FIG. 9 shows an alternative implant embodiment with a still further reduced delivery profile. As shown each of the tanged portions 152a and 152b includes a single lateral strand 170 having end portions 170a and 170b. The tangs are formed from transverse strands 172 attached to the lateral strand 170 in a perpendicular orientation. In one exemplary application, an operator uses a delivery device with a fork-shaped tip to deliver, position, and/or adjust the placement of the implant 140. The operator interfits the prongs of the fork-shaped tip around the long strand near end portion 170a, for example, at regions 174a and 174b. The fork-shaped tip abuts one of the transverse strands 172a and the operator pulls or drags the implant 140 in a desired direction. In this embodiment, if one or both of the tanged portions 152a and 152b twist about the longitudinal axis 158 during delivery or placement, tissue in-growth in surrounding tissue regions may be substantially unaffected. Thus, the operator does not need to prevent twisting of the implant 140 during delivery.

Figure 10:
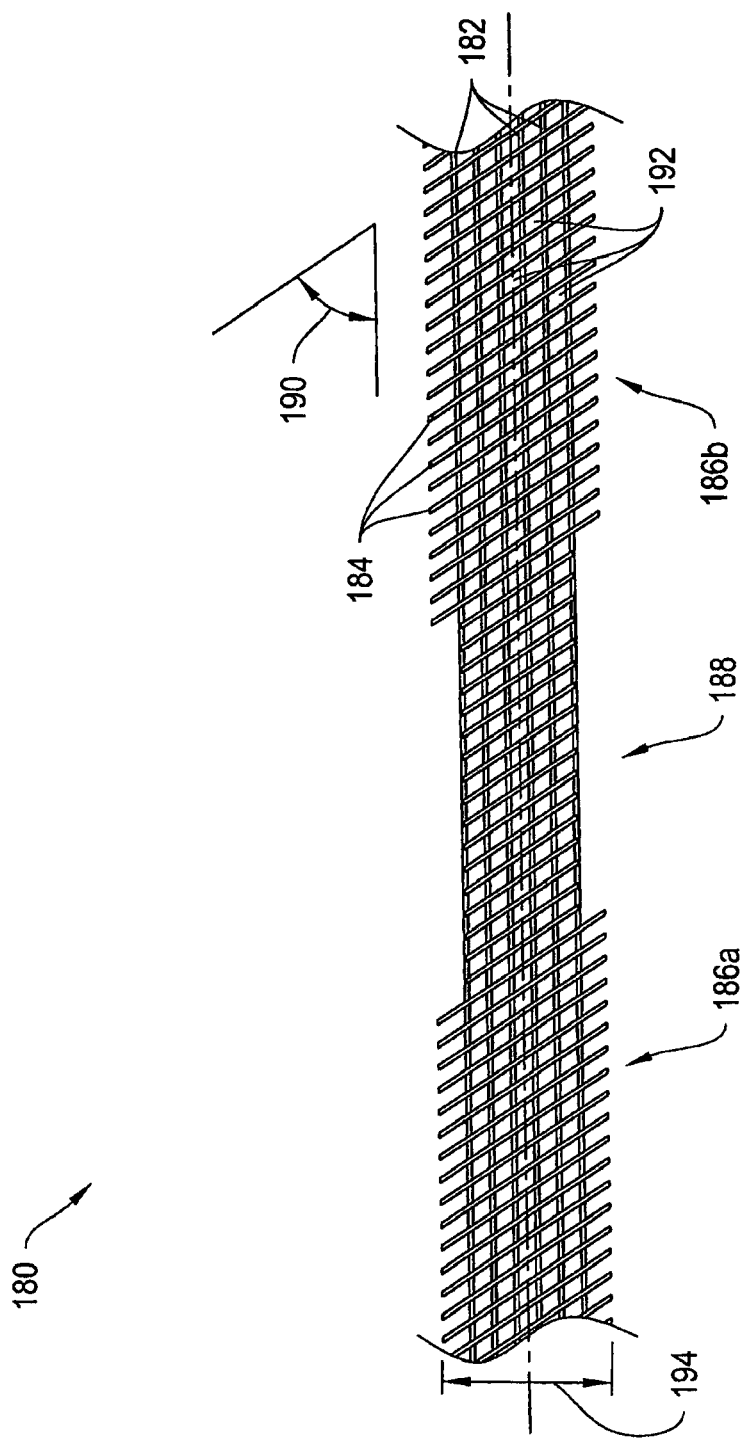
FIG. 10 shows an implant having long strands and short strands, wherein the long strands are oriented at a non-perpendicular angle with respect to the short strands.

The implants may also be shaped as needed to achieve desired elasticity and elongation properties. FIG. 10 shows an exemplary implant 180 having lateral strands 182 and transverse strands 184, tanged portions 186a and 186b and a non-tanged portion 188. The implant 180 is similar to implant 140 of FIG. 7A, except that the transverse strands 184 are oriented at an opposing and non-perpendicular angle 190 with respect to the lateral strands 182, so that the implant 180 includes openings 192 that are substantially diamond shaped. Orienting the transverse strands 184 in this manner allows the implant 180 to stretch in the transverse direction 194 without damaging the implant 60. More particularly, during implantation or use, when transverse stress or tension is applied along the anterior-to-posterior width 194, the transverse strands 184 shift and orient themselves perpendicularly to the lateral strands 182. This increases the anterior-to-posterior width 194 which allows the implant 180 to absorb the transverse stress without damaging the implant 180.

Figure 11A:
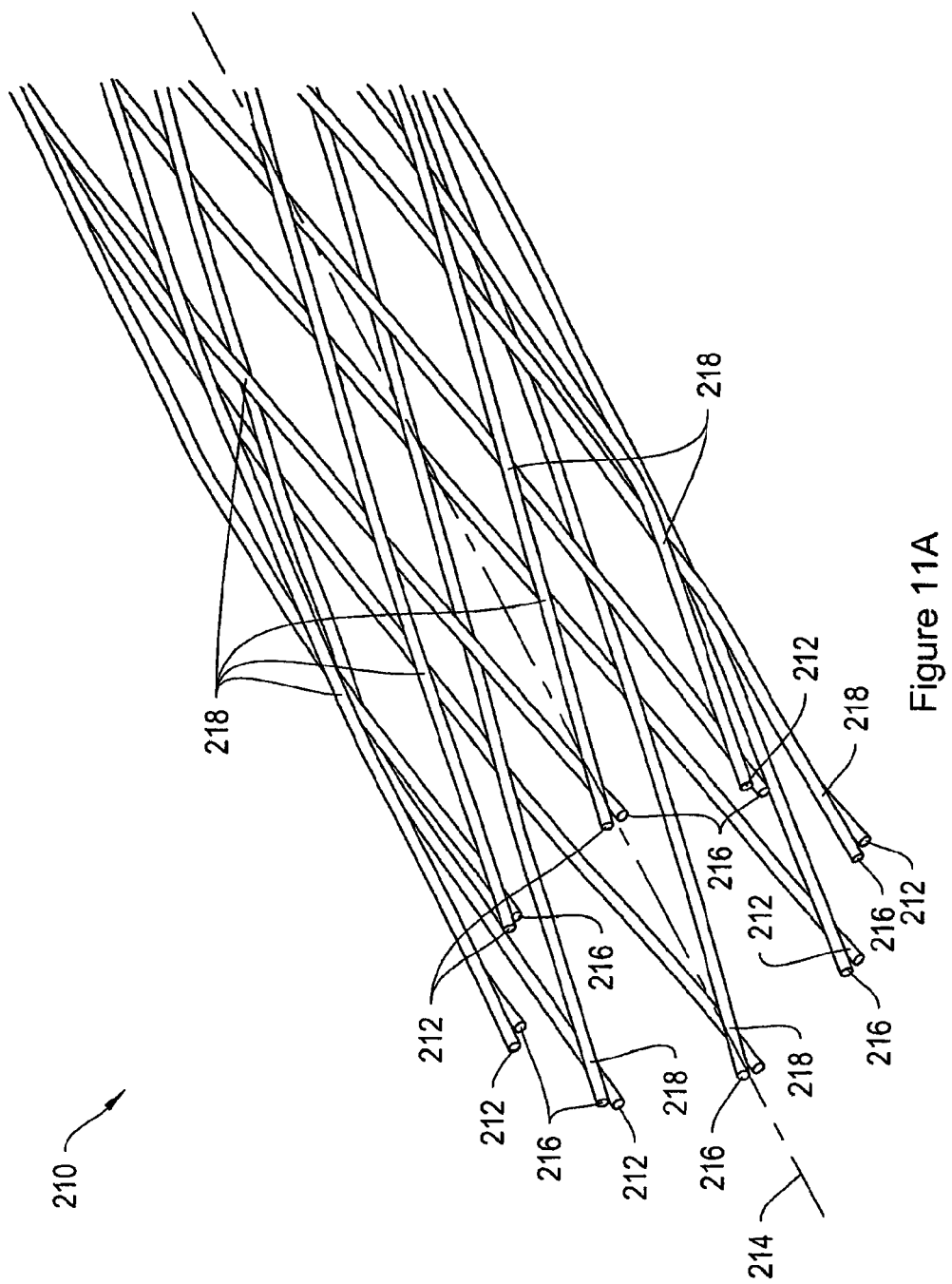
FIG. 11A illustrates an exemplary extrusion technique for constructing a surgical implant similar to the surgical implant of FIG. 10.
Figure 11B:
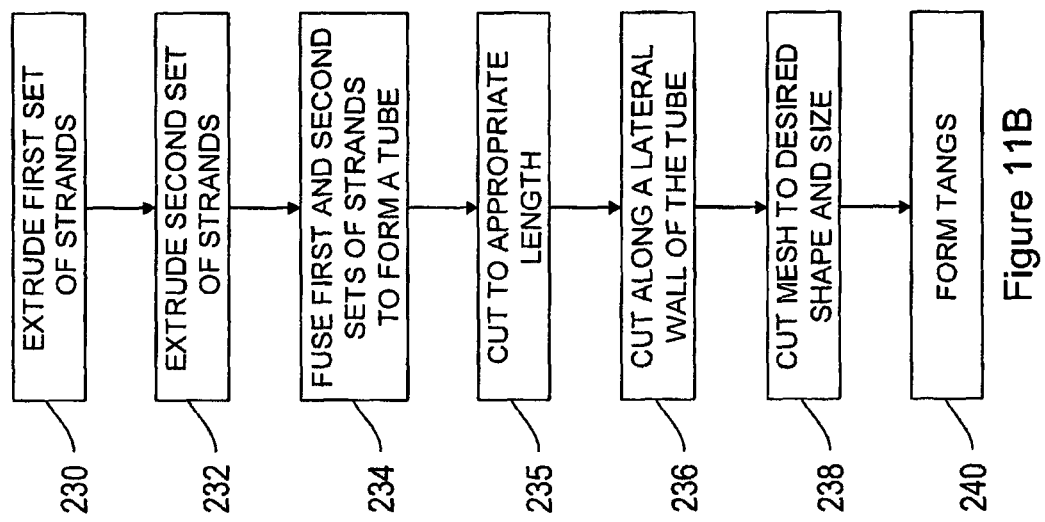
FIG. 11B is a block diagram showing the steps of the exemplary technique illustrated in FIG. 11A.

FIG. 11A illustrates an exemplary extrusion technique for constructing a surgical implant 210 similar to surgical implant 180 of FIG. 10, and FIG. 11B illustrates a block diagram of the technique. In the technique, a manufacturer first extrudes and fuses two sets of strands, and then cuts the resulting structure to size and shape the implant 210.

More particularly, a manufacturer first extrudes the first set of strands 212 (step 230) at a first angle with respect to the longitudinal axis 214. To do so, in one implementation, the manufacturer pushes and/or draws a feedstock of the implant material through an extrusion die that includes respective apertures for each of the first set of strands 212. The apertures are arranged in a circular configuration and oriented at the first angle with respect to the longitudinal axis 214 so that the first set of strands form a tube of parallel strands.

Next, the manufacturer extrudes a second set of strands 216 (step 232) at a second angle with respect to the longitudinal axis 214. To do so, in one implementation, the manufacturer pushes and/or draws a feedstock of the implant material through a second extrusion die that includes respective apertures for each of the second set of strands 216. These apertures are also arranged in a circular configuration and oriented at the second angle with respect to the longitudinal axis 214, so that the second set of strands forms a tube of parallel strands and intersects with the first set of strands 212 at a plurality of attachment points 218. The manufacturer then fuses the first set of strands 212 to the second set of strands 216 (step 234) at the attachment points 218, and thus forms a substantially continuous tube.

Next, the manufacturer cuts the implant 210 to an appropriate length along longitudinal axis 214 (step 235) and cuts the implant 210 longitudinally along one lateral wall of the tube (step 236) to open the tube into a flat shape. In certain embodiments, the cuts in the lateral wall allow the first set of strands 212 or the second set of strands 216 to be oriented parallel to the longitudinal axis 214 of the implant. This results in a configuration similar to that shown in FIG. 10, where the long strands 182 are parallel to the longitudinal axis 181 of the implant 180. As mentioned, such an orientation helps reduce stretching in the lateral direction during delivery of the implant 210. In other embodiments, the number of strands is increased or decreased to alter the diameter of the tubular shape in order to vary the size of the final configuration of the implant. Finally, the operator optionally cuts the implant to a desired size and shape (step 238), and optionally forms tangs as described above (step 240). The operator may also optionally couple the implant to one or more soft tissue anchors, as described herein.

Figure 12:
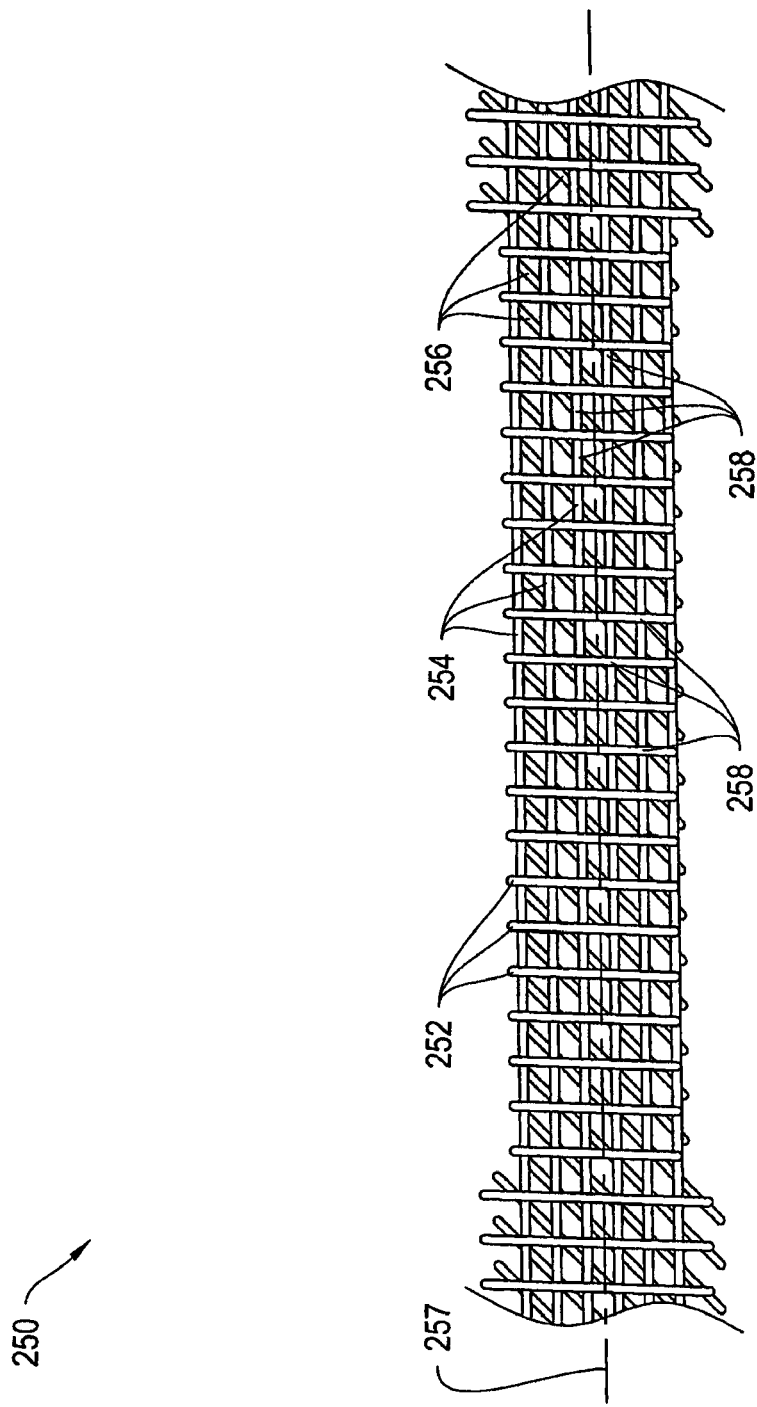
FIG. 12 illustrates a surgical implant having three sets of strands attached to each other at intersection points.

The implants described above in relation to FIGS. 7A-11B include two sets of strands, which in the illustrated embodiments include a first set of long strands and a second set of short strands. In alternative embodiments, additional sets of strands may be included to provide additional strength, tension, or elasticity properties. FIG. 12 illustrates a portion of any exemplary surgical implant 250 having three sets of strands—a first transverse set 252, a second lateral set 254, and a third cross-oriented set 256. The strands within each set are substantially parallel and in certain embodiments lie in different respective layers. Each layer is oriented at a different angle with respect to the longitudinal axis 257 and is fixedly attached to at least one other layer. As shown, the strands of each of sets 252, 254, and 256 attach to strands in one or both of the other two sets to form a plurality of intersection points 258 having strands of two or more of the sets fused, melted, or otherwise attached using methods discussed above.

Figure 13:
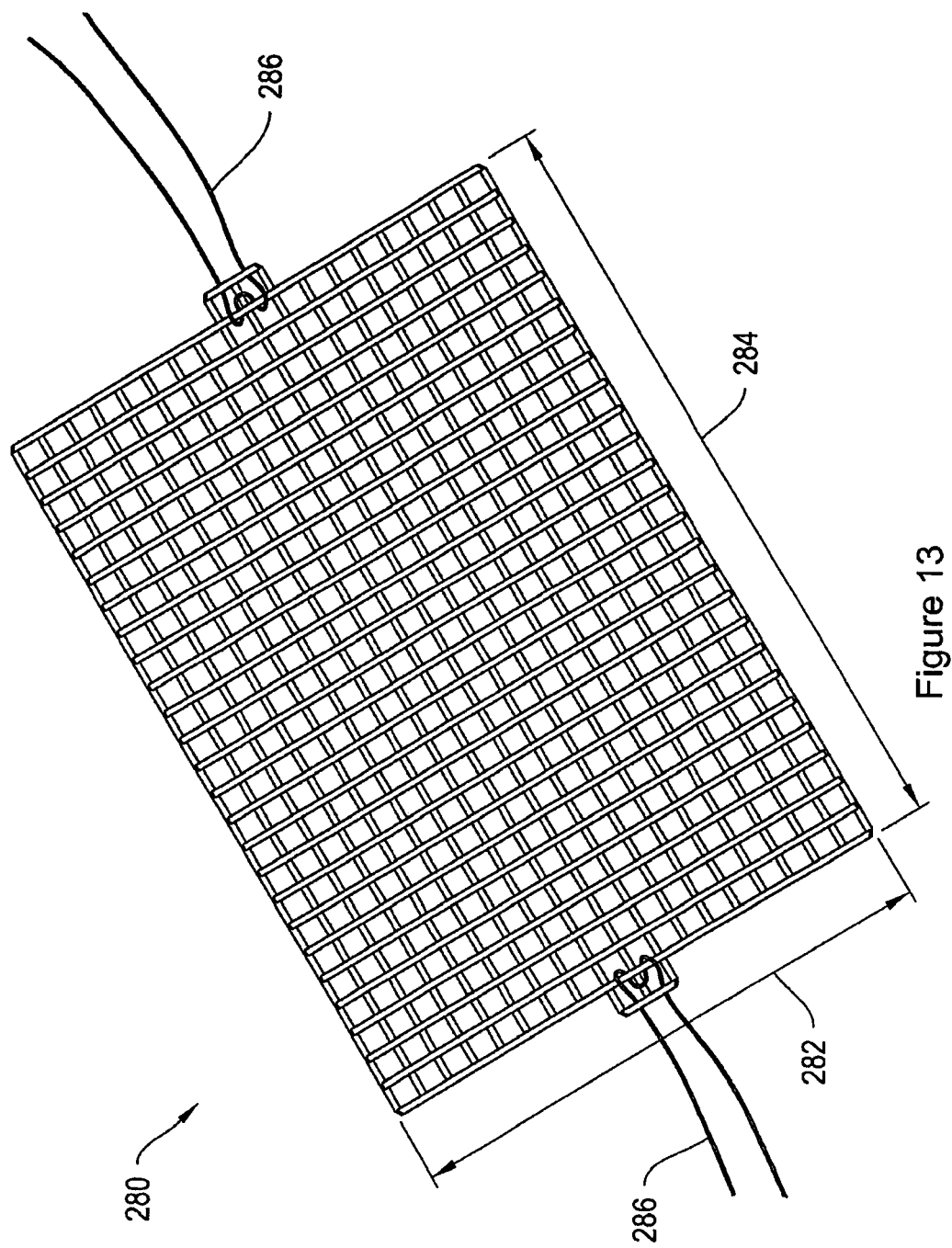
FIG. 13 illustrates a surgical implant manufactured using a similar method as in the surgical implant of FIG. 7A, but having a longer anterior-to-posterior length.

The implants described with respect to FIGS. 7A-12 are sized and shaped to support anatomical structures such as the urethra and/or the bladdemeck of the patient. Similarly constructed implants can be sized and shaped to support other anatomical structures and extend to other pelvic regions. FIG. 13 illustrates a surgical implant 280 constructed similar to the implant 140 of FIG. 7A, but sized and shaped similar to the implant 70 of FIG. 4. In particular, the implant 280 has a longer anterior-to-posterior length 282 than does implant 140, which allows the implant 280 to support posterior regions of the pelvic region, such as tissue regions posterior to the patient's bladdemeck and under the base of the patient's bladder.

Additionally, the depicted surgical implant 280 has a smaller lateral length 284 than the lateral length of the surgical implant 140 of FIG. 7A, such that the implant 280 does not span the full obturator-to-obturator length of the patient. Instead, as discussed below, the surgical implant 280 couples to soft tissue anchors that are spaced from the implant 280 by long filaments 286 which span the remainder of the obturator-to-obturator length when the soft tissue anchors anchor to respective obturator membranes. Although not shown, one or more of the edges of surgical implant 280 may include tangs as described above. In any of the exemplary embodiments, tangs are optional, particularly when soft tissue anchors are used to anchor the surgical implants to respective obturator membranes.

Figure 14A:
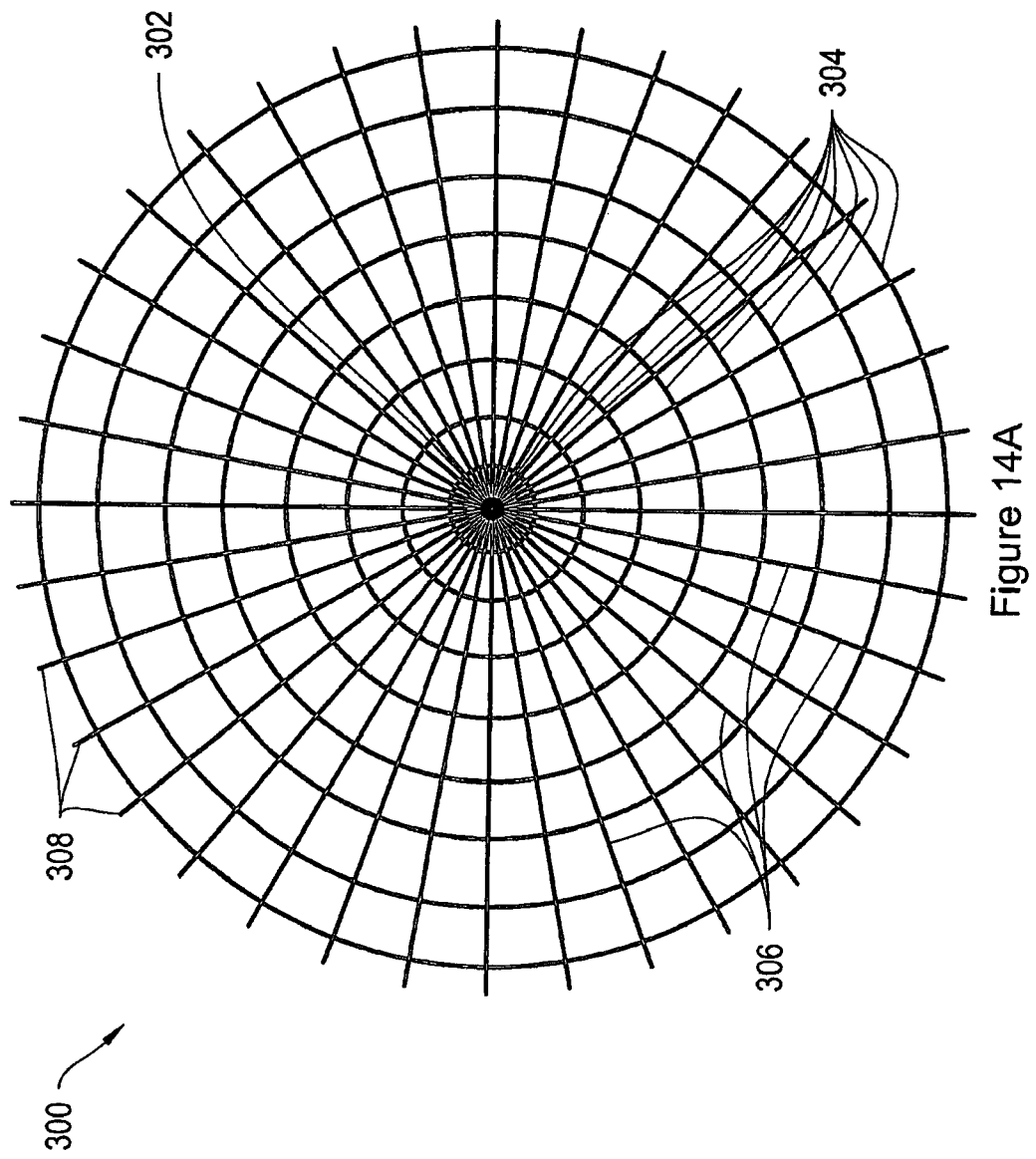
FIG. 14A illustrates a circular surgical implant including a first set of strands and a second set of strands attached at intersection points, wherein the implant is sized and shaped to extend to posterior regions of the pelvic floor and to support anatomical structures such as the bladder.
Figure 14B:
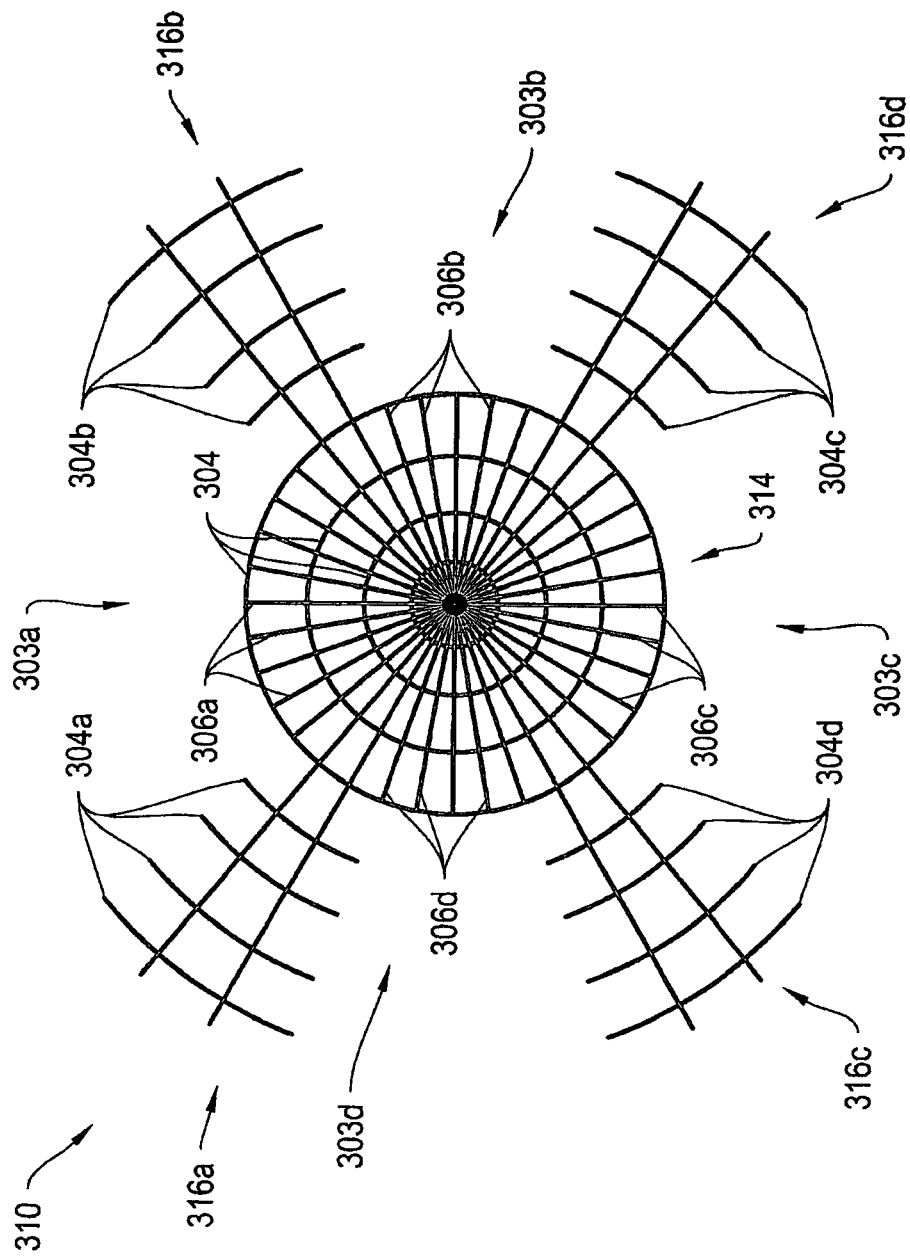
FIG. 14B shows the surgical implant of FIG. 14A after selective removal of portions of the surgical implant.

FIGS. 14A-B illustrate exemplary alternative surgical implants 300 and 310 that are sized and shaped to extend to posterior regions of the pelvic floor and to support anatomical structures such as the bladder. The implant 310 depicted in FIG. 14B is sized and shaped similar to the implant 60 of FIG. 3, but is manufactured according to the non-woven configuration described above in connection with FIGS. 7A-12. The illustrative implant 300 in FIG. 14A is circular and has a center 302, a first set of strands 304 formed as concentric circles of increasing radii about center 302, and a second set of strands 306 that extend radially from the center 302. The implant 300 includes tangs 308, but in alternative embodiments, portions of the implant may be detanged as described above.

In one exemplary manufacturing technique, a manufacturer selectively removes portions of the surgical implant 300 depicted in FIG. 14A to construct the surgical implant 310 of FIG. 14B. In particular, portions 303a-303d are removed by cutting, trimming, melting, laser cutting, or using other like methods. The removal of the portions 303a-303d shortens some of the radial strands 306a-306d and, optionally leaves them detanged. Similarly, the removal of portions 303a-303d leaves the concentric circular strands 304 in segments 304a-304d, which are depicted as being tanged. The resulting implant 310 thus includes a central untanged portion 314 with multiple radially extending tanged extensions 316a-d. The depicted central untanged portion 314 is circular for supporting various anatomical structures including, for example, the base of the bladder. The radially extending tanged portions 316a-d can extend to and anchor to respective obturator membranes either alone or in combination with soft tissue anchors, as will be discussed below.

The implants discussed above generally lie flat when not in use. However, in one aspect, the implants described herein may be pre-shaped to curve and fit around desired anatomical locations. For example, FIG. 15A shows an implant 320 that is sized and pre-shaped to fit under and support a urethra and/or a bladderneck. The implant 320 includes an indented portion 322 that is designed to interfit under the bladderneck and/or the urethra, to impede the implant 320 from exerting excessive stress on the bladderneck and/or urethra.

In one exemplary technique, the indented portion 322 is formed by gathering and compressing the portion 322 of the implant 320 using a clip 324 shown in FIG. 15B that is' aligned along the anterior-to-posterior direction 328 of the implant 320. In particular, the operator squeezes together levers 326a and 326b and opens the clip 324, then places the portion 322 of the implant 320 in the clip 324, releases the levers 326a and 326b to close the clip, and then folds the ends 320a and 320b over respective levers 326a and 326b. After waiting for a sufficient period of time for the implant 320 to maintain its folded configuration upon removal of the clip 324, the operator opens the clip and releases the implant 320, which is then shaped as illustrated in FIG. 15A.

Larger pelvic floor implants described above, including those sized and shaped to extend to and support a patient's bladder, can be similarly pre-shaped using larger clips 324, or by using multiple clips 324 or multiple uses of a single clip 324 at various locations along the implant 320. The depicted indented portion 322 extends in the anterior-to-posterior direction 328, but in other implementations the indented portion 322 may also extend in a lateral direction 330. This can be done by, after forming the indented portion 322 as described above, gathering and compressing a portion of the implant 320 with the clip 324 aligned along the lateral direction 330 of the implant 320.

The implants described above can be constructed from a variety of materials. There are many possible mesh materials, and the implant may, in the alternative or in combination, be made of other types of materials. Exemplary mesh materials include, for example, synthetic materials, natural materials (e.g., biological) or a combination thereof. The mesh may be fabricated from any of a number of biocompatible materials, such as nylon, silicone, polyethylene, polyester, polyethylene, polyimide, polyurethane, polypropylene, fluoropolymers, copolymers thereof, combinations thereof, or other suitable synthetic material(s). The material may be, for example, a biodegradable synthetic material. The term "biodegradable," as used herein, refers to the property of a material that dissolves in the body. Such materials may also be absorbed into the body, i.e., bioabsorbable.

Suitable bioabsorbable synthetic materials include, without limitation, polylactic acid (PLA), polyglycolic acid (PGA), poly-L-lactic acid (PLLA), human dermis and decellularized animal tissue. Human tissues may be derived, for example, from human cadaveric or engineered human tissue. Animal tissues may be derived, for example, from porcine, ovine, bovine, and equine tissue sources. The material may be an omnidirectional material, a material that has equivalent tensile strength from any direction, such as pericardium or dermis. Alternatively, the material may be an oriented material, a material that has a single direction where the tensile strength of the material is the highest. Oriented materials may include rectus fascia and/or facia lata, as well as oriented synthetic materials.

Exemplary biodegradable polymers, which may be used to form the tubular mesh 100, in addition to those listed above, include, without limitation, polylactic acid, polyglycolic acid and copolymers and mixtures thereof, such as poly(L-lactide) (PLLA), poly(D,L-lactide) (PLA), polyglycolic acid [polyglycolide (PGA)], poly(L-lactide-co-D,L-lactide) (PLLA/PLA), poly(Llactide-co-glycolide) (PLLA/PGA), poly(D,L-lactide-co-glycolide) (PLA/PGA), poly(glycolideco-trimethylene carbonate) (PGA/PTMC), poly(D,L-lactide-co-caprolactone) (PLA/PCL), and poly(glycolide-co-caprolactone) (PGA/PCL); polyethylene oxide (PEO); polydioxanone (PDS); polypropylene fumarate; polydepsipeptides, poly(ethyl glutamate-co-glutamic acid), poly(ter-tbutyloxy-carbonylmethyl glutamate); polycaprolactone (PCL), poly(hydroxy butyrate), polycaprolactone co-butylacrylate, polyhydroxybutyrate (PHBT) and copolymers of polyhydroxybutyrate; polyphosphazenes, polyphosphate ester); maleic anhydride copolymers, polyiminocarbonates, poly[(97.5% dimethyl-trimethylene carbonate)-co-(2.5% trimethylene carbonate)], cyanoacrylate, hydroxypropylmethylcellulose; polysaccharides, such as hyaluronic acid, chitosan, alginates and regenerate cellulose; poly(amino acid) and proteins, such as gelatin and collagen; and mixtures and copolymers thereof.

The systems, devices and methods described herein may be combined with other techniques for treating UI and/or pelvic floor disorders. For example, while the implants described herein are suitable for use in the single vaginal incision procedure, such implants may also be used in multi-incision procedures such as those described in U.S. Patent Publications 2005/0245787, 2005/0250977, 2005/0075660, U.S. Pat. No. 6,911,003, and other systems. In certain implementations, the meshes used to support the urethra and/or pelvic organs may, either as a whole or on a fiber-by-fiber basis, include an agent for release into the patient's tissues. One illustrative agent is a tissue growth factor that promotes, when applied to the patient's tissues in a pharmaceutically acceptable amount, well-organized collagenous tissue growth, such as scar tissue growth, preferably, in large quantities. According to one feature, the agent may or may not block or delay the dissolvability of the biodegradable materials. This may be controlled by selecting differing methods for loading the agent onto the implant. The tissue growth factor may include natural and/or recombinant proteins for stimulating a tissue response so that collagenous tissue such as scar tissue growth is enhanced. Exemplary growth factors that may be used include, but are not limited to, platelet-derived growth factor (PDGF), fibroblast growth factor (FGF), transforming growth factor-beta (TGF-beta), vascular endothelium growth factor (VEGF), Activin/TGF and sex steroid, bone marrow growth factor, growth hormone, Insulin-like growth factor 1, and combinations thereof. The agent may also include a hormone, including but not limited to estrogen, steroid hormones, and other hormones to promote growth of appropriate collagenous tissue such as scar tissue. The agent may also include stem cells or other suitable cells derived from the host patient. These cells may be fibroblast, myoblast, or other progenitor cells to mature into appropriate tissues. Besides applying active pharmaceutical agents, passive agents may be applied to promote tissue in-growth. For example, titanium sputtering or chrome sputtering can be used.

In various illustrative embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methyolprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as bumadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as 6-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papaveretum, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof Exemplary non-narcotic analgesic agents that may be combined with the implants of the invention include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, pbromoacetanilide, 5-bromosalicylic acid acetate, bucetin, bufexamac, bumadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocaine hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

Having described various surgical implants sized, shaped, and constructed for UI and/or pelvic floor repair, and exemplary methods of construction, we next describe soft tissue anchors that may optionally be used to secure the surgical implants to a desired anatomical location, such as obturator membranes, and methods for coupling the soft tissue anchors to the surgical implants. In use, as mentioned above, the surgical implants are inserted and positioned in a desired location within the pelvic region of the patient through a single incision in the patient's vaginal wall and then anchored to soft tissue regions such as obturator membranes.

In general, soft tissue anchors are biocompatible structures that are fixed to or interoperationally connected to an implant and are adjusted to anchor to patient's pelvic tissue. In certain embodiments, the soft tissue anchors are sling housings directly formed and/or fitted as end terminations around ends of the implant, and in others the soft tissue anchors and the implant are separate elements that can be assembled to form an implant assembly. Moreover, the anchors may be directly coupled to a surgical implant, or indirectly coupled to the implant via, for example, filaments or rings that space the anchors away from the surgical implant. The soft tissue anchors may adjustably couple to the surgical implant to allow an operator to tension the implant after anchoring in the patient. The soft tissue anchors can include barbs that anchor to the obturator membrane, or can be smooth, in which case the operator positions the anchor to act as a mechanical stop and prevent disengagement from the obturator membrane. The soft tissue anchors may also be bioabsorbable and absorb into surrounding tissue after being implanted into the pelvic region of the patient.

Figure 16A:
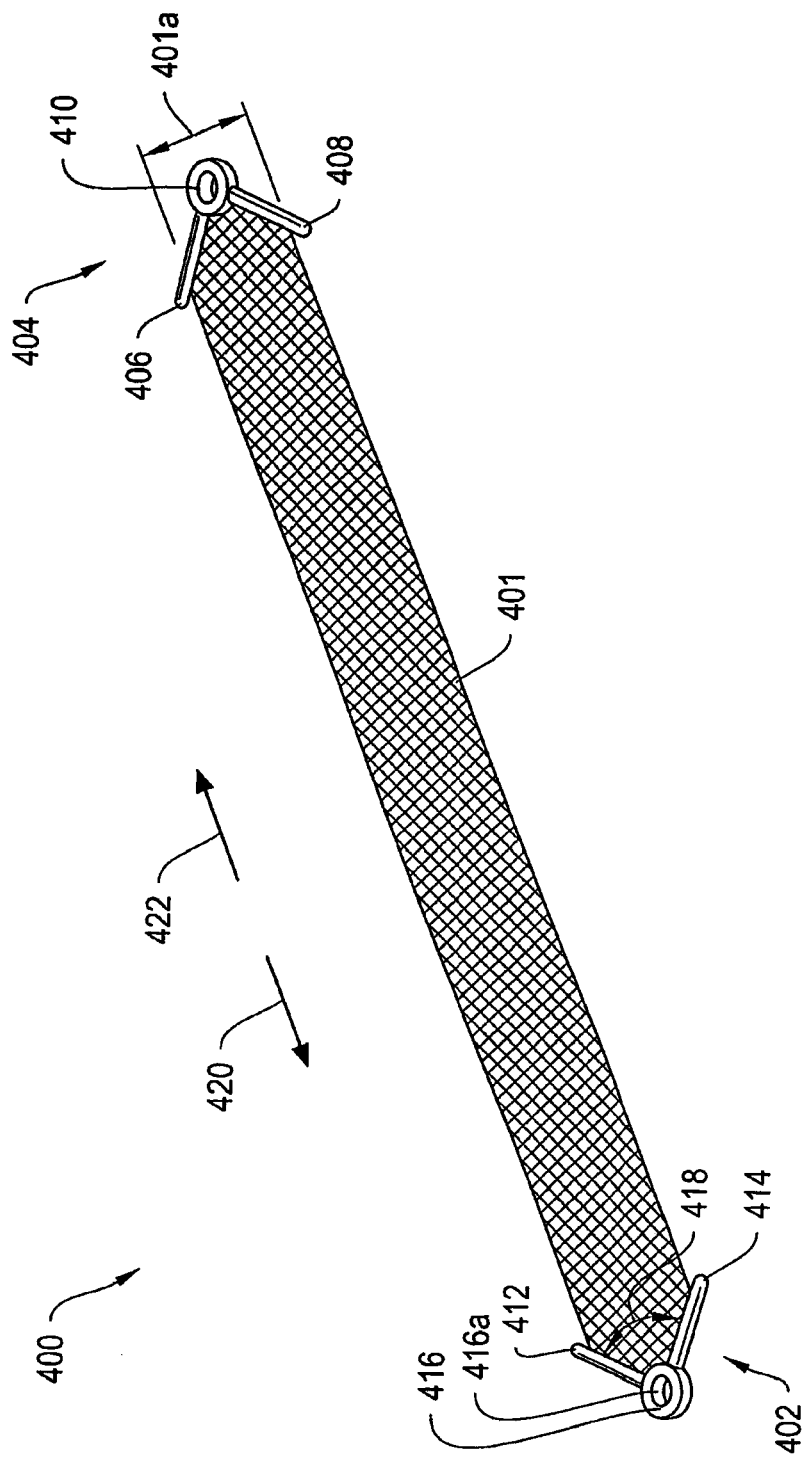
FIG. 16A shows a sling assembly including an implant and end terminations for associating the implant to a delivery device and for anchoring the implant to soft tissue.
Figure 16B:
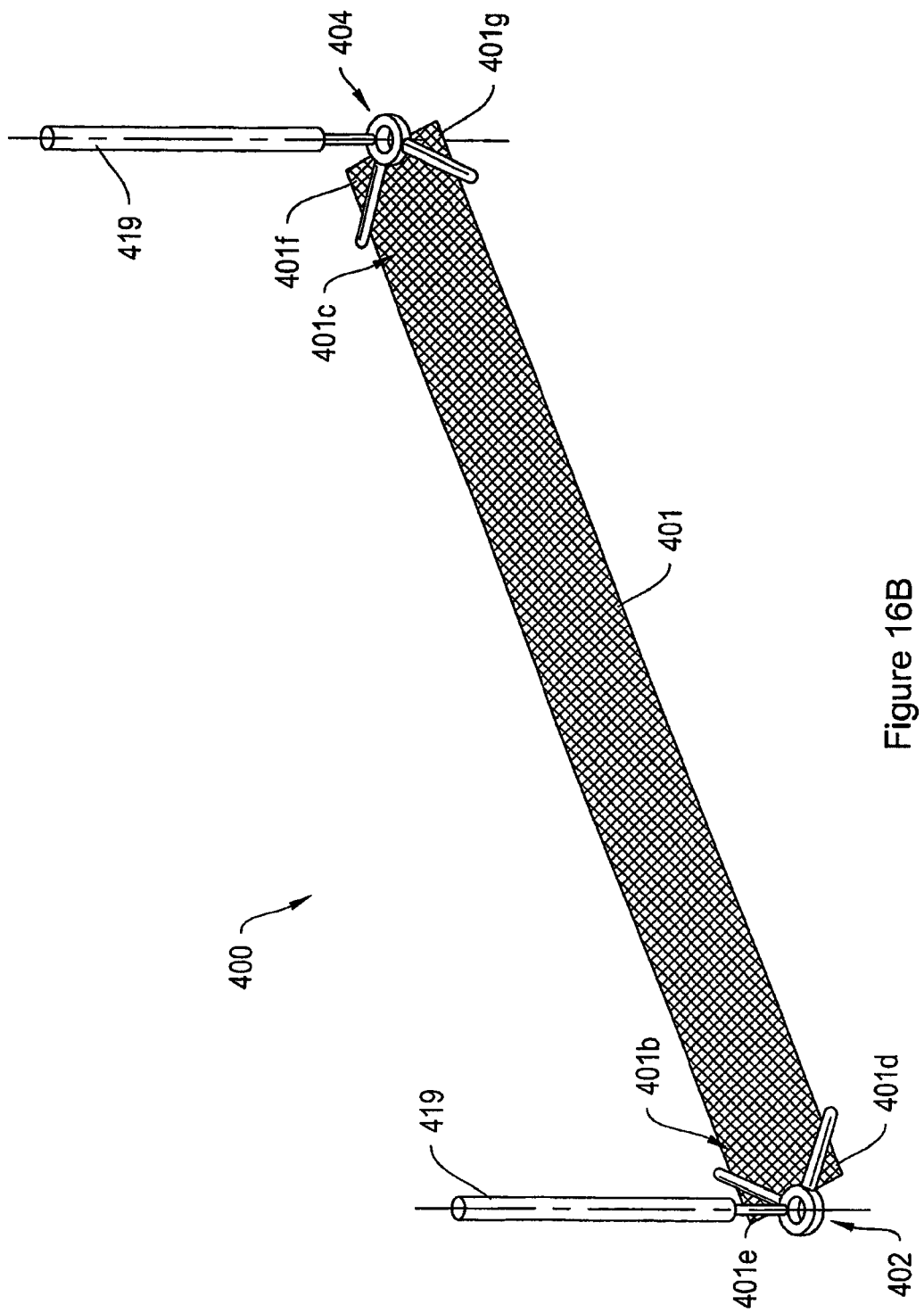
FIG. 16B illustrates an exemplary manufacturing technique of the implant of FIG. 16A.

FIGS. 16A-16C depict an implant assembly 400 having soft tissue anchors that are configured as housings around ends of a surgical implant 401 to anchor the implant and couple the implant with delivery devices.

More particularly as shown in FIG. 16A, the implant assembly 400 includes housings 402 and 404 which are end terminations formed and/or fitted around the end of the mesh implant 401 that taper away from the end of the implant 401 about which they are formed and/or fitted. The end termination 402 includes a ring or aperture 416 and first and second legs 412 and 414 that extend radially from the aperture 416. The aperture 416 is sized and shaped to engage with a delivery device, such as, for example, the distal end of a shaft, needle or dilator of any of the delivery devices described below. The assembly 400 also includes an end termination 404 that is similar to end termination 402. In particular, end termination 404 includes legs 406 and 408 extending radially from aperture 410. In operation, an operator places the aperture 416 (or 410) over the tip of a delivery device shaft and slides the aperture 416 down the tip until the aperture 416 abuts against a step, shoulder, or other stopping mechanism, as will be discussed in more detail below. The apertures 410 and 416 include inner surfaces 410a and 416a that, in certain embodiments, are tapered to inter-fit with the tip of a delivery device.

The depicted apertures 410 and 416 are coplanar with the implant 401. As a result, the implant assembly 400 has a low delivery profile. As mentioned above, a delivery profile refers to the maximum cross-sectional area of a passageway through the patient's anatomy that is required for placement of the implant, and smaller delivery profiles are beneficial at least in part because they may reduce tissue damage during implant delivery. Moreover, apertures 410 and 416 may be any shape, including square, triangular, oval, or other preferred shapes. The apertures 410 and 416 may also be any size, and in particular may be configured to couple with shafts or needles of varying dimensions.

The legs on the end termination 402 and 404 are sized and shaped to engage with and attach to the implant 401 to help anchor the implant 401 inside the patient. More particularly, referring to the end termination 402, the legs 412 and 414 extend radially from the respective aperture 416 and adjoin at angle 418. In certain embodiments, the end termination 402 is flexible such that the angle 418 can be increased or decreased upon application of appropriate mechanical pressure. By way of example, if the implant 401 passes through tissue in a forward direction 420, the legs 412 and 414 interact with the tissue to reduce the angle 418. If the implant 401 passes through tissue in a retrograde direction 422, the legs 412 and 414 are pushed outward by the tissue to increase the angle 418. The varying angle 418 thus facilitates movement of the implant 401 in the forward direction 420, and impedes movement of the mesh strap 401 in the retrograde direction 422. In certain embodiments, the angle 418 can vary from between about 0 degrees to about 90 degrees, and in other embodiments can vary to more than about 90 degrees. The angle 418 formed between the legs 412 and 414 can vary, as can the flexibility of the end termination 402. These properties are generally chosen to suit the particular delivery path and location for anchoring the implant, as well as the condition being treated.

Additionally, the V-shaped configuration of legs 412 and 414 acts to engage with patient tissue to resist removal once the implant assembly 400 is implanted. The depicted legs 412 and 414 extend beyond the width 401a of implant 401 to provide additional engagement with tissue, but in other illustrative embodiments may be of any length, and may not extend beyond the width 401 a of the implant 401. The features described herein with regard to end termination 402 may also apply to end termination 404.

The end termination may be connected to the implant by gluing, stapling, soldering, molding, or other methods. FIG. 16B shows an embodiment in which the end terminations 402 and 404 are molded to the implant 401. In an exemplary manufacturing technique, a manufacturer inserts an end 401b of the implant 401 into a mold (not shown) that has passages or cavities shaped like end termination 402 (i.e., including cavities shaped like ring 416 and legs 412 and 414). Next, the manufacturer injects a curable material, such as a curable biocompatible plastic, into the mold. After the curable material cures, the manufacturer decouples the mold and the implant 401, and then trims, melts, or otherwise removes excess molding material 419. The process is repeated for the other side 401c of the implant 401 to form end termination 404, the manufacturer then trims, melts, or otherwise removes excess mesh corners 401d, 401e, 401f, and 401g of the implant 401.

Figure 17:
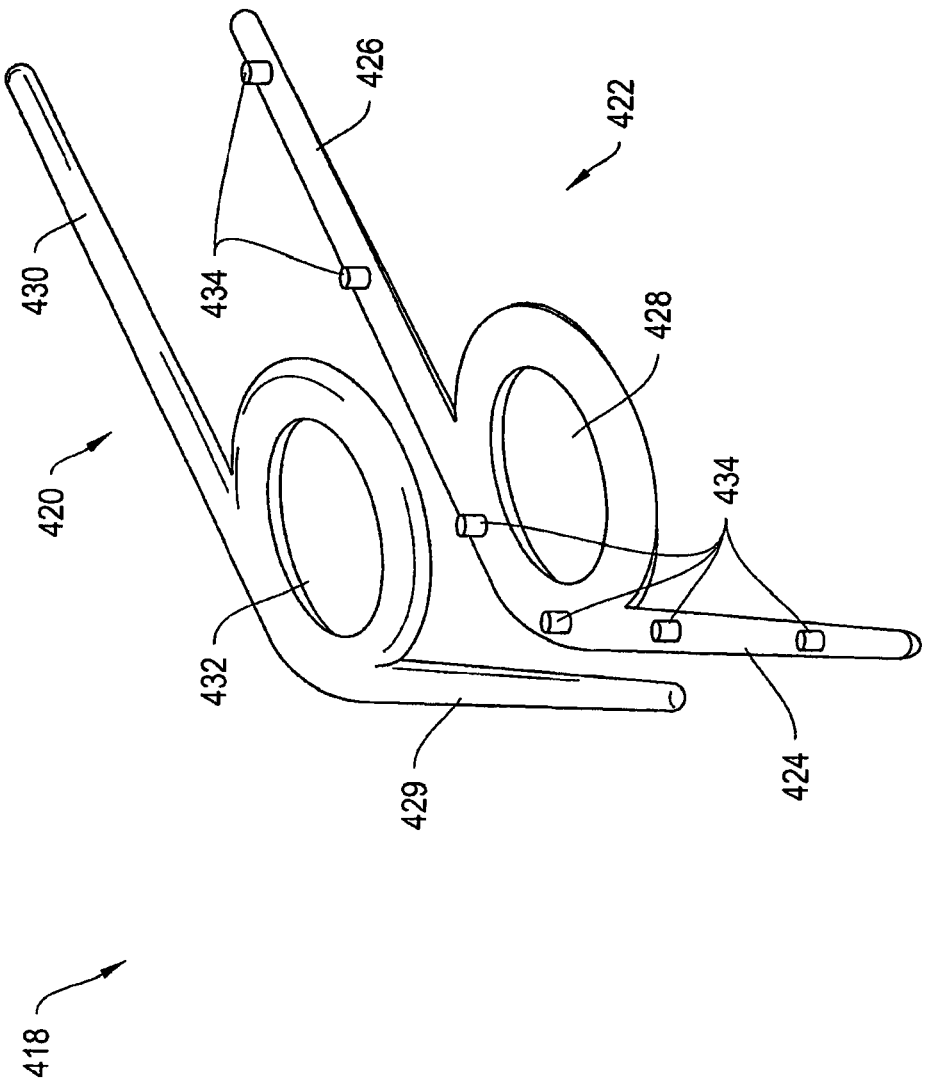
FIG. 17 shows an alternative configuration for an end termination having a top piece and a bottom piece.

FIG. 17 illustrates an end termination similar to the end terminations 402 and 404, but which does not need to be molded directly on an implant. This end termination includes a top piece 420 and a bottom piece 422. The bottom piece 422 includes two legs 424 and 426 that form a V-shape and an aperture 428 located between the V-shaped legs 424 and 426. The top piece 420 is shaped to align with the bottom piece 422, and in particular includes two legs 429 and 430 that form a V-shape and an aperture 432 located between the V-shaped legs 429 and 430. The top piece 420 further includes a plurality of apertures or cavities (not shown) that align with a plurality of projections 434 that are designed to interfit within the apertures or cavities. In operation, a manufacturer secures an implant 401 between the top piece 420 and the bottom piece 422 by disposing an end of the implant 401b between the top piece 420 and the bottom piece 422. The projections 434 pass through interstitial spaces between filaments of the implant 401 and snap-fit into the corresponding apertures or cavities (not shown) in the top piece 420. In addition to or as an alternative to using the projections 434 and the corresponding apertures or cavities, a manufacturer may secure the top piece 420 and the bottom piece 422 by gluing, heat-bonding, molding, or otherwise attaching the top piece 420 and the bottom piece 422 to each other and/or to the implant 401.

Figure 18:
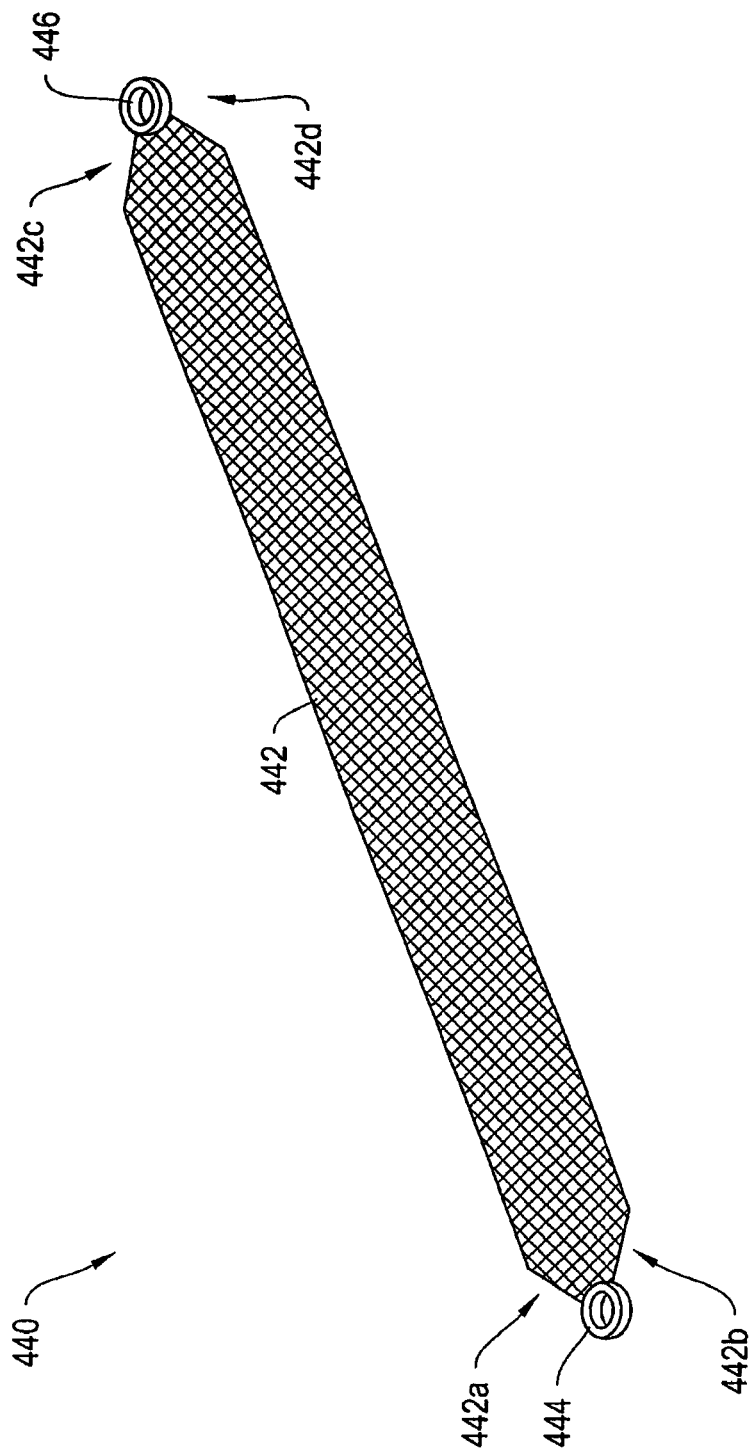
FIG. 18 shows an implant assembly including an implant and two end terminations, wherein each end termination includes a ring and no legs.

In alternative configurations, the end terminations are provided without radially extending legs. FIG. 18 shows an implant assembly 440 including an implant 442 and two end terminations 444 and 446 formed as respective apertures with no legs. A manufacturer affixes end terminations 444 and 446 to the implant 442 using any of the methods described above. In the depicted implant assembly 440, the corners of the implant 442 are trimmed at locations 442a, 442b, 442c, and 442d.

FIGS. 19A and 19B show an alternative end termination 450 that is flexible and made of a softer material, such as a soft durometer biocompatible material, than the previously described end terminations. The end termination 450 can couple to a surgical implant using any of the methods described herein with respect to other end termination embodiments. As shown in FIG. 19A, the end termination 450 includes an aperture 452, a first leg 454, and a second leg 456. The first leg 454 and the second leg 456 form a V-shape, and the aperture 452 lies in a plane that is perpendicular to the plane extending through the first and second legs 454 and 456. This perpendicular orientation results in the distal end of the shaft 458 aligning with the implant (not shown), and may be preferred by an operator for delivery of an implant. Since the end termination 450 is made of a relatively soft material, the ring 452 is in a collapsed state when the end termination 450 is at rest, as shown in FIG. 19A. In use, an operator couples the end termination 450 to a delivery device (not shown) by sliding the aperture 452 around a shaft 458 of the delivery device as depicted in FIG. 19B. The aperture 452 expands as the shaft 458 is pushed within the aperture 452, expanding the aperture 452 into a substantially circular configuration. The operator delivers the end termination 450 to a target tissue region, and retracts the shaft 458 to decouple the shaft 458 from the end termination 450. After the operator retracts the shaft 458, the aperture 452 returns to the collapsed state illustrated in FIG. 19A. The collapsed state provides a lower profile for the end termination 450 after the end termination 450 is implanted. As mentioned above, low profile implant assemblies may lessen damage to surrounding tissues.

Figure 20:
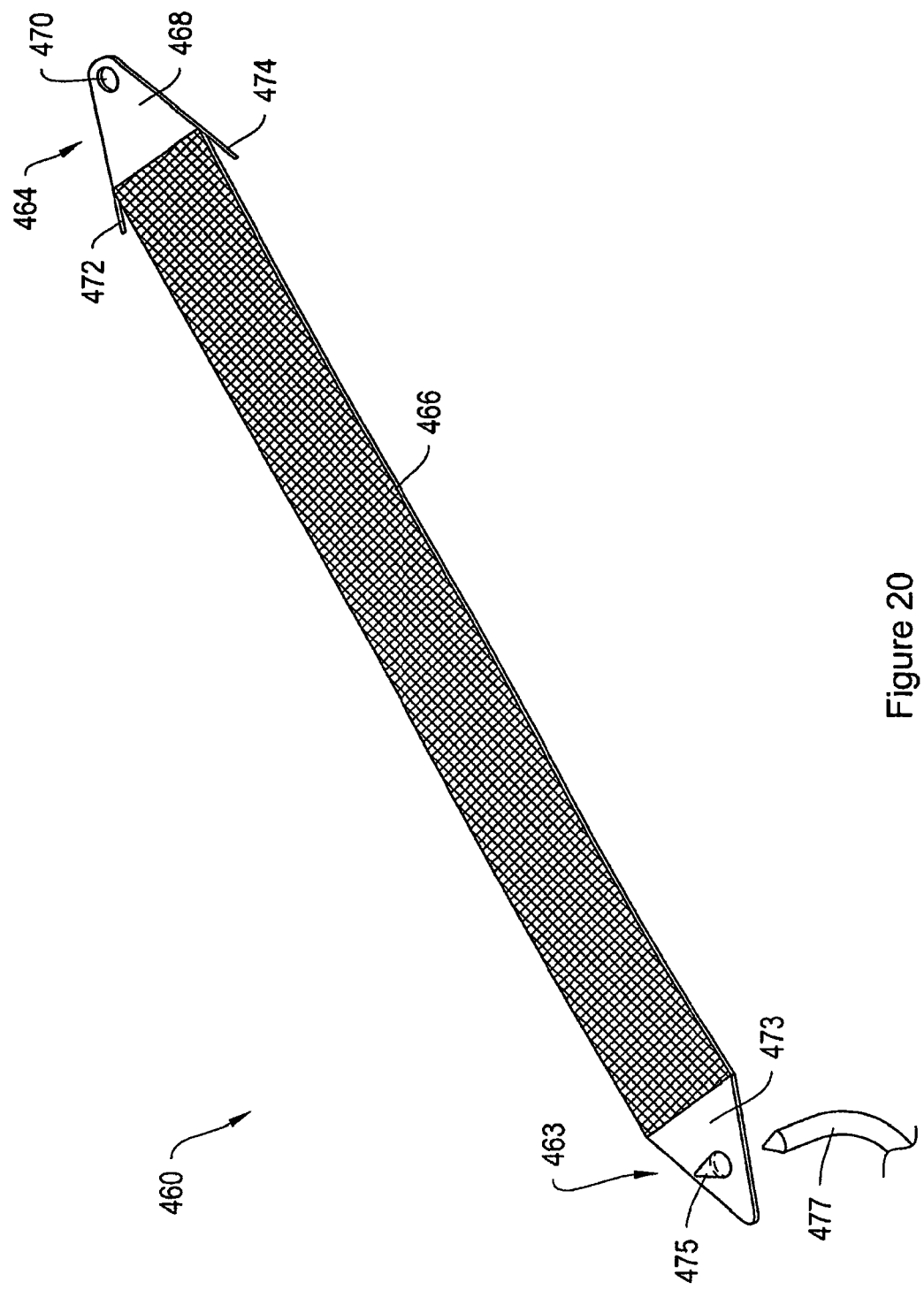
FIG. 20 shows an implant assembly including an implant and two alternative tab-shaped end terminations.

FIG. 20 shows another embodiment of an implant assembly 460 having alternative low profile end terminations 463 and 464 that lie substantially in the plane of the implant 466. End termination 464 includes a tab shaped region 468, an aperture 470 disposed within the tab shaped region 468, and legs 472 and 474 extending radially from the aperture 470. The depicted aperture 470 is small (i.e., in certain embodiments having a diameter of less than about 2 mm), and is sized to couple with a narrow needle of a delivery device. In other embodiments, the aperture 470 is sized to allow an operator to thread a filament therethrough. The filament may couple to a separate soft tissue anchor as described in connection with other embodiments herein. Similar to the legs described in connection with FIG. 16A above, the legs 472 and 474 anchor the implant 466 to soft tissue. In an exemplary manufacturing technique, a manufacturer dips the implant 466 in a curable plastic to form the end termination 468. The manufacturer then trims the plastic to create the tab shape 468 and the optional legs 472 and 474, and punches a hole through the plastic to create the aperture 470. However, in alternative embodiments, the manufacturer may pre-form the end termination 464 and subsequently snap-fit, glue, stitch, or otherwise attach it to the implant 466.

Alternative end termination 463 also includes a tab-shaped region 473 but does not include an aperture. Instead, end termination 463 includes a conical projection 475. The conical projection 475 is designed to interfit about the distal end of a delivery device shaft, such as the needle 477. In operation, an operator interfits the needle 477 with the projection 475 and drags the implant 466 towards a target tissue region. The projection 475 need not be conical, and in certain embodiments it is pyramidal.

As mentioned above, in certain embodiments, the soft-tissue anchors and the implant are separate elements that are assembled as an implant assembly. FIGS. 21A-D illustrate exemplary barbed soft tissue anchors that can be used for this purpose. In FIG. 21A, the anchor 500 includes a through-aperture 502, a body 504 and two rows of radial projections, or barbs 506. The through-aperture 502 couples to a shaft of a delivery device by fitting around the shaft, as will be discussed below. The depicted through-aperture 502 extends axially entirely through the body 504 of the anchor 500. In other embodiments, the body 504 includes a passage extending axially from the proximal end 500b of the anchor 500 only part way to the distal end 500a of the anchor 500.

The barbs 506 are relatively short (e.g., less than about 2 millimeters in length) and relatively wide (e.g., between about 1 millimeter and about 2 millimeters in width/diameter). Additionally, they have relatively flat terminal ends 508. The barbs 506 are also flexible. When an operator inserts the anchor 500 into an obturator membrane, the barbs 506 flex and compress against the body 504 of the anchor 500 to allow passage at least partially through the obturator membrane. After insertion within the obturator membrane, the barbs 506 expand radially from the body 504 and thereby resist retrograde motion back through the obturator membrane, thereby impeding the anchor 500 from disengaging from the obturator membrane.

FIG. 21B shows an alternative embodiment of an anchor 510, having a through-aperture 512, a body 514 and two rows of radial projections 516. The projections 516 are relatively long (e.g., greater than or equal to about 2 millimeters in length) and relatively wide (e.g., between about 1 millimeter and about 2 millimeters in width/diameter), as compared with anchor 500 of FIG. 21A.

FIG. 21C shows another embodiment of an anchor 520 having a body 522, an axially extending through-aperture 524 and radial projections 526. The anchor 520 is similar to anchors 500 and 510 of FIGS. 21A and 21B, respectively, except that the radial projections 526 have pointed rather than flat terminal ends, in contrast to the projections 506 and 516. The pointed projections 526 impede retrograde forces that may be applied to the anchor 520, since the projections 526 more firmly incise into and engage with the tissue of the obturator membrane and thereby prevent disengagement of the anchor 520 from the obturator membrane. In particular, the projections have an initial width at a base 530 comparable to the width of the projections 506 and 516, and have a length similar to that of the projections 506.

FIG. 21D shows another illustrative anchor 540, including a relatively long (e.g., between about 2.5 centimeters and about 3.5 centimeters) body 542 and five rows of relatively long (e.g., greater than about 5 millimeters) radial projections 544. As in the case of the above described examples, the anchor 540 includes a radially extending through-passage 546.

Figure 21E:
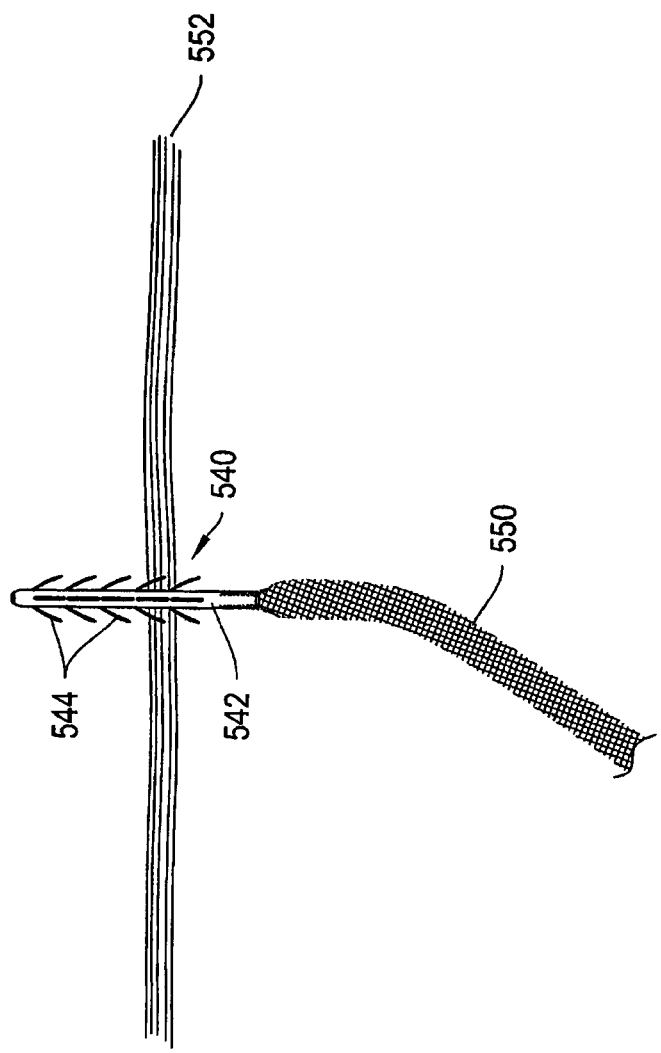
FIG. 21E shows a barbed anchor coupled to a portion of a surgical implant and anchored to an obturator membrane.

FIG. 21E shows the barbed anchor 540 coupled to a portion of a surgical implant 550 and anchored to an obturator membrane 552. In operation, an operator drives the anchor 540 partially (as illustrated) or entirely through the obturator membrane 552 using a delivery device and/or method that will be discussed below. The barbs 544 on the anchor 540 engage with the obturator membrane 552 and inhibit the anchor 540 from retracting out of the membrane 552 after insertion. An operator then optionally drives the anchor 540 further into the obturator membrane 552 to tension the associated surgical implant 550. The long body 542 is beneficial in part because the operator can drive the anchor 540 various distances through the obturator membrane 552, corresponding to various tensions of implant 550. When the operator drives the anchor 540 entirely through the obturator membrane 552, the surgical implant 550 is driven through the obturator membrane 552. The implant 550 may have tangs to engage with and anchor to the obturator membrane 552. The operator can then extend or retract a portion of the implant 550 through the obturator membrane 552 to tension the implant 550. In certain embodiments, the implant 550 is not coupled to soft tissue anchor 540 and anchors itself to the obturator membrane 552.

Figure 22A:
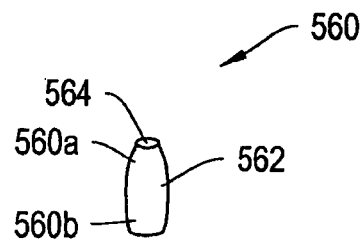
FIG. 22A shows a soft tissue anchor with a smooth outer surface and without barbs.

FIG. 22A illustrates a soft tissue anchor 560 without barbs. In particular, the soft tissue anchor 560 has a smooth outer surface 562. Like the anchors depicted in FIGS. 21A-E, the anchor 560 includes a through-aperture 564 that fits around the shaft of a delivery device, as will be discussed below. The depicted through-aperture 564 extends axially entirely through the anchor 560. In other embodiments, the anchor 560 includes a passage extending axially from the proximal end 560b of the anchor 500 only part way to the distal end 560a of the anchor 560.

Figure 22B:
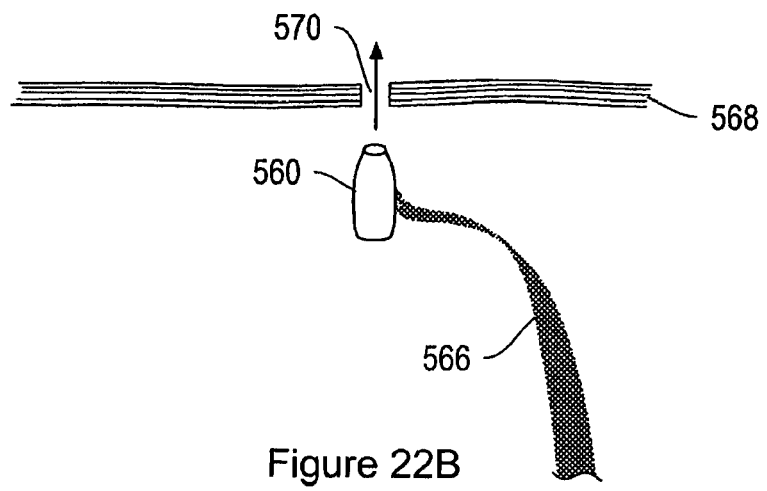
FIGS. 22B-22C illustrate an exemplary technique for using the anchor of FIG. 22A to anchor a surgical implant to an obturator membrane.
Figure 22C:
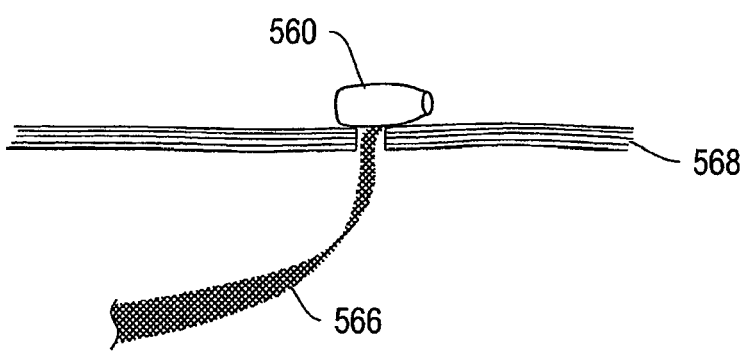

FIGS. 22B-22C illustrate an exemplary technique for using the anchor 560 to anchor a surgical implant 566 to an obturator membrane 568. In particular, an operator forms an aperture 570 within the obturator membrane 568 using, for example, a needle or dilator. Next, the operator couples the anchor 560 to an implant 566 using methods discussed below. The operator then drives the anchor 560 through the aperture 570. When retrograde tension is applied to the implant 566, the anchor 560 pivots to a horizontal orientation, depicted in FIG. 22C, and aligns with the obturator membrane 568, and this horizontal orientation prevents the anchor 560 from disengaging from the obturator membrane 568.

Figure 23:
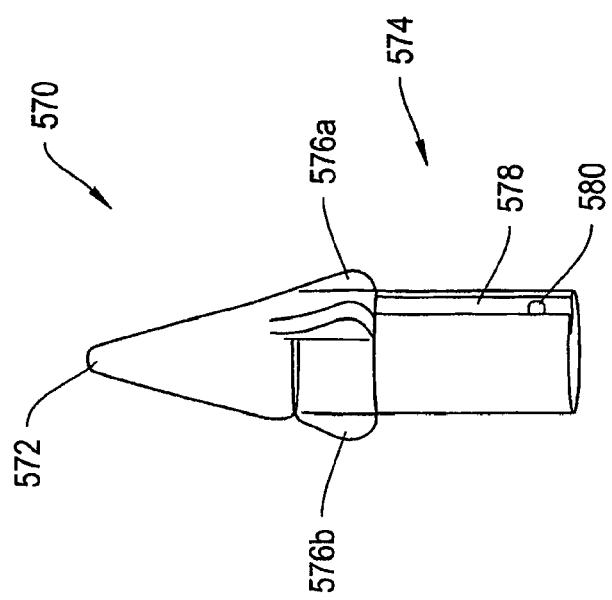
FIG. 23 shows a soft tissue anchor shaped like an arrowhead.

FIG. 23 illustrates an alternative soft tissue anchor 570 shaped like an arrowhead. More particularly, the anchor 570 includes a point 572 at a distal end, a cylindrical shaft 574 at a proximal end, and wings 576a and 576b at a distal end of the cylindrical shaft 574. The anchor 570 further includes a slot 578 disposed longitudinally along the cylindrical shaft 574 and a cross bar 580 bridging the slot 578. In one exemplary technique, an operator couples the anchor 570 to a filament by interfitting the filament through slot 578 and threading the filament around the cross bar 580.

As mentioned above, the soft tissue anchors couple to surgical implants in a variety of ways. In certain embodiments, such as with pelvic floor repair implants that have long lateral widths or laterally extending legs or extension regions, they directly couple to the surgical implant. In others, they are spaced away from the surgical implants. In any case, the anchors may be fixedly coupled, or adjustably coupled so that an operator can tension the implant.

Figure 24:
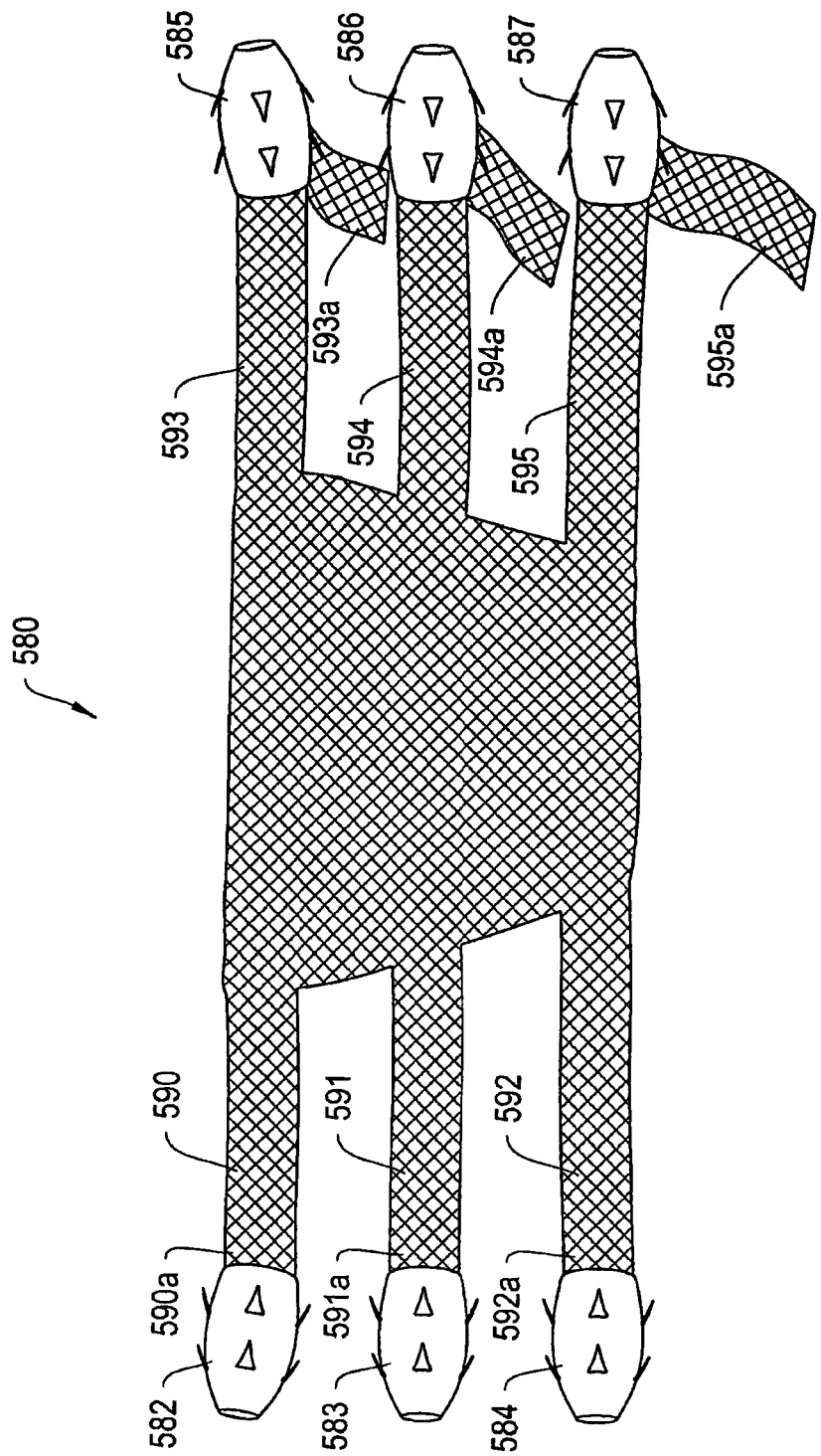
FIG. 24 shows the implant of FIG. 2A and depicts alternative approaches to couple soft tissue anchors with straps of the implant.

FIG. 24 illustrates a surgical implant 580, similar to the surgical implant 30 depicted in FIG. 2A, with soft tissue anchors 582-587 coupled directly to respective ones of the straps 590595. In certain embodiments, the anchors are fixedly coupled to the respective straps, as depicted with respect to soft tissue anchors 582-584. The ends 582a, 583a, and 584a of the anchors 582584 are affixed to respective ends 590a, 591a, and 592a of the straps 590-592 by gluing, heat bonding, tying, or other permanent affixation methods.

In other embodiments, the anchors are adjustably coupled to respective straps, as depicted with respect to soft tissue anchors 585-587. As shown, the mesh straps 593-595 are threaded through buckles or apertures of the anchors 585-587, which exposes free ends 593a, 594a, and 595a of the mesh straps that have threaded entirely through the anchors 585-587. The operator can pull free end 595a to thread more of mesh strap 595 through anchor 587 and increase the length of the exposed free end 595a. As a result, the tension applied by strap 595 to the surgical implant 580 will increase. The operator can similarly tension the implant 580 by adjusting the other mesh straps.

Figure 25A:
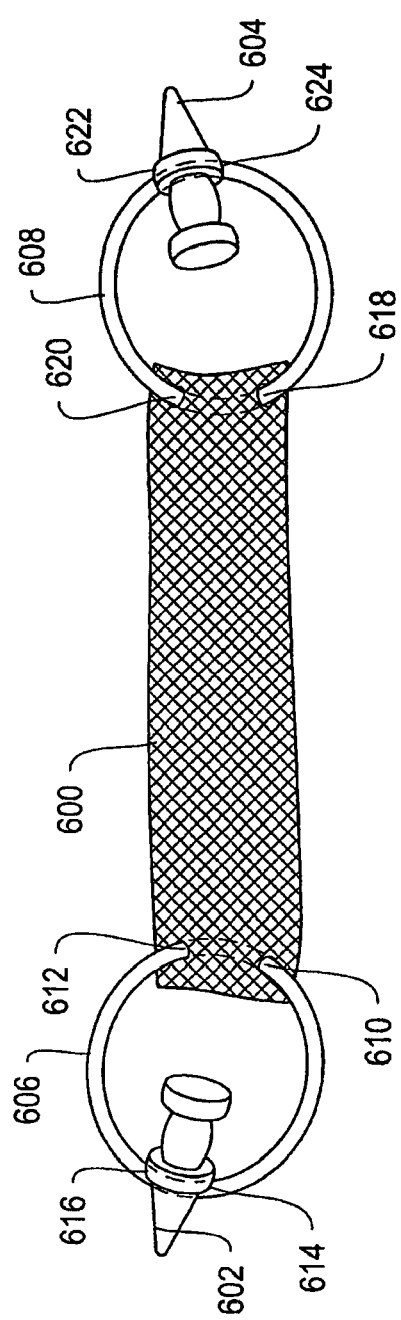
FIG. 25A illustrates a surgical implant coupled with soft tissue anchors via elastic rings.

As mentioned above, certain exemplary surgical implants may be used that do not extend the full obturator-to-obturator length of the patient. In such instances, soft tissue anchors can indirectly couple to the surgical implant via, for example, filaments or rings which space the anchors away from the surgical implant to extend the anchoring points. FIG. 25A illustrates a surgical implant 600 coupled with soft tissue anchors 602 and 604 via elastic rings 606 and 608. The rings 606 and 608 couple their respective anchors to the implant by a set of through-apertures. More particularly, the ring 606 couples with anchor 602 by threading through the apertures 614 and 616 in soft tissue anchor 602, and couples with surgical implant 600 by threading through the apertures 610 and 612 in surgical implant 600. Similarly, the ring 608 couples to soft tissue anchor 604 by threading through the apertures 622 and 624 in soft tissue anchor 604, and couples to the surgical implant 600 by threading through the apertures 618 and 620 in the surgical implant 600. As mentioned above, woven surgical implants may stretch and damage due to stresses during delivery of the implant. The elastic rings 606 and 608 stretch to absorb lateral stresses, thereby preventing damage to the implant 600 during delivery.

Figure 25B:
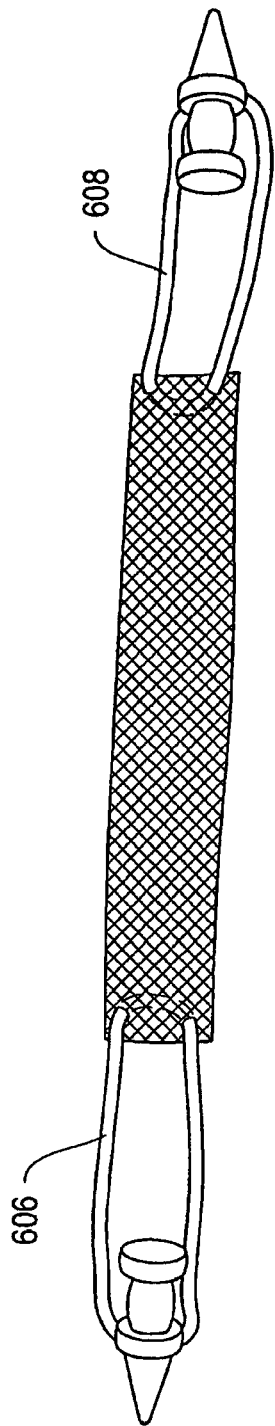
FIG. 25B shows the elastic rings of FIG. 25A in stretched states.

Additionally, the elastic rings 606 and 608 adjust to short term and/or long term changes in the patient's changing anatomy to prevent damage to the surgical implant 600. For example, when the patient sneezes, coughs, or jumps, muscles in the pelvic region can contract and anatomical structures may shift. Anatomical structures may also shift over long periods of time because of the patient's changing anatomy due to, for example, weight gain or weight loss. In such cases, the elastic rings 606 and 608 stretch to absorb the stresses caused by these short-term and long-term changes, thereby preventing the changes from damaging the surgical implant 600. FIG. 25B shows the elastic rings 606 and 608 in stretched states.

FIGS. 26A-G illustrate an alternative embodiment of an implant assembly 630 having a surgical implant 632 that is spaced away from and couples with soft tissue anchors 634, 636, 638, and 640 via filaments 642, 644, 646, and 648. As will be discussed, the spacing of the soft tissue anchors 634, 636, 638, and 640 from the implant 632 can be adjusted to tension the implant, and to allow the soft tissue anchors 634, 636, 638, and 640 to reach various target tissue regions in the patient's retropubic space.

Figure 26A:
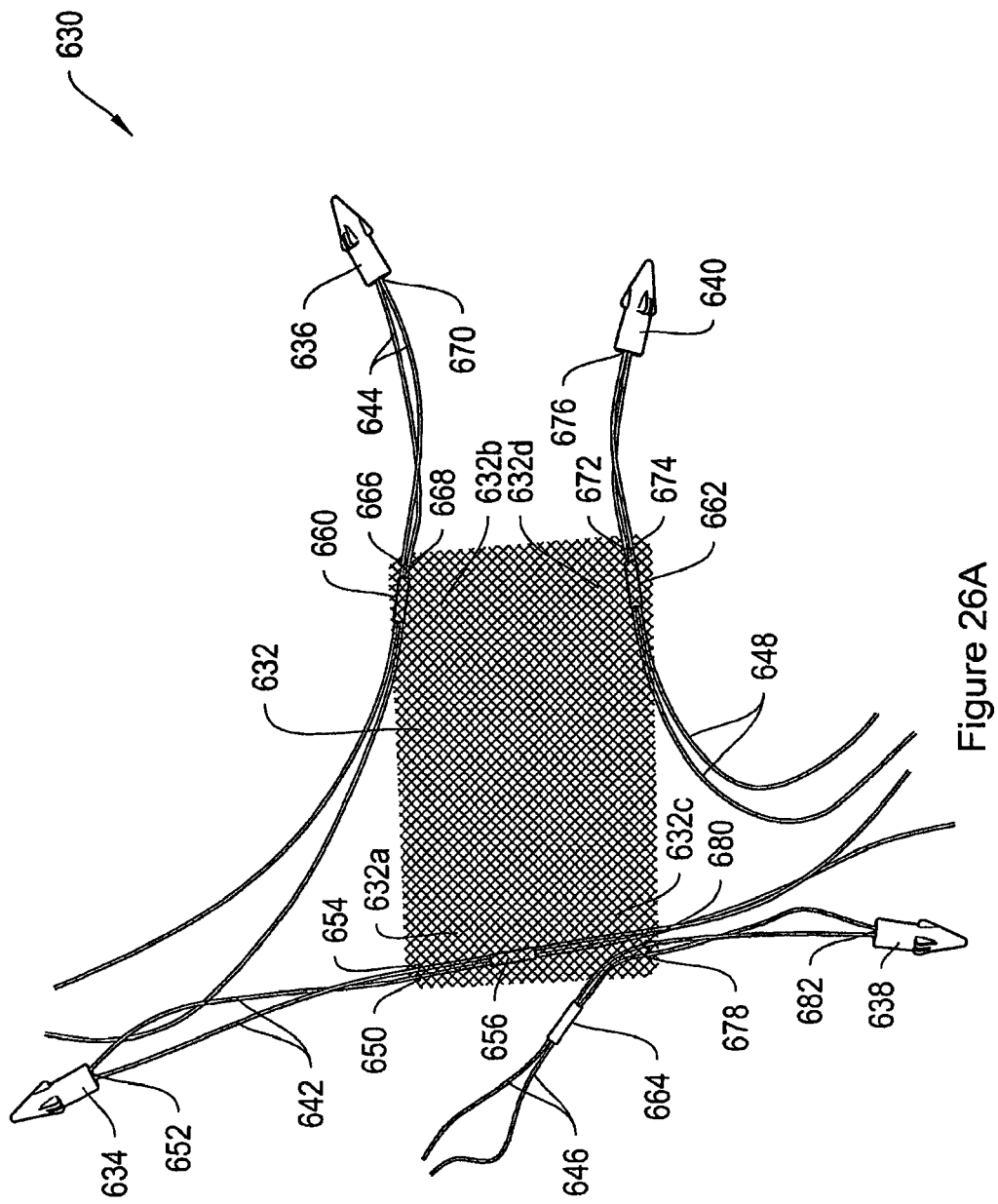
FIG. 26A shows an implant assembly including a surgical implant that couples with soft tissue anchors via filaments.
Figure 26B:
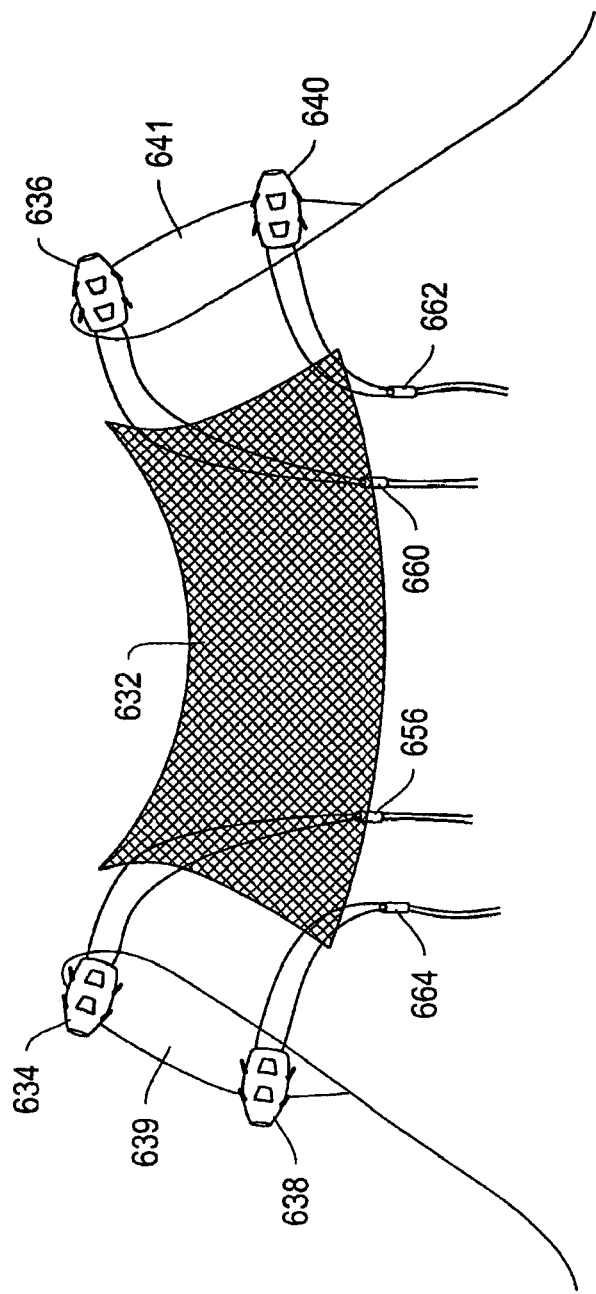
FIG. 26B shows the implant assembly of FIG. 26A anchored within the pelvic region of a patient.

The depicted surgical implant 632 is similar to the surgical implant 70 of FIG. 4, and the depicted soft tissue anchors 634, 636, 638, and 640 are similar to the soft tissue anchor 570 of FIG. 23. More particularly, as shown in FIG. 26A, the filament 642 threads through a first aperture 650 of the implant 632, through an aperture 652 in the anchor 634, and through a second aperture 654 of the implant 632. Two ends 642a and 642b of the filament 642 are cinched by a slidable filament locking mechanism 656 into an adjustable size loop. Similarly, the implant 632 couples to the soft tissue anchor 636 via filament 644, filament locking mechanism 660, and apertures 666, 668, and 670, to soft tissue anchor 640 via filament 648, filament locking mechanism 662, and apertures 672, 674, 676, and to soft tissue anchor 638 via filament 646, filament locking mechanism 664, and apertures 678, 680, and 682. FIG. 26B shows the implant 632 after anchoring the soft tissue anchors 634, 636, 638, and 640 to obturator membranes 639 and 641. Instead of filament locking mechanisms 660, 662, 664, and 656, other adjustable cinching elements can be used, such as slip knots.

Figure 26C:
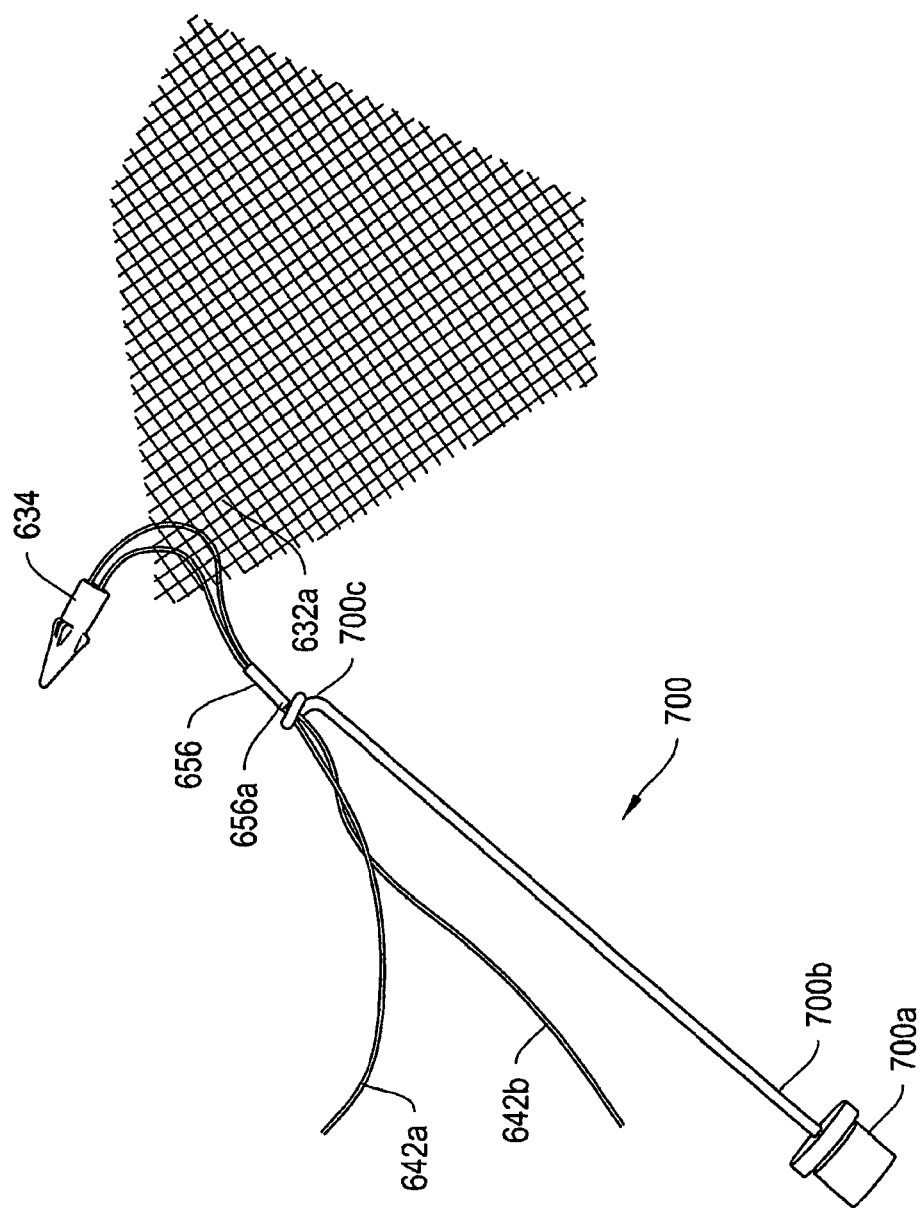
FIGS. 26C-D show an exemplary technique to tension the implant of FIG. 26A.
Figure 26D:
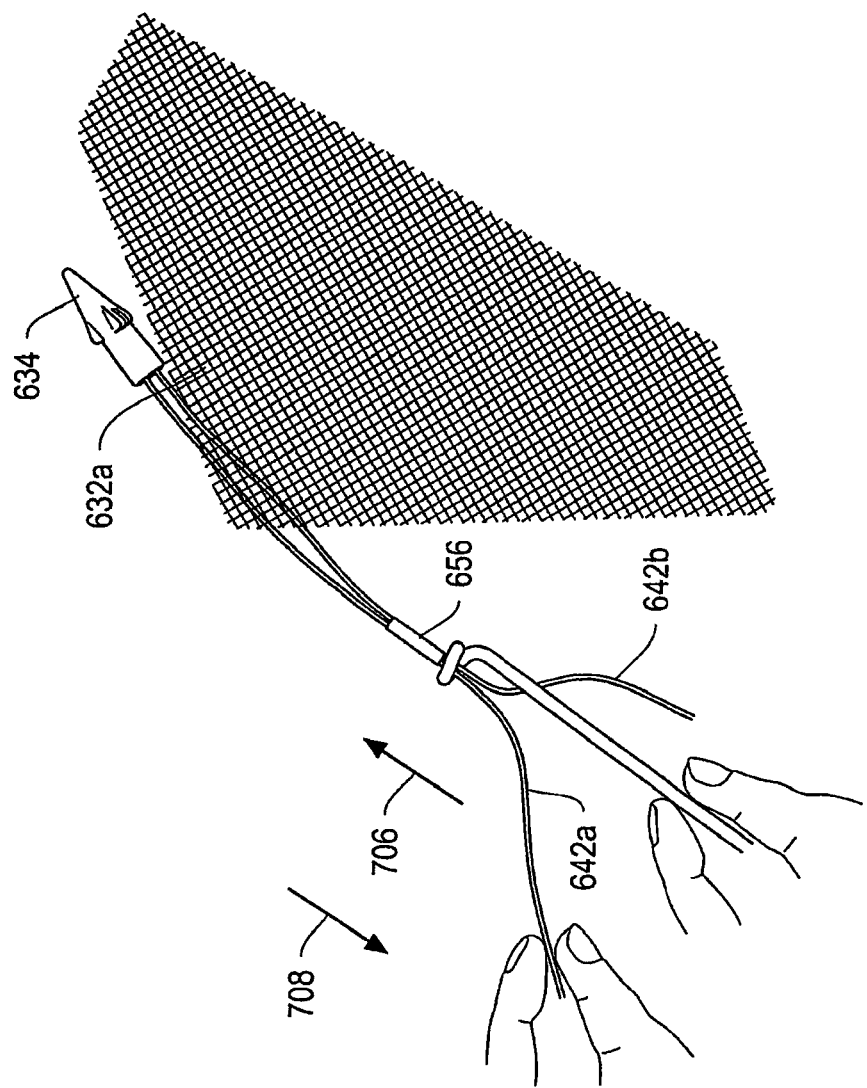

The filaments 642, 644, 646, and 648 along with filament locking mechanisms 660, 662, 664, and 656 allow an operator to adjustably tension the implant 632 within the pelvic region of the patient. More particularly, once an operator delivers the implant 632 to a target tissue region, such as the obturator membranes as depicted in FIG. 26B, the operator tensions surgical implant 632 and/or adjusts its length or width using filament locking mechanisms 660, 662, 664, and 656 by drawing implant corners 632a, 632b, 632c, and 632d towards respective anchors 634, 636, 638, and 640. In particular, as depicted in FIGS. 26C-D, an operator grasps a tensioning tool 700 with one hand and one or both filament ends 642a and 642b with another hand. The tensioning tool 700 includes a handle 700a, a shaft 700b extending distally from the handle, and a curved, looped, or hooked tip 700c at a distal end of the shaft 700b oriented at an angle to the shaft 700b. The tip 700c of the tensioning tool 700 is sized and shaped to hook onto and engage with the filament locking mechanism 656 and to slide the filament locking mechanism 656 along the filament 642 to adjust the distance from the implant corner 632a to the anchor 634 (secured to a target tissue region) and thereby tension and/or adjust the length and/or width of the implant assembly.

In an exemplary technique, the operator abuts the tip 700c of the tensioning tool 700 against the proximal end 656a of the filament locking mechanism 656. The filament locking mechanism 656 may be external to the patient, within the vaginal canal, or beyond the vaginal incision and within the pelvic region of the patient. When the filament locking mechanism 656 is beyond the vaginal incision, the operator inserts the tensioning tool 700 through the same vaginal incision. Next, as shown in FIG. 26D, the operator pushes the tensioning tool 700 in a distal direction 706 towards the implant corner 632a while pulling one or both filament ends 642a and 642b in a proximal direction 708 away from the implant corner 632a. The filament ends 642a and 642b may lie exterior to the patient, within the vaginal canal, or beyond the vaginal incision. If the filament ends 642a and 642b are inaccessible by hand, the operator may use forceps or other suitable instruments to grasp the filament ends 642a and 642b. The filament locking mechanism 656 then slides in a distal direction 706 along the filament 642 and towards the implant corner 632a. In certain embodiments, the filament locking mechanism 656 is configured to slide in one direction (i.e., distally 706) and not in a retrograde direction (i.e., proximally 708). The same may apply if slip-knots are used (i.e., the slip knots may be one-way slip knots).

Figure 26E:
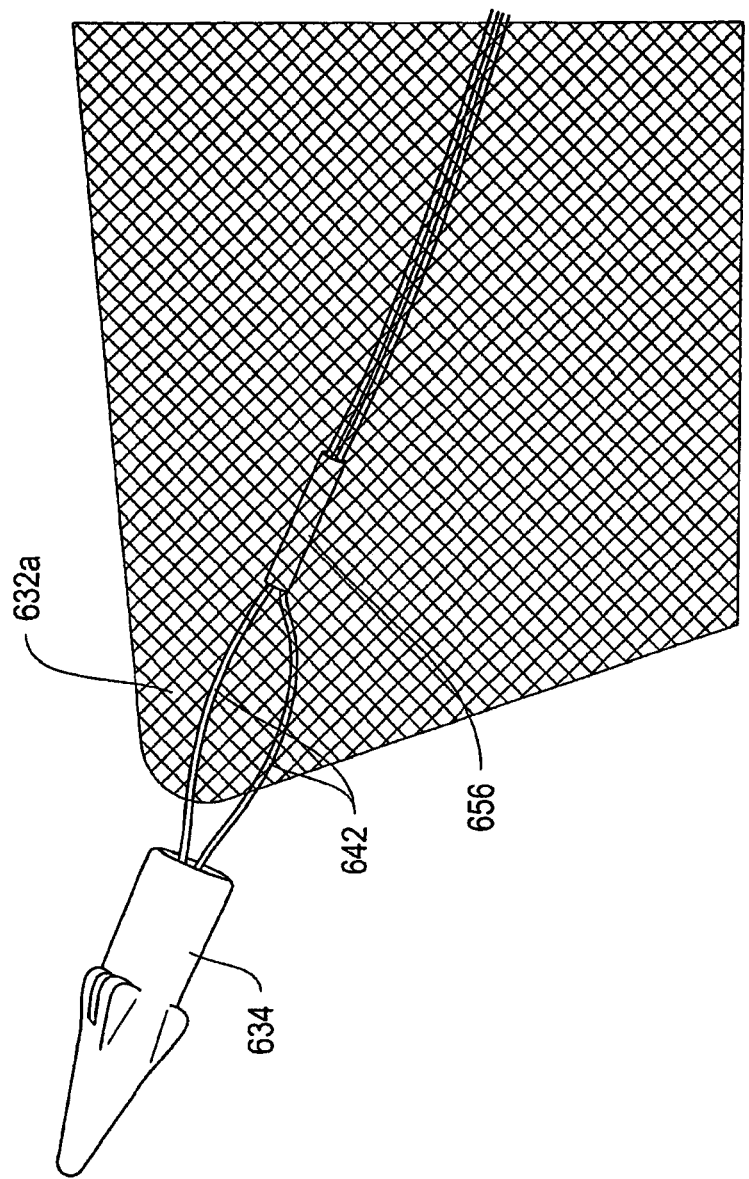
FIG. 26E shows a corner of the implant of FIG. 26A after an exemplary tensioning technique.
Figure 26F:
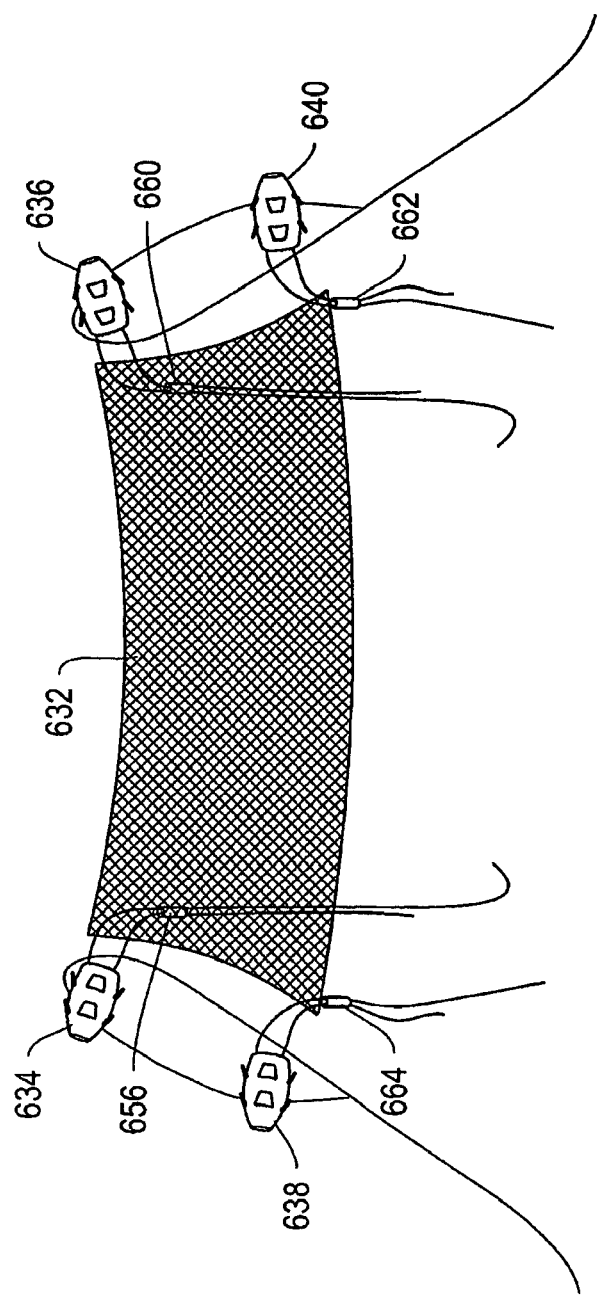
FIG. 26F shows the implant assembly of FIG. 26B anchored within the pelvic region of a patient after tensioning.

The filament locking mechanism 656 then abuts against implant corner 632a and draws implant corner 632a towards the anchor 634 which increases the tension of the implant 632. FIG. 26E depicts the implant corner 632a, the anchor 634, the filament locking mechanism 656, and the filament 642 after such an exemplary tensioning technique. The operator then repeats this process for implant corners 632b, 632c, and 632d until the implant 632 is properly tensioned. FIG. 26F depicts the implant 632 after the operator has tensioned all four corners 632a-d. While the depicted implant 632 couples to four anchors at respective corners 632a-d, the implant 632 may also couple to anchors at sides or edges of the implant 632 that are spaced away from the corners 632a-d.

Figure 26G:
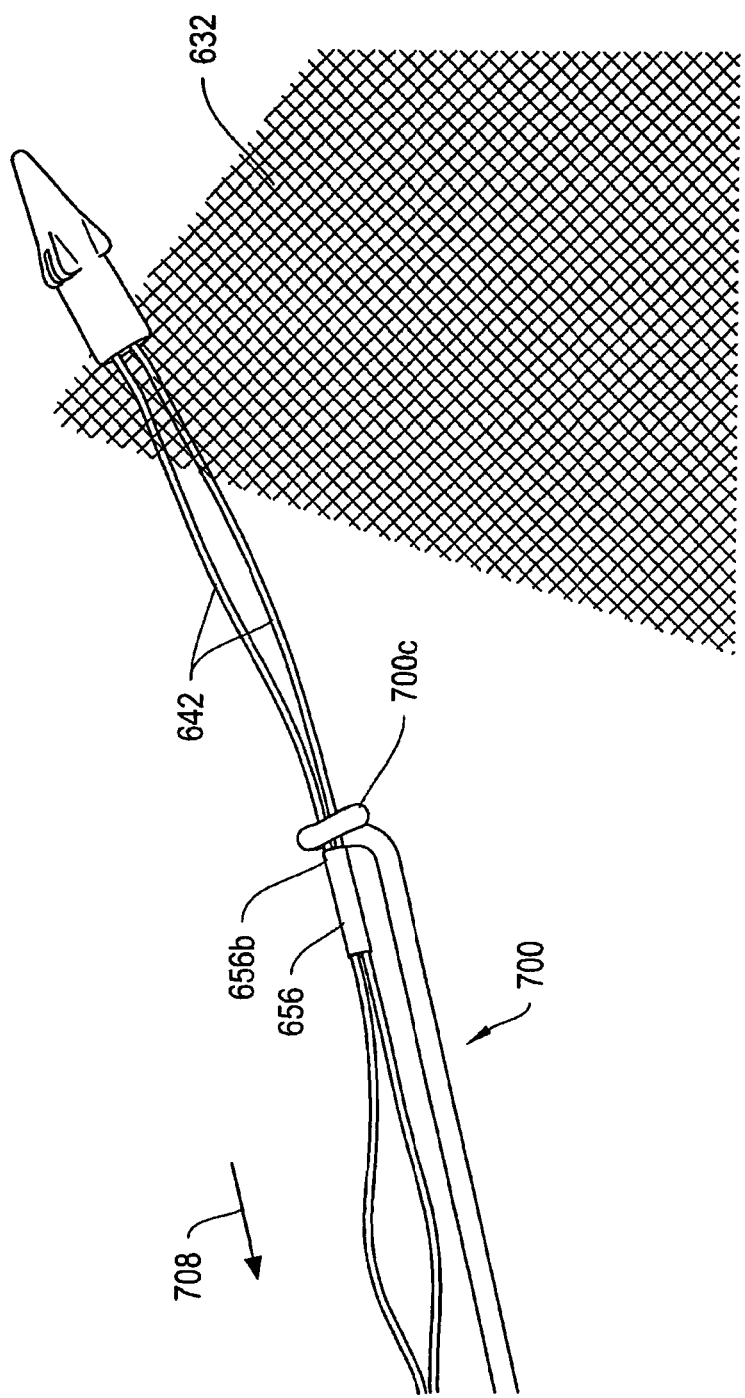
FIG. 26G shows an exemplary technique for loosening the implant of FIG. 26A.

The operator can also loosen the implant 632 using filament locking mechanisms 660, 662, 664, and 656. An exemplary technique is depicted in FIG. 26G, in which an operator grasps the tensioning tool 700 and abuts the tip 700c against the proximal end 656b of the filament locking mechanism 656. The operator pulls the tensioning tool in a proximal direction 708, and as a result the filament locking mechanism 656 slides proximally along the filament 642. The implant corner 632a is then free to slide in a proximal direction 708 along the filament 642. The operator then repeats this process for implant corners 632b-d until the implant 632 is properly loosened to a desired tension.

Although the depicted tensioning and loosening technique was described in connection with the anchors 634, 636, 638, and 640 anchoring to respective obturator membranes 639 and 641, the anchors 634, 636, 638, and 640 can also couple to other target tissue regions in the patient's retropubic space. For example, in one alternative implementation, the anchors 634 and 636 anchor to target tissue regions of the patient's sacrospinous ligament or levator ani muscle, while the anchors 638 and 640 anchor to target tissue regions of the patient's obturator membranes 639 and 641.

Having described various exemplary surgical implants, and systems and methods for anchoring the implants within the patient and tensioning the implants once the implants are anchored, various exemplary devices are now described for use in inserting the surgical implants through a single vaginal incision. In certain embodiments, the delivery devices include a handle and a shaft extending distally from the handle to couple with a soft tissue anchor. In certain configurations, the delivery devices include movable parts that allow an operator to control the release of the soft tissue anchor from the delivery device, measure the delivery location of the soft tissue anchors, and/or measure appropriate lengths of an implant for use in a particular patient. The delivery devices are generally shaped so that an operator can guide a distal end of the delivery device through the patient's vaginal opening, through the vaginal incision, and towards a patient's obturator membrane. In certain embodiments, the delivery device is also shaped to extend through the vaginal incision to the contra-lateral obturator membrane, and in others the operator is provided with a second device having an opposite curvature to extend through the vaginal incision and to the contra-lateral obturator membrane. In certain exemplary techniques, soft tissue anchors secure the implant to target tissue regions, whereas in others, tanged portions of the implant secure the implant to the target tissue regions.

Figure 27:
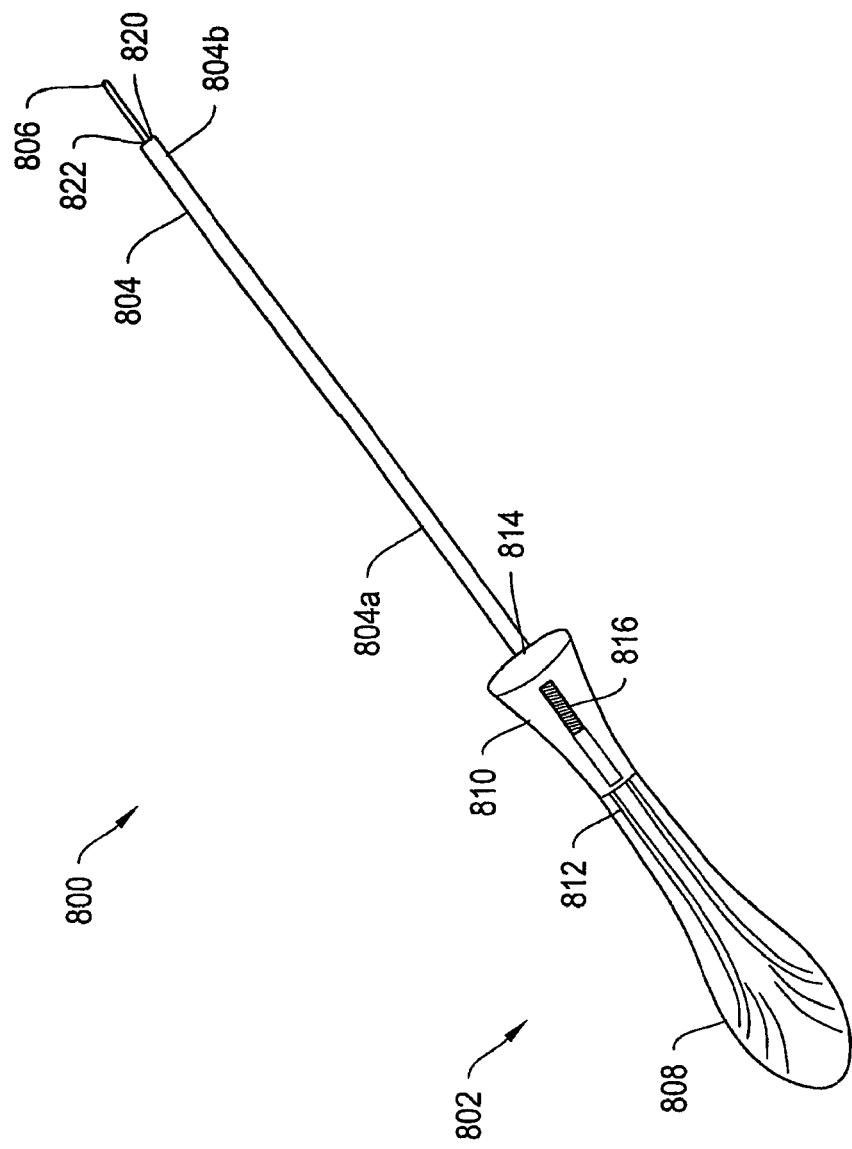
FIG. 27 shows a delivery device having a movable shaft and a fixed cannula for delivering an implant assembly to the pelvic region of a patient.

More particularly, FIG. 27 shows a delivery device 800 for delivering a implant assembly to the pelvic region of a patient. The delivery device 800 includes a handle 802, a cannula 804 extending distally from the handle 802, and a movable shaft 806.

The handle 802 includes a proximal end 808 and a distal end 810. The handle 802, as depicted, is substantially straight and tapers inward from the proximal end 808 to a distal location 812. The distal portion 810 of the handle 802 tapers outward from the distal location 812 to prevent a medical operator's hand from slipping distally while grasping the handle 802.

The cannula 804 has a proximal end 804a and distal end 804b, and extends distally from a distal most end 814 of the handle 802. The cannula 804 is substantially straight, but this need not be the case. In alternative embodiments, it may include any combination of curved sections and straight sections, and may extend into one, two or more planes. The shaft 806 interfits within the cannula 804 and mechanically couples at a proximal end to a slider 816 on/within the handle 802. An operator may slide the slider 816 axially within the slot to retract and extend the shaft 806 in and out of the cannula 804.

With the shaft 806 extended, a distal most end 820 of the cannula 804 forms a shoulder 822.

In operation, an operator slides the slider 816 distally and thereby extends the shaft 806 to an extended position. Next, the operator interfits a tissue anchor, such as the tissue anchors described above, onto the distal end of the shaft 806. The operator then inserts the distal end of the delivery device 800 with the tissue anchor into the body of the patient, for example, via the incision in the vaginal wall according to the illustrative procedure. The operator advances the device until the anchor is placed at a target tissue region such as an obturator membrane. Next, the operator retracts the slider 816 to retract the shaft 806 into the cannula 804 and out of the tissue anchor. In certain implementations, the tissue anchor abuts against the shoulder 822 of the delivery device 800 and thereby disengages from the shaft 806 when the shaft 806 retracts into the cannula 820. The operator removes the delivery device 800 from the patient and thereby leaves the tissue anchor placed and anchored at the target tissue region. The anchor may be coupled to an implant that is coupled to one or more other soft tissue anchors. The operator may repeat the procedure for the other soft tissue anchors with the same or a different delivery device.

According to the illustrative embodiment, when the shaft 806 is in an extended position, the exposed distal section of the shaft 806 is between about 2 centimeters and about 4 centimeters long. In other illustrative embodiments, it is between about 1 centimeter and about 3 centimeters long. In further illustrative embodiments, the narrowed distal section of the shaft 806 has an outside diameter of between about 0.03 inches and about 0.05 inches. In one illustrative embodiment, it has an outside diameter of about 0.04 inches. According to other configurations, the outside diameter of the cannula 804 at the distal end 820 is between about 0.07 inches and about 0.1 inches. In one implementation, the outside diameter of this portion of the cannula is about 0.09 inches. According to one configuration, the total distance from the distal end 814 of the handle 802 to the distal most tip 806a of the shaft 806, with the shaft extended is between about 7 centimeters and about 20 centimeters. In other configurations, the total distance is between about 8 centimeters and about 12 centimeters.

Figure 28:
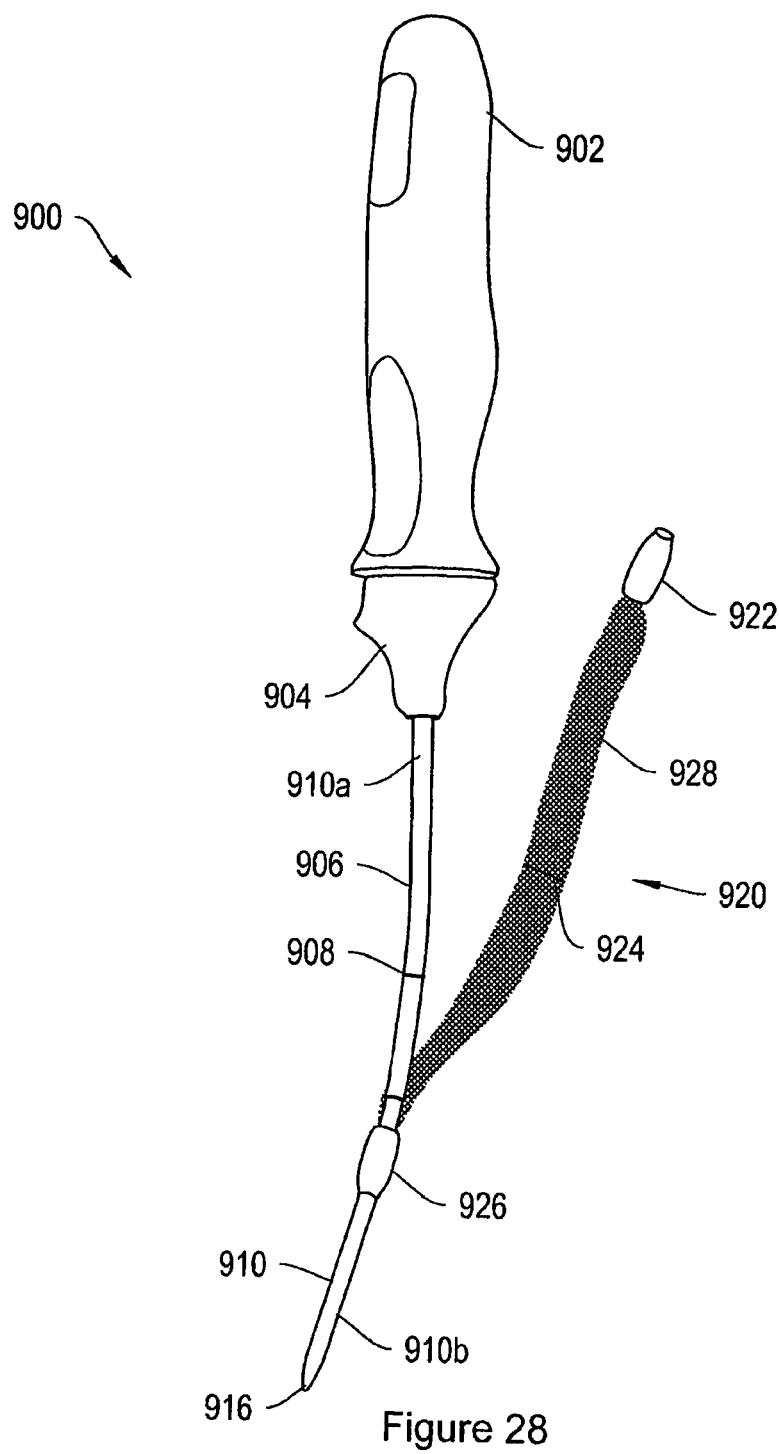
FIG. 28 shows a delivery device having a fixed shaft and a moveable cannula for delivering an implant assembly to the pelvic region of a patient.

Alternatively, delivery devices may include a fixed shaft and a movable cannula disposed about the fixed shaft. FIG. 28 shows such a delivery device 900 and an implant assembly 920. The delivery device 900 includes a handle 902, a needle/shaft 910 extending distally from the handle 902, a pusher button 904 distal to the handle 902, and a cannula 906 disposed about the shaft 910 and extending distally from the pusher button 904.

The shaft 910 is generally linear at its proximal end 910a, and curves towards its distal end 910b. However, in other embodiments the shaft 910 may be straight, may include any combination of curved sections and straight sections, and/or may extend into one, two or more planes. When inserting the delivery device 900 through the vaginal incision and towards an obturator membrane, a straight shaft may facilitate access for an operator to more posterior regions of an obturator membrane, whereas a shaft with more curvature may facilitate access to more anterior regions of an obturator membrane. In certain embodiments, the shaft may be shorter in length than the depicted shaft 910 which may provide an operator with better control. In certain embodiments, the shaft 910 has a diameter of between about 0.075 inches and about 0.2 inches, and in certain embodiments is about 0.107 inches. The shaft 910 includes a tip 916. The tip 916 can be sharp and suited to incise and/or dissect human tissue, or blunt and suited for blunt dissection and/or dilation of human tissue. In certain embodiments, the tip is blunt so as to avoid damaging sensitive structures such as organs, nerves, and arteries, as will be discussed below.

The pusher button 904 comprises polymeric materials and is mechanically coupled to the cannula 906. The cannula 906 is shorter in length than the shaft 910, and when the button 904 is in a retracted state, as depicted in FIG. 28, the shaft 910 is exposed at its distal end 910*b*. In certain implementations, the exposed portion of the shaft 910 is slightly longer than about half the length of the implant assembly 920 so the implant assembly 920 remains external to the body during initial placement of the shaft 910.

The implant assembly 920 includes an implant 928 and anchors 926 and 922 coupled to the implant 928. The anchors 926 and 922 are similar to anchor 560 of FIG. 22A, but can be similar to any of the anchors described herein. The anchors 926 and 922 include respective axial through holes. The inner diameter of the anchor 926 is preferably sized and shaped to fit around and slide against the outer diameter of the shaft 910. The anchor 926 slides proximally along the shaft 910 and abuts the distal end of the pusher cannula 906. The outer diameter of the anchor 926 can be smaller, larger, or equal to the outer diameter of the pusher cannula 906. The implant 928 further includes a center mark 924 indicating the center, or "half-length," of the implant 924. In one usage of device 900, the center mark 924 of the implant is placed directly underneath the urethra. However, in other implementations, device 900 is used with larger meshes that include marks which are placed under other anatomical structures, such as, for example, the base of the bladder.

The cannula 906 includes a pusher mark 908 that indicates where the center mark 924 of the implant 928 will be positioned after the implant 928 has been placed using the delivery device 900. In one exemplary mode of operation, when an operator delivers the implant 928 using the delivery device 900 with the pusher button 904 and the cannula 906 retracted, the operator positions the pusher mark 908 underneath the urethra such that when the operator advances the pusher, the center mark 924 of the implant 928 lies about or directly underneath the urethra. However, in embodiments wherein implants include marks indicating placement of the implant with respect to another anatomical structure, such as the base of the bladder, the operator accordingly positions the pusher mark 908 underneath that anatomical structure.

Figure 29:
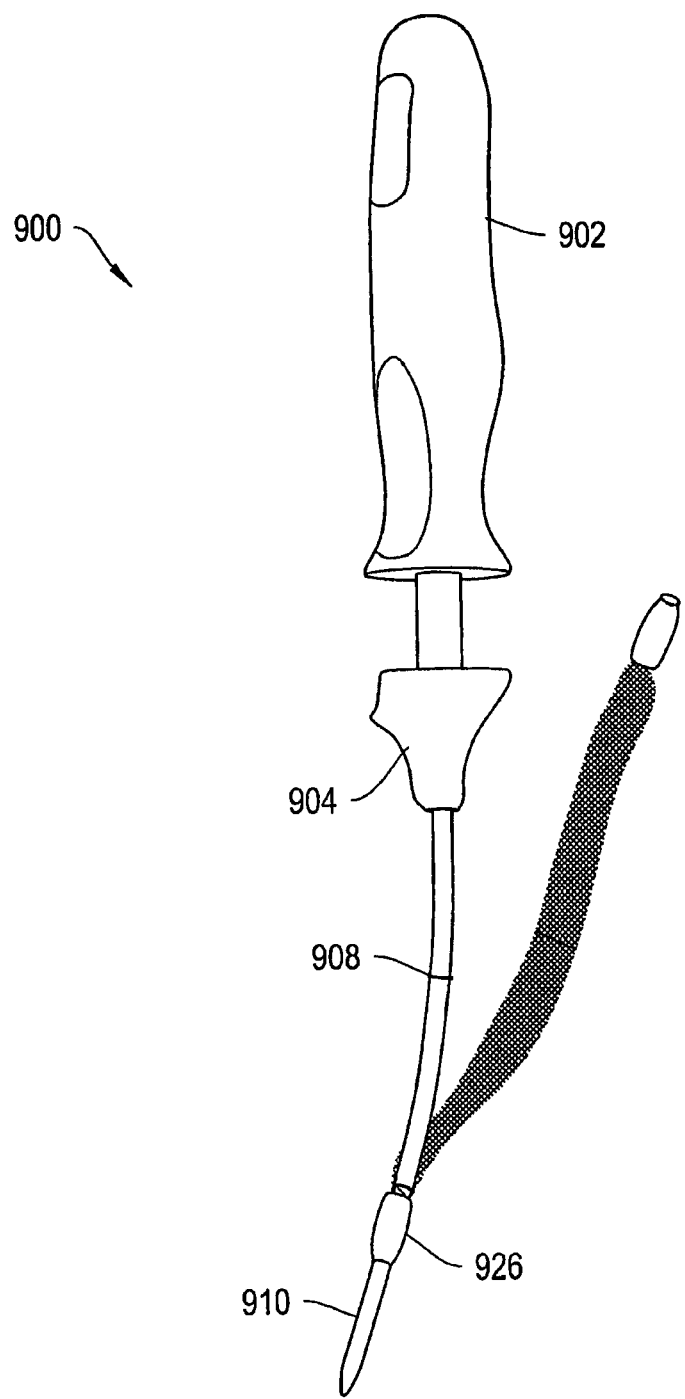
FIG. 29 shows the delivery device of FIG. 28 in an extended state.

In operation, an operator couples an anchor 926 of the implant assembly 920 to the shaft 910. The anchor 926 slides proximally along the shaft 910 and abuts the distal end of the pusher cannula 906. The operator inserts the shaft 910 into the body of the patient and guides the tip 916 towards a target region while the button 904 is retracted. In certain implementations, the operator advances the tip past the target region. The operator optionally gauges his proximity to the target region buy aligning the cannula mark 924 with an anatomical landmark such as the urethra. The operator advances the button 904 distally, and thereby advances the distal end of the cannula 906 towards the tip 916 of the shaft 910. FIG. 29 shows the delivery device 900 of FIG. 28 with the pusher 904 in an extended state. As will be described below, in certain implementations the operator advances the anchor 926 to a target region with the anatomy of the patient without pushing the anchor 926 off of the shaft 910. Instead, after placement of the anchor 926, the operator retracts the device 900 in a retrograde direction, which decouples the anchor 926 from the shaft 910.

Figure 30:
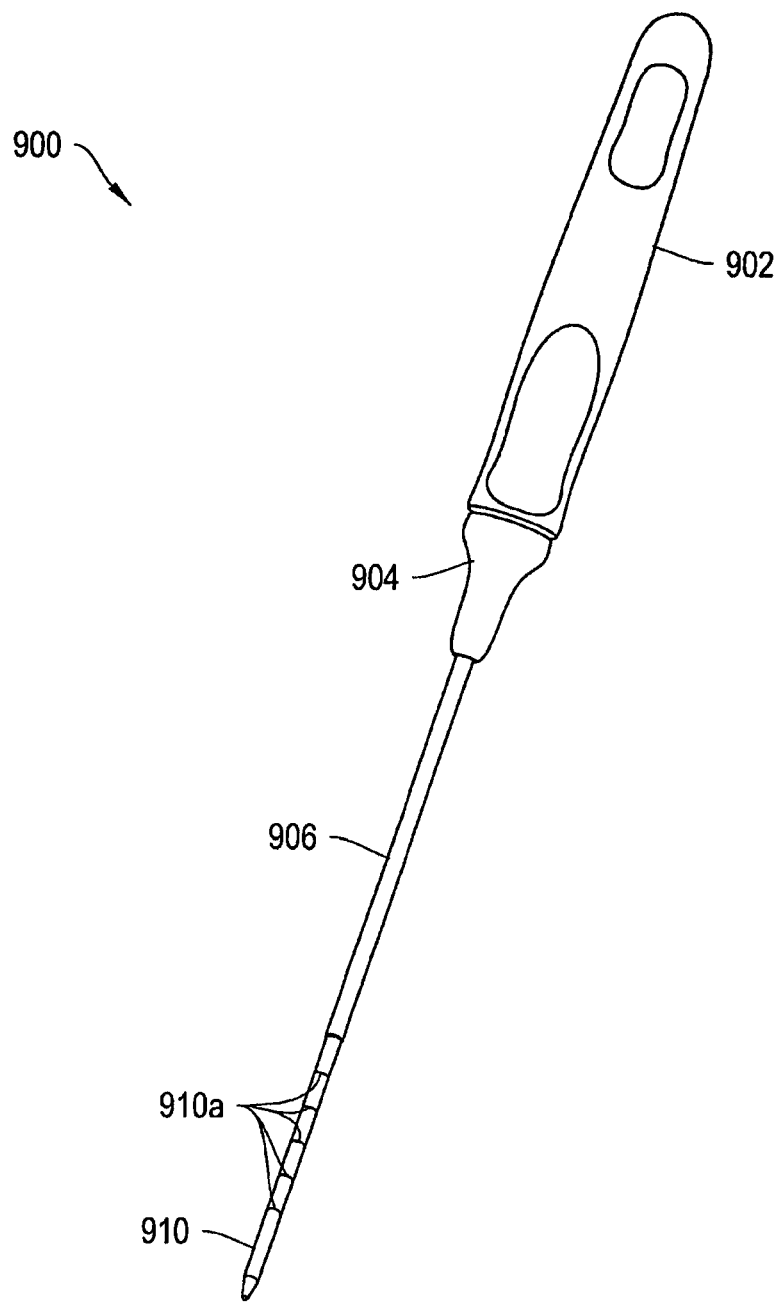
FIG. 30 shows the delivery device of FIG. 28 having increment markings on its shaft.

In addition to the cannula mark 908, the device 900 may include other marks that guide the operator. In order to measure how far to advance the button 904 and cannula 908, in certain embodiments the shaft 910 includes increment/measurement markings 910*a*. The operator can use the measurement markings to gauge the distance from the tip 916 of the shaft to the distal end of the cannula 908. FIG. 30 shows an alternate view of the device 900 of FIG. 29 with increment markings 910*a* etched into the shaft 910. The markings 910*a* can be disposed using other methods, such as disposing a biocompatible ink or stain on the shaft 910.

As described above, the exemplary meshes, anchors and delivery devices access target soft tissue regions, such as the obturator membranes, via single vaginal incisions. Exemplary surgical techniques for implanting the meshes will now be described. As illustrated herein, the procedure can be applied with meshes that are configured to support the urethra or bladderneck for the treatment of UI, and also with meshes that have longer anterior-to-posterior widths for supporting the bladder, uterus, and/or other organs located within the patient's pelvic region.

Figure 31A:
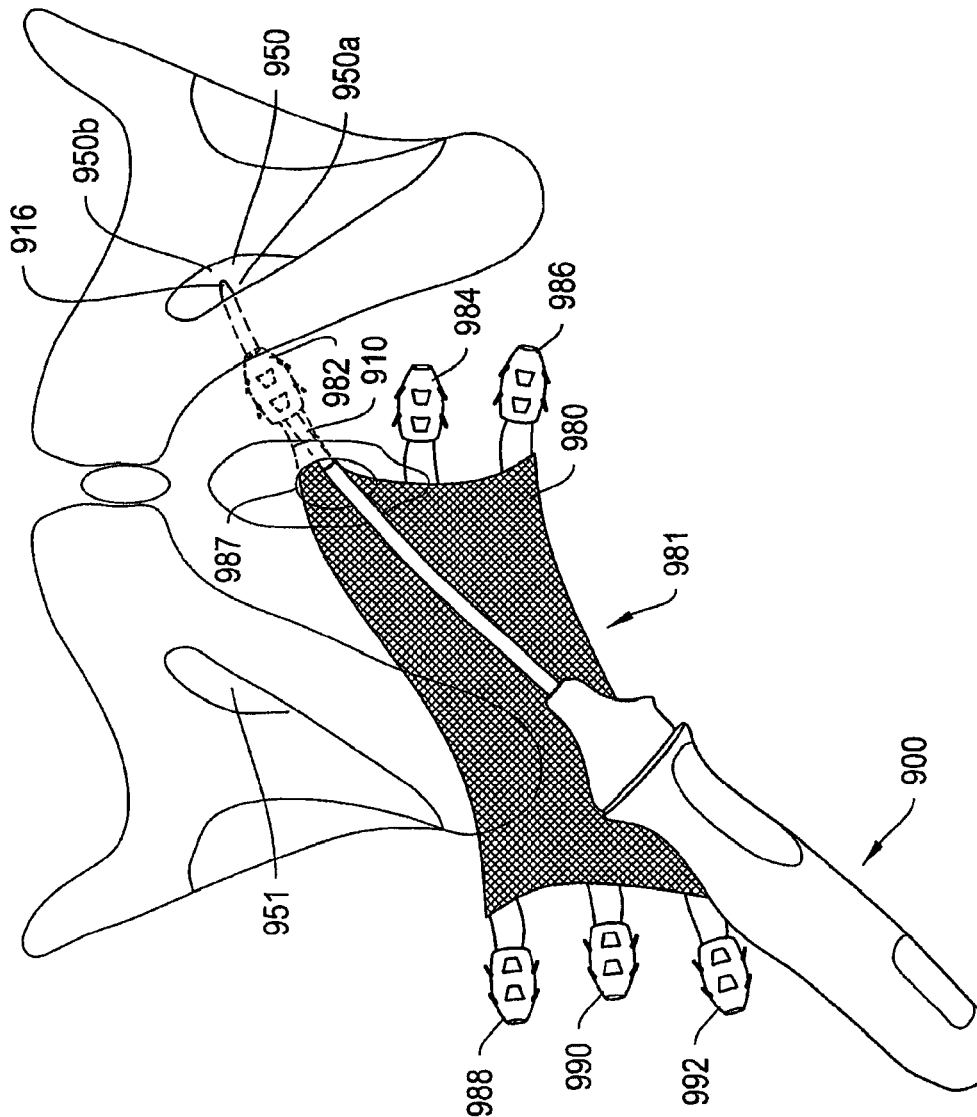
FIG. 31A illustrates a transobtural single vaginal incision procedure for delivering an implant sized and shaped to extend posterior to the bladderneck and support the base of the bladder.

FIG. 31A illustrates an exemplary single vaginal incision procedure for using delivery device 900 to deliver an implant assembly 981 for the treatment of a pelvic floor disorder. The exemplary implant assembly 981 is similar to implant assembly 630 of FIG. 26A, and in particular includes an implant 980 similar to implant 632 of FIG. 26A. The implant assembly 981 also includes three soft tissue anchors 982, 984, and 986 on one side of the implant, and three soft tissue anchors 988, 990, and 992 on a contralateral side. The anchors 982, 984, 986, 988, 990, and 992 are similar to anchor 500 of FIG. 21A, and couple to the implant 980 using filaments and filament locking mechanisms similar to those described in connection with FIG. 26A.

In the exemplary technique, the patient is placed on an operating table in a position to provide access to the pelvic region. The operator may subject the patient to local anesthesia, regional anesthesia, and/or general anesthesia or sedation according to his preference. Next, the operator makes a transverse incision (not shown) in the anterior vaginal wall of the patient and dissects the incision bilaterally according to his preference using, for example, surgical scissors. In certain implementations, the operator dissects bilaterally to the inferior pubic ramus on both sides of the patient. The operator then identifies a path of delivery of the implant by palpating tissue of the pelvic region. The operator may palpate by inserting his finger through the vaginal incision and may identify anatomical structures such as the obturator foramen.

Next, the operator accesses the patient's pelvic region via the single incision to insert the implant into the patient's pelvic region and secure the implant within the region so that at least a portion of the implant is located posterior to the bladderneck. To accomplish this, the operator first couples anchor 982 to the tip 916 of the shaft 910, inserts the distal end of the shaft 910 into the body through the external vaginal opening 987 and then guides the distal end of the shaft 910 through the vaginal incision towards an obturator membrane 950. The operator may palpate during delivery as preferred. The operator may also use the posterior portion of the patient's pubic bone as an anatomical landmark to assist in guiding the needle. The operator optionally secures the implant 980 against the shaft 910 during delivery so that the implant 980 does not obstruct the operator's vision or the path of delivery using any suitable sterile securing means, such as a sterile elastic band or tie.

The operator then punctures the obturator membrane 950 with the tip 916 but stops short of extending a portion of the tip 916 or shaft 910 through the surface of the patient's skin in the groin. The location of the puncture within the obturator membrane 250 depends on the anchor being delivered. For example, the operator delivers anchor 982 through a sufficiently posterior region 950b of the obturator membrane 950 so that the implant assembly 981 extends to posterior regions of the patient's pelvic floor and provides posterior support, while he delivers anchor 986 through an anterior region 950a of the obturator membrane 950 so that the implant assembly 981 extends to and supports anterior regions of the patient's pelvic floor (e.g., so that at least a portion of the implant 981 extends to a location that is posterior to the patient's bladder neck). In certain implementations, the operator generally delivers the implant 980 along a path that avoids certain pelvic structures, such as the internal pudendal artery, the pudendal canal, the perineal nerve, the labial nerve, and other vascular and nerve structures.

The operator may hear and/or feel a pop indicating that he has pierced the obturator membrane 950. The operator gauges the length from the vaginal incision to the obturator 950 by using the markings or indications (not shown) on the shaft 910, by using the mark 908 (not shown in this figure) on the cannula 906, and/or by visually gauging the length from the proximal edge of the anchor 982 to the vaginal incision to assure that the length of the implant 980 is suitable for the patient. As mentioned above, in certain implementations, the implant 980 includes a visual marking that the operator places under a predetermined anatomical landmark, such as the urethra or the bladder.

If needed, the operator further advances the shaft 910 to be near, contact, apply pressure to, poke ("tent-up"), or, in certain uses, pierce the epidermis (not shown) just beyond the obturator membrane 950, without penetrating entirely through the skin, until the shaft 910 is in an appropriate position to deliver the anchor 982. The operator may externally palpate the epidermis proximal to the obturator membrane to feel the shaft 910 poke the epidermis and confirm its location. In certain embodiments the operator stops extending the tip 916 when it reaches a position that is beneath the patient's stratum corneum, while in other embodiments the operator stops the tip 916 from extending to the epidermis. In certain embodiments the operator stops the tip 916 in the subcutaneous tissue or beneath the subcutaneous and does not extend the tip 916 to the dermal layer In certain implementations, the incision is made in the vagina so as to allow the inserted shaft to be near, contact, apply pressure to, or poke the skin at a position that is generally in line with the urethral meatus. The operator anchors the anchor 982 to the obturator membrane, and retracts the shaft 910, thereby decoupling the shaft 910 from the anchor 982, using methods discussed above.

The operator repeats this process for anchors 984 and 986, in each instance delivering the anchors through the same vaginal incision. Next, the operator repeats the process on the contralateral side, delivering anchors 988, 990, and 992 to the obturator membrane 951 through the same vaginal incision. The operator also inserts the region 981 of the implant 980 through the vaginal incision. In certain implementations the region 981 is inserted after the operator inserts the anchors 982, 984 and 986 on one side of the patient but before inserting anchors 988, 990 and 992 on the other side. Once all of the anchors 982, 984, 986, 988, 990, and 992 are delivered through the vaginal incision in the anterior vaginal wall and extended to respective obturator membranes 950 and 951, the entire implant 980 will have been delivered through the vaginal opening 987 and through the vaginal incision, and thus lie in a region anterior to the vaginal canal and supporting the urethra, bladder, and/or bladderneck.

The order in which the operator delivers the anchors 982, 984, 986, 988, 990, and/or 992 can vary. In certain implementations, the operator delivers anchors in a posterior-to-anterior order so that anterior portions of the implant do not obstruct or get in the way of the operator when delivering posterior anchors. Although cystoscopies are not required with the above-described procedure, the operator may perform a cystoscopy to check for bladder damage after delivering any or all of the anchors. Also during delivery, the operator optionally uses a pair of forceps or another suitable medical instrument to space the implant 980 from the urethra (not shown) during delivery of one or more of the anchors to prevent excessive tension or stress on the urethra. When completed, the operator reviews the implant 980 to confirm that it is properly placed under the organ needing support, then sutures the vaginal incision.

For certain patients, the lateral length of the implant 980 may be longer than the obturator-to-obturator length of that patient. In these cases, the operator may leave equal lengths of the implant displaced on external sides of the obturator membranes 950 and 951. By way of example, if the implant 980 has a lateral length of about 10 cm, then the patient with obturator to obturator length of about 7 cm will have about 1.5 cm of implant displaced on each side beyond the obturator membranes 950 and 951. Alternately, the manufacturer can supply implants with various lateral lengths to suit various patients.

Figure 31B:
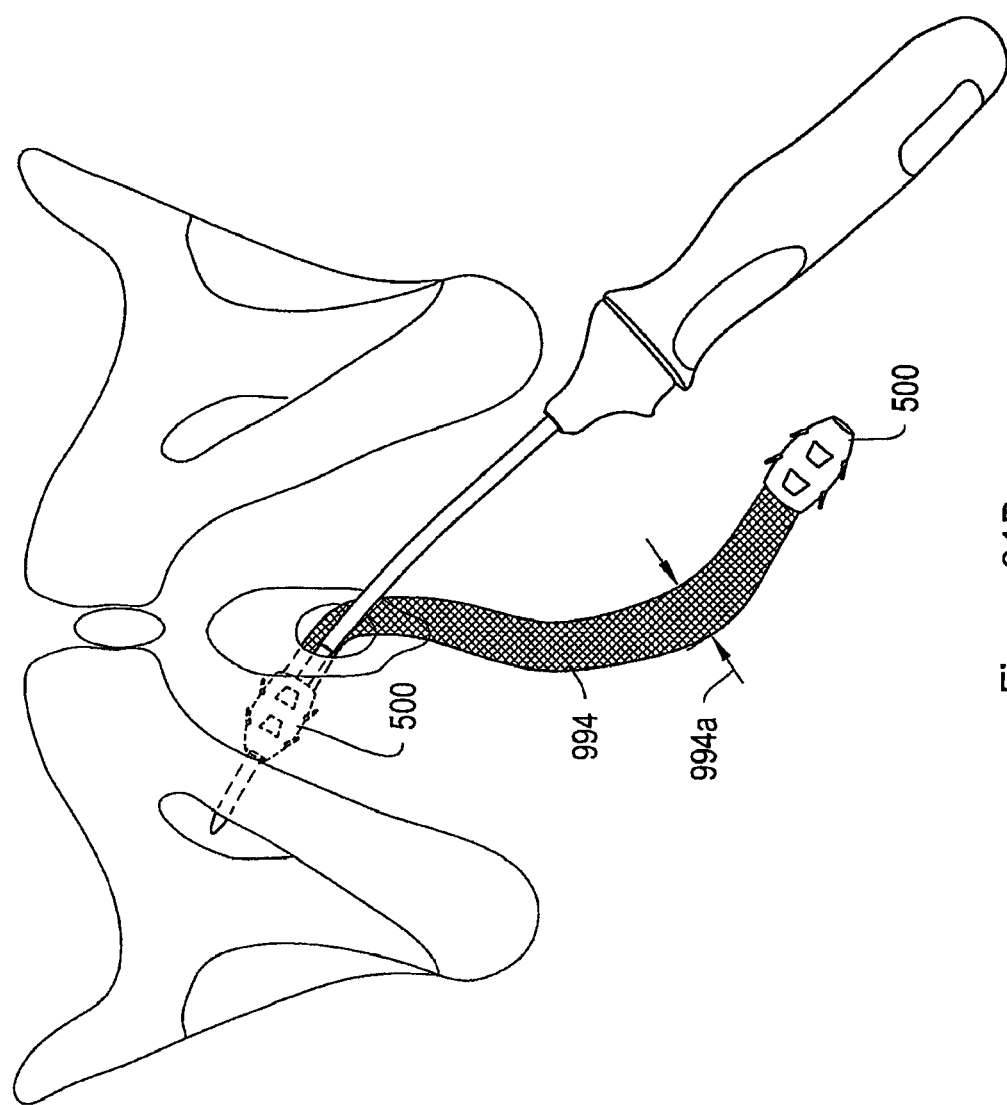
FIG. 31B shows a transobtural single incision procedure similar to the procedure depicted in FIG. 31A, for delivering an alternative implant sized and shaped for supporting the urethra and/or the bladderneck.

The device 900 and a similar delivery technique can be used to deliver non-woven implants discussed above (i.e., implant 140 of FIG. 7A), and/or implants that do not extend to posterior regions of the patient's anatomy and are instead sized and shaped for treating urinary incontinence. FIG. 31 B illustrates the use of device 900 to deliver an implant 994 with a narrower anterior-to-posterior width 994a that is designed to underlie and support the urethra and/or bladderneck of the patient. The implant 994 is directly coupled to anchors 500 of FIG. 21A. The operator uses a delivery method similar to that described in connection with FIG. 31 A, except that the operator only delivers two soft tissue anchors 500. In any event, the operator extends the soft tissue anchors 500 within the patient's soft tissue but stops short of extending a portion of the device through the surface of the patient's skin, as described above.

The surgical methods described above are non-limiting examples. Others will be apparent upon review of this disclosure. In certain alternative implementations, devices used to insert the implants are set forth in FIGS. 32A-34B. FIGS. 32A-C shows another illustrative delivery device 1060 that is sized and shaped for transobtural placement of an implantable implant through the single vaginal incision, and employable, without limitation, with any of the illustrative embodiments described herein. More particularly, the delivery device 1060 includes a handle 1062 with first 1062a and second 1062b substantially straight sections located substantially in a first plane and angled relative to each other, a transitional portion 1065 extending out of a distal end 1063 of the handle 1062 which interfits and extends axially out of the distal end 1063 of the second straight handle section 1062b, and a halo-shaped curved shaft 1064 extending from a distal end of the transitional portion 1065. The curved shaft 1064 includes a reduced diameter section 1064a at a distal end of the shaft 1064 and an increased diameter section 1064b at a proximal end of the shaft 1064. The increased diameter section 1064b and the reduced diameter section 1064a adjoin to form a shoulder/ledge 1064c. In use, an operator couples a soft tissue anchor to the device 1060 by interfitting the reduced diameter section 1064a of the shaft 1064 through a through-aperture of the soft tissue anchor. The increased diameter section 1064 should have a cross-section with a larger diameter than the diameter of the through-aperture, and thus the shoulder 1064c provides a mechanical stop that prevents the anchor from sliding proximally along the shaft 1064. In certain embodiments, the increased diameter section 1064b and the reduced diameter section 1064a are manufactured from a unitary body. However, in other embodiments, the increased diameter section comprises a flexible sheath or covering that an operator slides over the reduced diameter section 1064a and around the shaft 1064.

In this embodiment, the first substantially straight section 1062a has a longitudinal axis 1067 that is normal to the plane of the curved shaft 1064. However, the longitudinal axis 1067 can form any suitable angle with respect to the plane of the curved shaft (e.g., about 10, 20, 30, 45, 60, 70 or 80 degrees). By way of example, FIGS. 33A-B show two symmetric devices 1040 and 1041 similar to device 1060 of FIGS. 32A-C, but having alternative flat handles 1043, tapered tips 1046a at distal ends of the curved shafts 1046, and having longitudinal axes 1042 that form angles 1044 of about 60 degrees with respect to the planes of the curved shafts 1046.

Figure 34A:
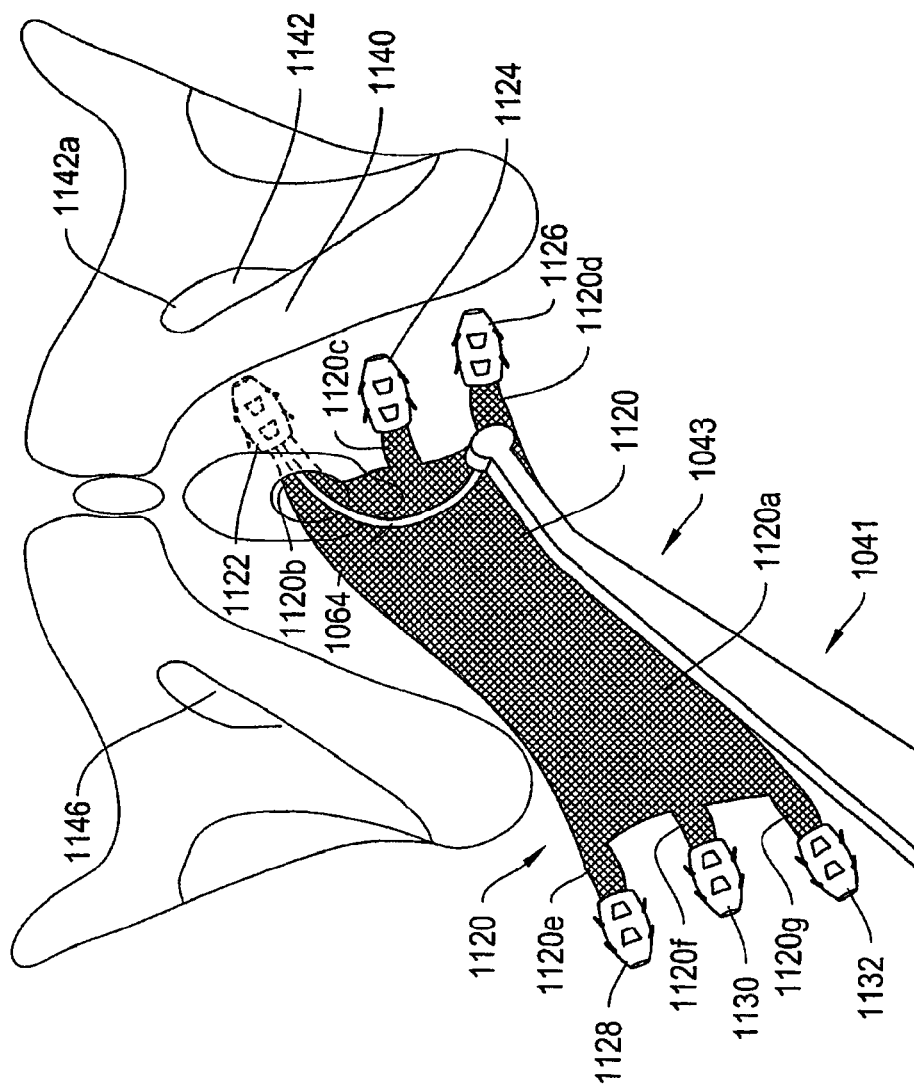
FIG. 34A shows an exemplary technique for delivering an implant sized and shaped to extend posterior to the bladderneck and support the base of the bladder using a transobtural single vaginal incision procedure.

FIG. 34A shows an exemplary technique for delivering an implant using device 1041. The implant 1120 is similar to implant 30 of FIG. 2A, except that implant 1120 includes a central region 1120a that is rectangular rather than trapezoidal. Anchors 1122, 1124, 1126, 1128, 1130, and 1132, similar to anchor 500 of FIG. 21A, directly couple to straps 1120b, 1120c, 1120d, 1120e, 1120f, and 1120g of implant 1120.

In the exemplary technique, first the patient is placed in a position to provide access to the pelvic region. The operator may subject the patient to local anesthesia, regional anesthesia, and/or general anesthesia or sedation according to his preference. Next, the operator makes a transverse incision (not shown) in the anterior vaginal wall of the patient and dissects the incision bilaterally according to his preference using, for example, surgical scissors. In certain implementations, the operator dissects bilaterally to the inferior pubic ramus on both sides of the patient. The operator then (optionally) identifies a path of delivery of the implant by palpating tissue of the pelvic region. The operator may palpate by inserting his finger through the vaginal incision and may identify anatomical structures such as the obturator foramen.

Next, the soft tissue anchor 1122 is interfitted over the tapered tip 1046a (not shown in this figure) of the delivery device shaft 1064. The operator grasps the handle 1043 and inserts the delivery device shaft portion 1046 with the anchor 1122 through the vaginal incision. With a lateral motion, the medical operator passes the curved shaft 1046 behind the ischiopubic ramus 1140 and pierces the obturator membrane 1142.

The delivery device shaft 1046 is then withdrawn through the vaginal incision with a retrograde motion by the operator, leaving the anchor 1122 implanted in or through the obturator membrane 1142 and, optionally, fixed to the obturator membrane 1142 as described above. The operator implants the anchor 1122 in a sufficiently posterior region 1142a of the obturator membrane 1142 so that the implant 1120 provides support to posterior anatomical structures and regions, such as the base of the bladder, in each instance delivering the anchors through the same vaginal incision.

This process is repeated for anchors 1124 and 1126. Next, the process is repeated for anchors 1128, 1130, and 1132 to the contralateral obturator membrane 1146 with the same or a second delivery device (i.e., the symmetric delivery device 1040 with opposite shaft 1064 curvature). As described above in connection with other exemplary techniques, the operator can perform cystoscopies during the procedure to check for bladder damage.

The halo-shaped curved shaft 1046 is beneficial at least in part in that the operator can navigate the tip 1046a about the ischiopubic ramus with lessened movement of his arm, wrist, and/or hand to provide a more accurate placement of the anchors. The operator may palpate during delivery as preferred. The operator may also use the posterior portion of the patient's pubic bone as an anatomical landmark to assist in guiding the needle. The halo-shaped curved shaft 1046 is also beneficial in part because it is shaped to avoid sensitive nerves and vascular structures that may be located in or near certain regions of the obturator membrane 1142. In some patients, these sensitive structures are more concentrated in superior regions of the obturator membrane 1142. Thus, in certain implementations, the operator delivers the anchors 1122, 1124, 1126, 1128, 1130, and 1132 to regions in the vicinity of the obturator membranes 1142 and 1146 that are proximal to inferior pubic bone structures, such as the inferior ramus of the pubis and the ramus of the ischium.

Figure 34B:
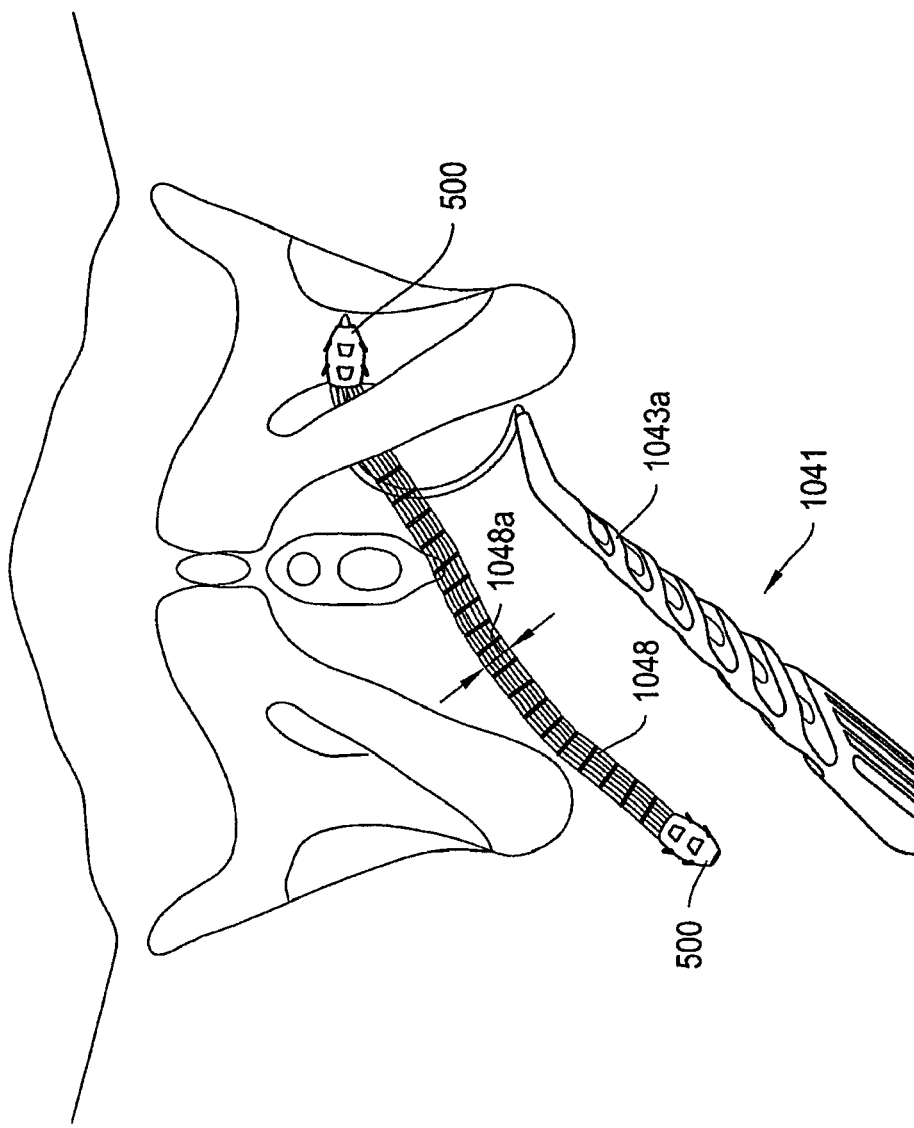
FIG. 34B shows aspects of a transobtural single incision procedure similar to the procedure depicted in FIG. 34A for delivering an alternative implant sized and shaped for supporting the urethra and/or the bladderneck.

As was the case with delivery device 900, delivery devices 1040, 1041, and 1060 can be used to deliver non-woven implants discussed above (i.e., implant 140 of FIG. 7a), and/or implants that do not extend to posterior regions of the patient's anatomy and are instead sized and shaped for treating urinary incontinence. FIG. 34B illustrates the use of device 1041 to delivery a mesh implant 1048 with a relatively narrow anterior-to-posterior width 1048a that is designed to underlie and support the urethra and/or bladderneck of the patient. The operator uses a delivery method similar to that described in connection with FIG. 34A, except that the operator only delivers two soft tissue anchors 500 coupled to the implant 1048. Additionally, the device 1041 includes an alternative handle configuration 1043a that includes grooves to provide the operator with a better grip of the device 1041.

Figure 35B:
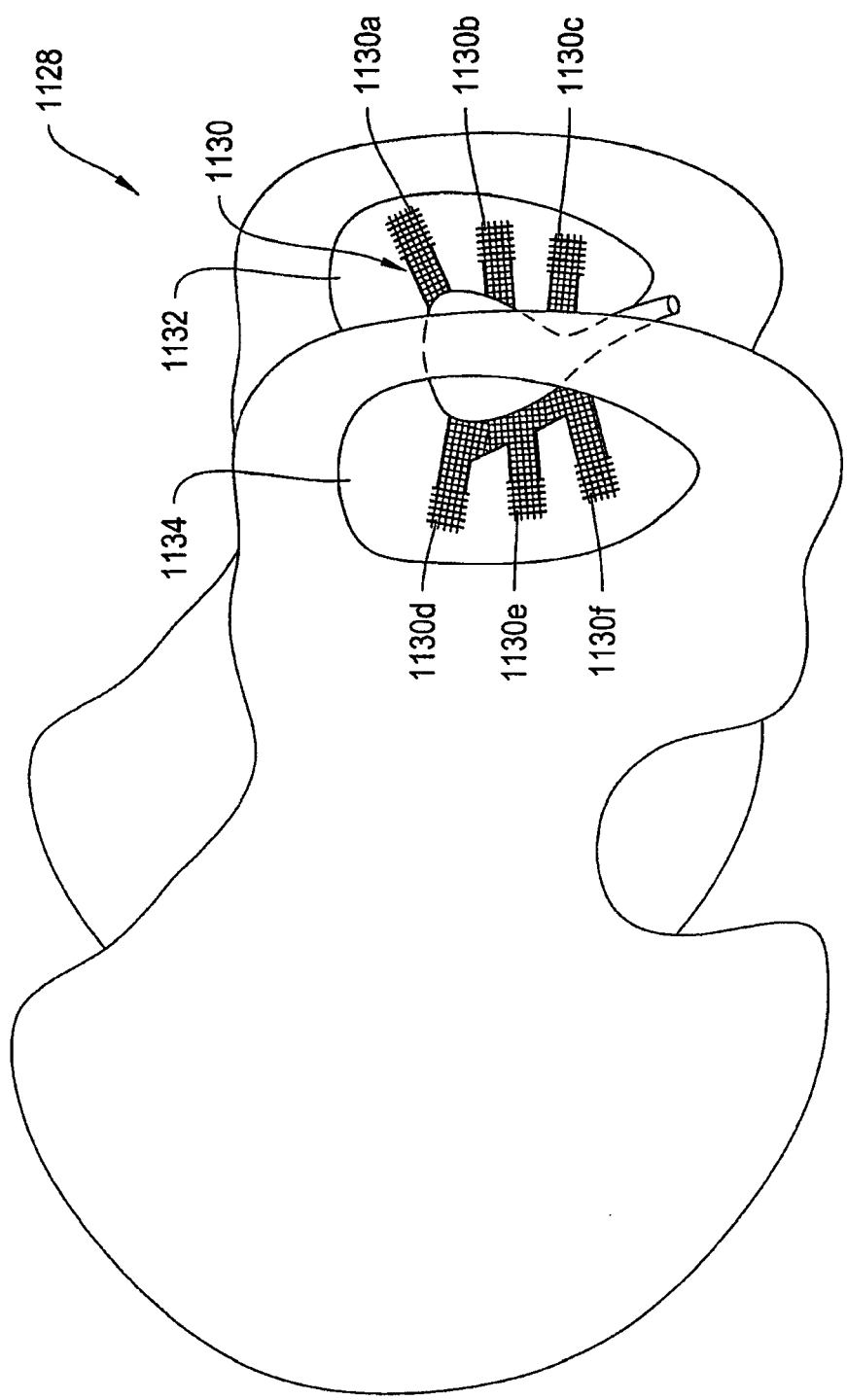
FIG. 35B shows aspects of a transobtural single incision procedure similar to the procedure depicted in FIG. 35A for delivering an implant sized and shaped to treat pelvic floor disorders.

FIG. 31 A-B and FIGS. 34A-B illustrate exemplary techniques for delivering implants that are secured to respective obturator membranes with soft tissue anchors. However, as mentioned above, in certain embodiments the implants are secured directly to target tissue regions of the retropubic space using tangs that are of unitary body with the implant. FIGS. 35A-B depict exemplary tanged implants and techniques for delivering and securing the implants.

In the exemplary techniques involving soft tissue anchors discussed above in connection with FIGS. 31A-B and FIGS. 34A-B, the implant couples to soft tissue anchors, which are then coupled to a delivery device. However, when no soft tissue anchors are used, the implant couples directly to the delivery device. FIG. 35A depicts an implant 1102 directly coupled to the delivery device 1060 that was shown in FIGS. 32A-32C. The implant 1102 includes tanged portions 1104a and 1104b at respective ends of the implant 1102, and a non-tanged portion 1104c between the tanged portions 1104a and 1104b. The tanged implant 1102 can be manufactured using a technique similar to that described in connection with the tanged implant 30 of FIG. 2B.

In use, the operator couples the implant 1102 directly to the delivery device 1060 by sliding the reduced diameter portion 1064a through one of the interstices 1110 of the implant 1102. In order for the reduced diameter portion 1064a to fit through one of the interstices, in certain embodiments the reduced diameter portion 1064a has a diameter of less than about 1 mm. The operator then follows the same steps as those described in connection with FIG. 34B to guide the distal end of the delivery device 1060 to the obturator membrane 1112b. However, instead of piercing a soft tissue anchor through the obturator membrane, the operator drives the reduced diameter portion 1064*a* of the device 1060 with at least part of the tanged portion 1104*b* through the obturator membrane 1112*b*. The delivery device 1060 is then withdrawn through the vaginal incision leaving the tanged portion 1104*b* implanted in or through the obturator membrane 1112*b*. The operator then repeats this process to. anchor the contra-lateral tanged portion 1104*a* to the contra-lateral obturator membrane 1112*a*.

The tanged implant 1102 is sized and shaped to treat urinary incontinence by supporting the patient's urethra and/or bladderneck. Tanged implants can also be used for treating other pelvic floor disorders. FIG. 35B shows an oblique view of the pelvic region 1128 of a patient with an implant 1130 similar to the implant 30 of FIG. 2, but having tanged straps 1130*a-f*. To deliver the implant 1130, the operator uses a similar method as that described in connection with FIG. 35A to deliver each of the tanged ends 1130*a-c* to a first obturator membrane 1132 and to then deliver each of the tanged straps 1130*d-f* to a contra-lateral obturator membrane 1134.

As noted above, after placing a surgical implant, the operator tensions the implant to provide the proper support to anatomical structures of the pelvic region using methods described above.

In addition to the obturator membranes, in certain alternative implementations an operator anchors the implant to other anatomical structures. These structures include posterior or lateral tissues or muscles, such as the sacrospinous ligament and the levator ani muscle. The sacrospinous ligament is a thin and triangular tissue that is attached by its apex to the spine of the patient's ischium, and medially, by its broad base, to the lateral margins of the sacrum and coccyx in front of the sacrotuberous ligament. The sacrospinous ligament is a convenient location to anchor mesh straps in the posterior regions of the pelvic floor in order to provide posterior support. The levator ani muscle is a broad, thin muscle situated generally on the side of the pelvis that is attached to the inner surface of the lesser pelvis. It is a convenient location to anchor mesh straps in order to provide lateral and/or posterior support and tension for a surgical implant.

More particularly, FIG. 36 shows an exemplary position of a surgical implant 1142 in the pelvic region 1140 of a patient. The implant includes three sets of straps. The anterior set of straps 1142*a-b* anchor to respective obturator membranes as discussed above in connection with other exemplary implant positions, and provide anterior support to the implant 1142. The lateral set of straps 1142*b-c* anchor to respective target tissue regions 1144*a* and 1144*b* about the tendinous arch of the levator ani muscle and provide lateral support to the implant 1142. The posterior set of straps 1142*e-f* anchor to respective target tissue regions 1146*a* and 1146*b* of the sacrospinous ligament and provide posterior support to the implant 1142. Each of the straps 1142*a-f* anchors to a respective target tissue region via a soft tissue anchor 500 discussed in connection with FIG. 21A. However, in other embodiments the straps 1142*a-f* have tangs that anchor to respective target tissue regions.

One exemplary implantation technique is performed in three phases. In a first phase, the operator inserts and secures the posterior straps 1142*e-f* into the sacrospinous ligament. In a second phase, the operator inserts and secures the lateral straps 1142*c-d* into the levator ani muscle. In a third phase, the operator inserts the anterior straps 1142*a-b* through the obturator foramen and secures the straps in either obturator membranes or in the patient's tissues proximal to the obturator canals.

More particularly, in the first phase, to insert the strap 1142*e*, a medical operator creates an incision in a patient's anterior vaginal wall 1148. The incision can be dissected or extended as required to facilitate access of a delivery device to target region 1146*b*. Next, the operator couples, preferably external to the body, mesh strap 1142*e* with delivery device 900 described above in connection with FIG. 28 via the soft tissue anchor 500 (not shown) described in connection with FIG. 21A.

The operator then inserts the device 900 and the coupled mesh strap 1142*e* through the vaginal opening, into the vaginal canal, and through the vaginal incision. The operator guides the tip 916 of the device towards the target region 1146*a* of the sacrospinous ligament, and pierces and drives the mesh strap 1142*e* through the target region 1146*a*. The operator then retracts the device, leaving the strap 1142*e* anchored to the target region 1146*a*. For strap 1142*e*, as well as the other straps 1142*a-d* and 1142*f*, the operator may use other devices having varying shaft lengths and curvatures in order to reach the appropriate target tissue region via the vaginal incision.

The operator then delivers the mesh strap 1142*f* through the vaginal opening and through the vaginal incision in a similar manner as 1142*e*. The vaginal incision may be dissected or extended as necessary to facilitate access of delivery device 900 to target region 1146*b*. The operator may use the same delivery device 900 for delivery of strap 1142*f*, or alternatively may use a second delivery device 900.

In the second phase, the operator inserts the straps 1142*d-e* into target regions 1144*a* and 1144*b* of the levator ani muscle. To insert strap 1142*c*, the operator first couples delivery device 900 to the mesh strap 1142*c* using a soft tissue anchor 500, then inserts the device 900 into the vaginal canal, and through the vaginal incision. The operator then pierces and drives the mesh strap 1142*c* through the target region 1144*a* of the levator ani muscle, and retracts the delivery device 900 using methods discussed above. The operator similarly delivers mesh strap 1142*d* to target region 1144*b* of the tendinous arch of the levator ani muscle contralateral to target region 1144*a* using delivery device 900.

In a third phase, the operator inserts the anterior straps 1142*a* and 1142*b* through the obturator foramen and secures the straps to respective obturator membranes or to the patient's tissues proximal the obturator canals using any of the exemplary methods and devices discussed above.

In alternative embodiments, the implants can be stitched or sutured to the target tissue regions. Moreover, the operator may use any operative combination of the above-described techniques. For example, the operator may anchor any of the implants described herein on one side of the patient's retropubic space using soft tissue anchors, while anchoring the same implant to the contra-lateral side of the patient's retropubic space using tanged portions of the implant.

According to another feature, the implants of the invention may include any suitable end portions, such as tissue dilators, anchors, and association mechanisms for associating the implant with the delivery devices of the invention. The implants and other features described herein may be adapted for use in multi-incision procedures, such as, for example, U.S. 2005/0245787, 2005/0250977, 2003/0220538, and 2004/0249473. They may also include other implants (i.e., slings), sling assemblies, sling delivery approaches, sling assembly-to-delivery device association mechanisms, and sling anchoring mechanisms. These and other features with which the delivery devices, implants, methods, and kits of the invention may be employed are disclosed in U.S. Pat. No. 6,042,534, entitled "Stabilization sling for use in minimally invasive pelvic surgery," U.S. Pat. No. 6,755,781, entitled "Medical slings," U.S. Pat. No. 6,666,817, entitled "Expandable surgical implants and methods of using them," U.S. Pat. No. 6,042,592, entitled "Thin soft tissue surgical support mesh," U.S. Pat. No. 6,375,662, entitled "Thin soft tissue surgical support mesh," U.S. Pat. No. 6,669,706, entitled "Thin soft tissue surgical support mesh," U.S. Pat. No. 6,752,814, entitled "Devices for minimally invasive pelvic surgery," U.S. Ser. No. 10/918,123, entitled "Surgical Slings," U.S. patent application Ser. No. 10/641,376, entitled "Spacer for sling delivery system," U.S. patent application Ser. No. 10/641,192, entitled "Medical slings," U.S. Ser. No. 10/641,170, entitled "Medical slings," U.S. Ser. No. 10/640,838, entitled "Medical implant," U.S. patent application Ser. No. 10/460,112, entitled "Medical slings," U.S. patent application Ser. No. 10/631,364, entitled "Bioabsorbable casing for surgical sling assembly," U.S. Ser. No. 10/092,872, entitled "Medical slings," U.S. patent application Ser. No. 10/939,191, entitled "Devices for minimally invasive pelvic surgery," U.S. patent application Ser. No. 10/774,842, entitled "Devices for minimally invasive pelvic surgery," U.S. patent application Ser. No. 10/774,826, entitled "Devices for minimally invasive pelvic surgery," U.S. Ser. No. 10/015,114, entitled "Devices for minimally invasive pelvic surgery," U.S. patent application Ser. No. 10/973,010, entitled "Systems and methods for sling delivery and placement," U.S. patent application Ser. No. 10/957,926, entitled "Systems and methods for delivering a medical implant to an anatomical location in a patient," U.S. patent application Ser. No. 10/939,191, entitled "Devices for minimally invasive pelvic surgery," U.S. patent application Ser. No. 10/918,123, entitled "Surgical slings," U.S. patent application Ser. No. 10/832,653, entitled "Systems and methods for sling delivery and placement," U.S. patent application Ser. No. 10/642,397, entitled "Systems, methods and devices relating to delivery of medical implants," U.S. patent application Ser. No. 10/642,395, entitled "Systems, methods and devices relating to delivery of medical implants," U.S. patent application Ser. No. 10/642,365, entitled "Systems, methods and devices relating to delivery of medical implants," U.S. patent application Ser. No. 10/641,487, entitled "Systems, methods and devices relating to delivery of medical implants," U.S. patent application Ser. No. 10/094,352, entitled "System for implanting an implant and method thereof," U.S. patent application Ser. No. 10/093,498, entitled "System for implanting an implant and method thereof," U.S. patent application Ser. No. 10/093,450, entitled "System for implanting an implant and method thereof," U.S. patent application Ser. No. 10/093,424, entitled "System for implanting an implant and method thereof," U.S. patent application Ser. No. 10/093,398, entitled "System for implanting an implant and method thereof," and U.S. patent application Ser. No. 10/093,371, entitled "System for implanting an implant and method thereof," U.S. Pat. No. 6,197,036, entitled "Pelvic Floor Reconstruction," U.S. Pat. No. 6,691,711, entitled "Method of Correction of Urinary and Gynecological Pathologies Including Treatment of Incontinence," U.S. Pat. No. 6,884,212, entitled "Implantable Article and Method," U.S. Pat. No. 6,911,003, entitled "Transobturator Surgical Articles and Methods," U.S. patent application Ser. No. 10/840,646, entitled "Method and Apparatus for Cystocele Repair," U.S. application Ser. No. 10/834,943, entitled "Method and Apparatus for Treating Pelvic Organ Prolapse," U.S. patent application Ser. No. 10/804,718, entitled "Prolapse Repair," and U.S. patent application Ser. No. 11/115,655, entitled "Surgical Implants and Related Methods." The entire contents of all cited references are incorporated herein by reference in their entirety. Variations, modifications, and other implementations of what is described may be employed without departing from the spirit and the scope of the invention. More specifically, any of the method, system and device features described above or incorporated by reference may be combined with any other suitable method, system or device features disclosed herein or incorporated by reference, and is within the scope of the contemplated invention. All operative combinations between one disclosed embodiment and any other embodiments are also contemplated. It is intended that the scope of the invention be limited not by this detailed description but rather by the claims appended hereto.

The invention claimed is:

1. A method for implanting a surgical implant in the pelvic floor region of a patient for pelvic floor repair comprising:
creating an incision in a vaginal wall of a patient;
coupling a mesh sling to a delivery device, the mesh sling configured to support a urethra and a bladder of the patient, the mesh sling including a central portion having a size sufficient to extend from the urethra to the bladder, the mesh sling including a first end portion having at least two first anchors and a second end portion having at least two second anchors;
inserting the delivery device through the incision;
implanting the mesh sling within the pelvic floor of the patient such that the central portion of the mesh sling extends from the urethra to the bladder of the patient and provides support to the urethra and the bladder; and
wherein the implanting includes coupling the at least two first anchors to a first obturator membrane and coupling the at least two second anchors to a second obturator membrane such that the mesh sling extends from a position proximate to the first obturator membrane to a position proximate to the second obturator membrane.

2. The method of claim 1, wherein the mesh sling further comprises at least one non-tanged portion.

3. The method of claim 1, further comprising adjusting tension of the mesh sling.

4. The method of claim 1, wherein the delivery device further comprises a shaft and a slideable cannula disposed about the shaft.

5. The method of claim 1, wherein inserting the delivery device further comprises aligning a shaft of the delivery device toward the first obturator membrane.

6. The method of claim 1, wherein the delivery device couples to one of the at least two first and second anchors.

7. The method of claim 1, wherein the delivery device directly couples to one of the at least two first and second anchors.

8. The method of claim 1, wherein the delivery device couples to an anchor of the at least two first and second anchors by filaments which space the coupled anchor away from the mesh sling.

9. The method of claim 1, wherein the delivery device further comprises a first strap end for aligning with the first obturator membrane and a second strap end for aligning with the second obturator membrane.

10. The method of claim 1, wherein at least one of the at least two first and second anchors is un-barbed.

11. The method of claim 1, wherein the mesh sling has at least one tanged mesh portion.

12. The method of claim 1, wherein the at least two first anchors includes at least two first soft tissue anchors, and the at least two second anchors includes at least two second soft tissue anchors.

13. The method of claim 12, wherein the at least two first and second soft tissue anchors are coupled to the first and second end portions, respectively, via filaments.

14. The method of claim 1, wherein the first end portion defines at least two first straps, and the second end portion defines at least two second straps, wherein the at least two first anchors are tangs on the at least two first straps, and the at least two second anchors are tangs on the at least two second straps.

15. The method of claim 1, wherein the at least two first anchors includes three anchors, and the at least two second anchors includes three anchors.

16. The method of claim 1, wherein the mesh sling includes a first portion configured to be disposed on one side of the urethra, a bladderneck, and the bladder, a second portion configured to be disposed under the urethra, and a third portion configured to be disposed posterior to the bladderneck to support tissue near a region of the bladder and a region of the uterus.

17. A method for implanting a surgical implant in the pelvic floor region of a patient for pelvic floor repair comprising:

creating an incision in a vaginal wall of a patient;

coupling a mesh sling to a delivery device, the mesh sling configured to support a urethra and a bladder of the patient, the mesh sling including a central portion having a size sufficient to extend from the urethra to the bladder, the mesh sling including a first end portion having at least two straps and a second end portion having at least two straps;

inserting the delivery device through the incision;

implanting the mesh sling within a pelvic floor of the patient such that the central portion of the mesh sling extends from the urethra to the bladder of the patient and provides support to the urethra and the bladder, wherein the implanting the mesh sling includes coupling portions of the at least two straps of the first end portion to a first obturator membrane and coupling portions of the at least two straps of the second end portion to a second obturator membrane in a manner that the mesh sling extends from a position proximate to the first obturator membrane to a position proximate the second obturator membrane.

18. The method of claim 17, wherein each of the straps of the first end portion and the second end portion includes at least one tanged portion.

* * * * *